(12) United States Patent
Dupont et al.

(10) Patent No.: US 6,635,285 B2
(45) Date of Patent: *Oct. 21, 2003

(54) SHARK CARTILAGE EXTRACT: PROCESS OF MAKING, METHODS OF USING, AND COMPOSITIONS THEREOF

(75) Inventors: Éric Dupont, Quebec (CA); Paul Brazeau, Québec (CA); Christina Juneau, Québec (CA); Daniel H. Maes, Huntington, NY (US); Kenneth Marenus, Dix Hills, NY (US); Richard Béliveau, Québec (CA)

(73) Assignee: Les Laboratoires Aeterna, Inc., Quebec (CA)

(*) Notice: Subject to any disclaimer, the term of this patent is extended or adjusted under 35 U.S.C. 154(b) by 0 days.

This patent is subject to a terminal disclaimer.

(21) Appl. No.: 10/068,950

(22) Filed: Feb. 7, 2002

(65) Prior Publication Data

US 2003/0013858 A1 Jan. 16, 2003

Related U.S. Application Data

(60) Division of application No. 09/504,065, filed on Feb. 15, 2000, now Pat. No. 6,380,366, which is a continuation-in-part of application No. 08/693,535, filed on Aug. 8, 1996, now Pat. No. 6,028,118, which is a continuation-in-part of application No. 08/550,003, filed on Oct. 30, 1995, now Pat. No. 6,025,334, which is a continuation-in-part of application No. 08/384,555, filed on Feb. 3, 1995, now Pat. No. 5,618,925, which is a continuation-in-part of application No. 08/234,019, filed on Apr. 28, 1994, now abandoned.

(51) Int. Cl.$^7$ .............................................. A61K 35/34
(52) U.S. Cl. .................... 424/548; 424/520; 424/549; 514/859; 514/863; 530/350; 530/400; 530/412; 530/414; 530/415; 530/417; 530/418; 530/422; 530/857
(58) Field of Search ................. 530/350, 400, 530/412, 414, 415, 417, 418, 422, 857, 356; 424/520, 548, 549; 514/859, 863

(56) References Cited

U.S. PATENT DOCUMENTS

| | | |
|---|---|---|
| 3,478,146 A | 11/1969 | Balassa |
| RE28,093 E | 7/1974 | Balassa |
| 3,966,908 A | 6/1976 | Balassa |
| 4,042,457 A | 8/1977 | Kuettner et al. |
| 4,212,857 A | 7/1980 | Balassa et al. |
| 4,243,582 A | 1/1981 | Spilburg et al. |
| 4,350,682 A | 9/1982 | Balassa |
| 4,356,261 A | 10/1982 | Kuettner |
| 4,444,752 A | 4/1984 | Prudden |
| 4,456,589 A | 6/1984 | Holman et al. |
| 4,469,676 A | 9/1984 | Hecmati |
| 4,473,551 A | 9/1984 | Schinitsky |
| 4,656,137 A | 4/1987 | Balassa |
| 4,746,729 A | 5/1988 | Kuettner et al. |
| 4,749,522 A | 6/1988 | Kamarei |
| 4,822,607 A | 4/1989 | Balassa et al. |
| 5,075,112 A | 12/1991 | Lane |
| 5,096,892 A | 3/1992 | Folkman et al. |
| 5,135,919 A | 8/1992 | Folkman et al. |
| 5,583,153 A | 12/1996 | Brahn |
| 5,618,925 A * | 4/1997 | Dupont et al. ............... 530/400 |
| 5,843,920 A | 12/1998 | Weisz |
| 5,985,839 A | 11/1999 | Dupont et al. |
| 6,025,334 A * | 2/2000 | Dupont et al. ................ 514/21 |
| 6,028,118 A * | 2/2000 | Dupont et al. .............. 514/863 |
| 6,168,807 B1 | 1/2001 | Dupont et al. |
| 6,380,366 B1 * | 4/2002 | Dupont et al. .............. 530/422 |

FOREIGN PATENT DOCUMENTS

| | | |
|---|---|---|
| JP | 45-001444 | 1/1970 |
| JP | 59-039828 | 3/1984 |
| JP | 60-178820 | 9/1985 |
| WO | 9309766 | 5/1993 |
| WO | 9412510 | 6/1994 |
| WO | 9503036 | 2/1995 |
| WO | 9532722 | 12/1995 |
| WO | 9623512 | 8/1996 |
| WO | 9716197 | 5/1997 |

OTHER PUBLICATIONS

Oikawa, T., et al., "A novel angiogenic inhibitor derived from Japanese shark cartilage (I). Extraction and estimation of inhibitory activities toward tumor and embryonic angiogenesis." *Cancer Letters*, 51 (1990) 181–186.

Moses, M., et al., "Inhibitors of Angiogenesis," *Biotech* 1991; 9; pp. 630–634.

Folkman, J., et al., "Angiogenic Factors," *Science*, vol. 235, pp. 442–446.

Luer, C.A., "Inhibitors of Angiogenesis from Shark Cartilage," Fed. Proc. 45(4):949.

Suzuki, et al., "Cartilage–derived Antitumor Factor (CATF): A High Molecular Weight Fraction Cartilage Extract Inhibits Solid Tumor Growth," *Journal of Bone and Mineral Metabolism*, 1984 vol. 2, No. 3, pp. 53–57.

(List continued on next page.)

*Primary Examiner*—Jeffrey Stucker
(74) *Attorney, Agent, or Firm*—Haynes and Boone, LLP

(57) ABSTRACT

The present invention relates to cartilage extracts and to a method of producing the same. Shark cartilage extracts having anti-angiogenic, anti-tumor, anti-inflammatory and anti-collagenolytic activities have been obtained by an improved process. The process comprises the steps of obtaining a crude cartilage extract in an aqueous solution, this crude extract being fractionated to recover molecules of a molecular weight less than about 500 kDa. Some of the biologically active components of the extract are prepared by further fractionation. The cartilage extract can be used for treating diseases or conditions having etiological components selected from the group consisting of tumor proliferation, angiogenesis, inflammation, metalloprotease activity and collagenolysis. Several cosmetic applications based on the capacity of the liquid extract to improve skin conditions are also disclosed. A simple and efficient process for the preparation of cartilage extracts is also disclosed.

36 Claims, 31 Drawing Sheets

OTHER PUBLICATIONS

Langer, R., et al., "Isolation of a Cartilage Factor That Inhibits Tumor Neovascularization," *Science*, vol. 193, pp. 70–72.

Sorgente, N., et al., "The Resistance of Certain Tissues in Invasion," *Laboratory Investigation*, vol. 32, No. 2, 1975, pp. 217–222.

Brem, H., et al., "Inhibition of Tumor Angiogenesis Mediated by Cartilage," *The Journal of Experimental Medicine*, vol. 141, 1975, pp. 427–439.

Kuettner, K., et al., "Tumor Cell Collagenase and its Inhibition by a Cartilage–Derived Protease Inhibitor," *Science*, vol. 196, pp. 653–654.

Weingarten, M., et al., "Synthetic Substrates of Vertebrate Collagenase," *Biochemistry* 24, 6730–6734 (1985).

Sadove, A., et al., "Inhibition of Mammary Carcinoma Invasiveness with Cartilage–Derived Inhibitor," *Orthopaedic Surgery*, pp. 499–501.

Paull, B., et al., "Regulation of Tumor Invasion by Cartilage–Derived Anti–Invasion Factor in Vitro," *JNCI*, vol. 67, No. 1, pp. 65–73 (1981).

Morales, T., et al., "Characterization of the Metalloproteinase Inhibitor Produced by Bovine Articular Chondrocyte Cultures," *Biochimic et Biophysica Acta*, 760, pp. 221–229 (1983).

Moses, M., et al., "Identification of an Inhibitor of Neovascularization from Cartilage," *Science*, vol. 248, pp. 1408–1410.

Moses, M., et al., "A Metalloproteinase Inhibitor as an Inhibitor of Neovascularization," *Journal of Cellular Biochemistry*, vol. 47, pp. 230–235 (1991).

Moses, M., "A Cartilage–Derived Inhibitor of Neovascularization and Metalloproteinases," *Clinical and Experimental Rheumatology* 11 (Supp. 8), pp. S67–S69 (1993).

Moses, M., et al., "Metalloproteinase Inhibition as a Mechanism for the Inhibition of Angiogenesis," *Angiogenesis: Key Principles–Science–Technology–Medicine*, pp. 146–151 (1992).

McGuire, T., et al., "Antiproliferative Activity of Shark Cartilage With and Without Tumor Necrosis–Factor–$\alpha$ in Human Umbilica Vein Endothelium," *Pharmacotherapy*, 1996;16(2), p. 237.

Lee, A., et al., "Shark Cartilage Contains Inhibitors of Tumor Angiogenesis," *Science*, vol. 221, pp. 1186–1187.

Medina, "Mammary Tumorigenesis in Chemical Carcinogen–Treated Mice. VI. Tumor–Producing Capabilities of Mammary Dysplasias in BALB/cCrgl Mice," *J. Natl. Cancer Inst.*, vol. 57, No. 5, pp. 1185–1189.

Davis, P., et al., "Inhibition of Angiogenesis by Oral Ingestion of Powdered Shark Cartilage in a Rat Model," *Microvascular Research*, vol. 54, pp. 178–182 (1997).

Mathews, J., "Media Feeds Frenzy Over Shark Cartilage as Cancer Treatment," *Journal of the National Cancer Institute*, vol. 85, No. 15, pp. 1190 (1993).

Scott, et al., "Selective Demineralization of Hard Tissues in Organic Solvents: Retention or Extraction of Proteoglycan?", J. Microsc., 134(3), pp. 291–291.

Pavia, et al., "Introduction to Organic Laboratory Techniques a Contemporary Approach," 2nd Ed., Saunders College Publishing, Philadelphia, pp. 500–501.

Burdick, et al., "High Purity Solvent Guide," 2nd Ed., Burdick & Johnson Laboratories, Inc., pp. 128–137.

Sheu, et al., "Effect of U–995, a Potent Shark Cartilage–Derived Angiogenesis Inhibitor, an Anti–Angiogenesis and Anti–Tumor Activities," Abtucabcer Researcg, 18L, 4435–4442 (1998).

Arnett, F., et al., Arthritis & Rheumatism, 31(3):315–324 (1988).

Chabot–Fletcher, M., et al., "Interleukin–8 Production is Regulated by Protein Kinase C in Human Keratinocytes," *The Journal of Investigative Dermatology*, 103(4):509–515 (1994).

Elias, P.M., "Epidermal Lipids, Barrier Fnction, and Desquamation," *J. Invest. Dermatol.* 80:044s–049s (1993).

Grove, G.L., "Age–Related Differences in Healing of Superficial Skin Wounds in Humans" in *The effects of aging in oral mucosa and skin.* ed. Squier & Hill CRC Press, pp. 121–127.

Matsui, M.S., et al., "Protein Kinase C in Normal Human Epidermal Keratinocytes During Proliferation and Calcium–Induced Differenciation," *J. Invest. Dermatol.* 99:565–571 (1992).

Medina, D., et al., "Response of Hyperplastic Aveolar Nodule Outgrowth–Line D1 to Mammary Tumor Virus, Nodule–Inducing Virus, and Prolonged . . . ", *J. Natl. Cancer Inst.* 42:303–310 (1969).

Nickoloff, B.J., et al., "Aberrant Production of Interleukin–8 and Trombospondin–1 Psoriastic Keratinocytes Mediates Angiogenesis," *Am. J. Pathology* 144(4):820–828 (1994).

Oresajo, C., et al., "Eye Area Problems Puffiness, Bags, Dark Circles and Crowsfeet," *Cosmetics and Toiletries* 102:29–34 (1987).

Pinnagoda, "Guidelines for transepidermal water loss (TEWL) measurement," *Contact Dermatitis* 22:164–178 (1990).

Ritchie, et al., "Clinical Studies with an Articular Index for the Assessment of Joint Tenderness in Patients with Rheumatoid Arthritis," *Quarterly Journal of Medicine*, New Series XXXVII, No. 147, pp. 393–407 (1968).

Blood, C. H., et al., "Tumor interactions with the vasculature: angiogenesis and tumor metastatis," *Biochimica et Biophysica Acta*, 1032:89–118 (1990).

Brem, S., "Angiogenesis and Cancer Control: From Concept to Therapeutic Trial," *JMCC*, 6(5):436–458 (1999).

Davis–Smyth, T., et al., "The second immunoglubulin–like domain of the VEGF tyrosine kinase receptor Flt–1 determines ligand binding and may initiate a signal transduction cascade," *The EMBO Journal* 15:18, 4919–4927 (1996).

Dupont, E., et al., "Antiangiogenic Properties of a Novel Shark Cartilage Extract: Potential Role in th Treatment of Psoriasis," *Journal of Cutaneious Medicine and Surgery*, 2:3, 146–152 (1998).

Dvorak, H.F., et al., "Vascular Permeability Factor/Vascular Endothelial Growth Factor and the Significance of Microvascular Hyperpermeability in Angiogenesis," pp. 98–132.

Fan T., "Controlling the vasculature: angiogenesis, anti–angiogenesis and vascular targeting of gene therapy," *Angiogenesis Review*, 16, 57–66 (1995).

Griffioen, A., et al., "Angiogenesis: Potentials for Pharmacologic Intervention in the Treatment of Cancer, Cardiovascular Diseases, and Chronic Inflammation," *Pharmacological Reviews*, 52:2, 237–268 (2000).

Hanahan, D., et al., "Patterns and Emerging Mechanisms of the Angiogenic Switch during Tumorigenesis," *Cell*, 86:353–364 (1996).

Jackson, J. R., et al., "The codependence of angiogenesis and chronic inflammation," *FASEB J.* 11, 457–465 (1997).

Kerr, J. S., et al., "Novel Small Molecule αv Integrin Antagonists: Comparative Anti–Cancer Efficacy with Known Angiogenesis Inhibitors," *Anticancer Research*, 19:959–968 (1999).

Laue, T.M., et al., *Methods in Enzymology*, 182:566–587 (1990).

Passaniti, A., et al., "Methods in Laboratory Investigation: A Simple, Quantitative Method for Assessing Angiogenesis and Antiangiogenic Agents Using Reconstituted Basement Membrane, Heparin, and Fibroplast Growth Factor," *Laboratory Investigation*, 67:4, 519–528 (1992).

Pluda, J.M., "Tumor–Associated Angiogenesis: Mechanisms, Clinical Impliations, and Therapeutic Strategies," *Seminars in Oncology*, 24:2,202–218 (1997).

Raju, K. S., et al., "Characterization of a chemoattractant for endothelium induced by angiogenesis effectors," *Cancer Res.*, 44(4):1579–84 (1984).

Rak, J., et al., "Treating cancer by inhibiting angiogenesis: new hopes and potential pitfalls," *Cancer and Metastasis Reviews* 15:231–236 (1996).

Sauder, D. N., et al., "Angiogenesis in Dermatology," *Curr Prob Dermacol*, 1–10 (2001).

Siemeister, G., et al., "Two Independent Mechanisms Essential for Tumor Angiogenesis: Inhibition of Human Melanoma Xenograft Growth by Interfering with either the Vascular Endothelial Growth Factor Receptor Pathway or the Tie–2 Pathway," *Cancer Research* 59, 3185–3191 (1999).

Takano, S., et al., "Concentration of Vascular Endothelial Growth Factor in the Serum and Tumor Tissue of Brain Tumor Patients," *Cancer Research* 56, 2185–2190 (1996).

Weber, G., "Biochemical Strategy of Cancer Cells and the Design of Chemotherapy: G.H.A. Clowes Memorial Lecture," *Cancer Research*, 43:3466–3492 (1983).

Auerbach, W., et al., *Pharmac. Ther.* 63:265–311 (1994).

Bischoff, J., *Trend Cell Biol.*, 5:69–74 (1995).

Brooks, P.C., *Cancer Metastasis Rev.*, 15:187–194 (1996).

Brooks, P.C., *Eur. J. Cancer*, 32A:2423–9 (1996).

Bussolino, F., et al., *Eur. J. Cancer*, 32A:2401–12 (1996).

Ferrara, N., *Nature*, 376–467 (1995).

Ferrara, N., et al., *Endocrine Rev.*, 18:4–25 (1997).

Form, D., et al., *J. Cell Physiol.*, 152:196–205 (1992).

Hamada, J., et al., *Br. J. Cancer*, 66:349–354 (1992).

Hanson, et al., *J. Bone & Min. Res.*, 7:1251–1258 (1992).

Ingber, *Sem. Cancer Biol.*, 3:57–63 (1992).

Jaffe, et al., *J. of Clin. Invest.*, 52:2745–2756 (1973).

Klagsbrun, M., et al., *Annu. Rev. Physiol.*, 53:217–32 (1991).

Klein, S., et al., *Mol. Biol. CelL.*, 4:973–82 (1993).

Klein, S., et al., *J. Biol. Chem.*, 271:22583–90 (1996).

Knight, et al., *FEBS Let.*, 296, 263–266 (1992).

Knighton, D.R., et al., *Science*, 221:1283–85 (1983).

Koch, A.E., et al., *Nature*, 376:517–19 (1995).

Laemmli, U.K., *Nature*, 227:680 (1970).

Mazure, N.M., et al., *Cancer Res.*, 56:3436–40 (1996).

Mignatti, P., et al., *J. Cell. Biol.*, 113:1193–201 (1994).

Moses, M.A., et al., *Int. Rev. Cytol.*, 161:1–48 (1995).

Pepper, M.S., et al., *J. Cell Physiol.*, 152:196–205 (1992).

Pepper, M.S., et al., *Biochem. Biophys. Res. Commun.*, 189:824–31 (1992).

Polverini, P.J., et al., *Eur. J. Cancer*, 32A:2430–7 (1996).

Proost, P., et al., *Int. J. Clin. Lab. Res.*, 26:211–23 (1996).

Rak, J., et al., *Eur. J. Cancer*, 32A:2438–50 (1996).

Rak, J., et al., *J. Cell. Physiol.*, 159:245–55 (1994).

Rosen, et al., *Medical Hypotheses*, 6:448–53 (1997).

Sander, P., et al., *Kidney Int.*, 51:448–53 (1997).

Schwartz, S.M., et al., *J. Cardovasc. Pharmacol.*, 21 sUPPL:1:S31–S49 (1993).

Schweigerer, L., et al., *Nature*, 325:258–9 (1987).

Welgus, et al., *J. Biol. Chem.*, 256:9511–9516 (1979).

Wilkin, J.K., *Arch. Dermatol.*, vol. 130, 359–362 (1994).

\* cited by examiner

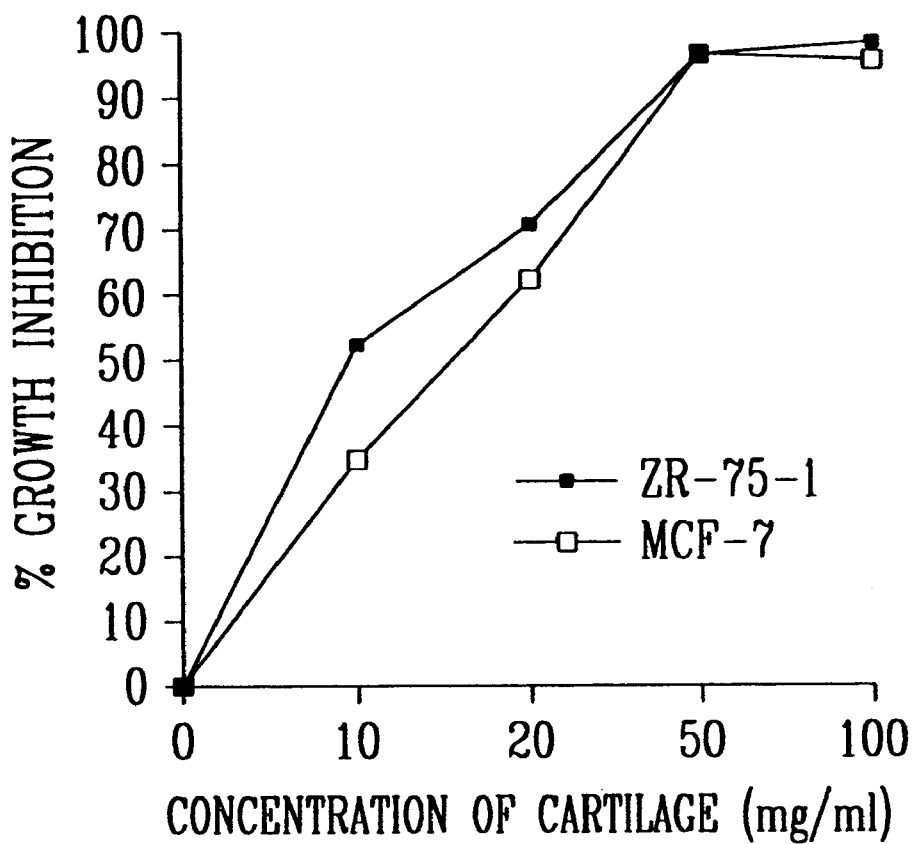
FIG_2

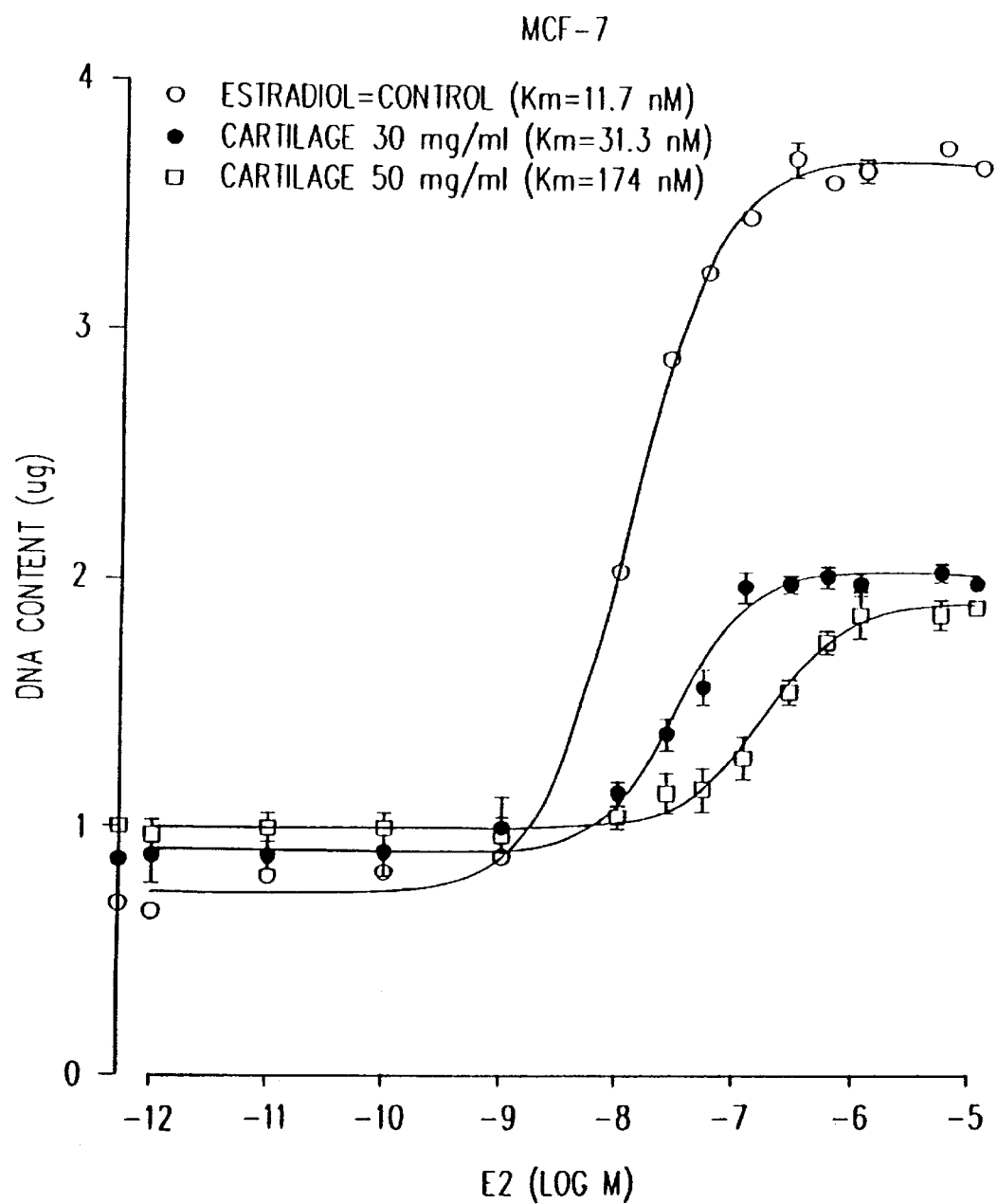

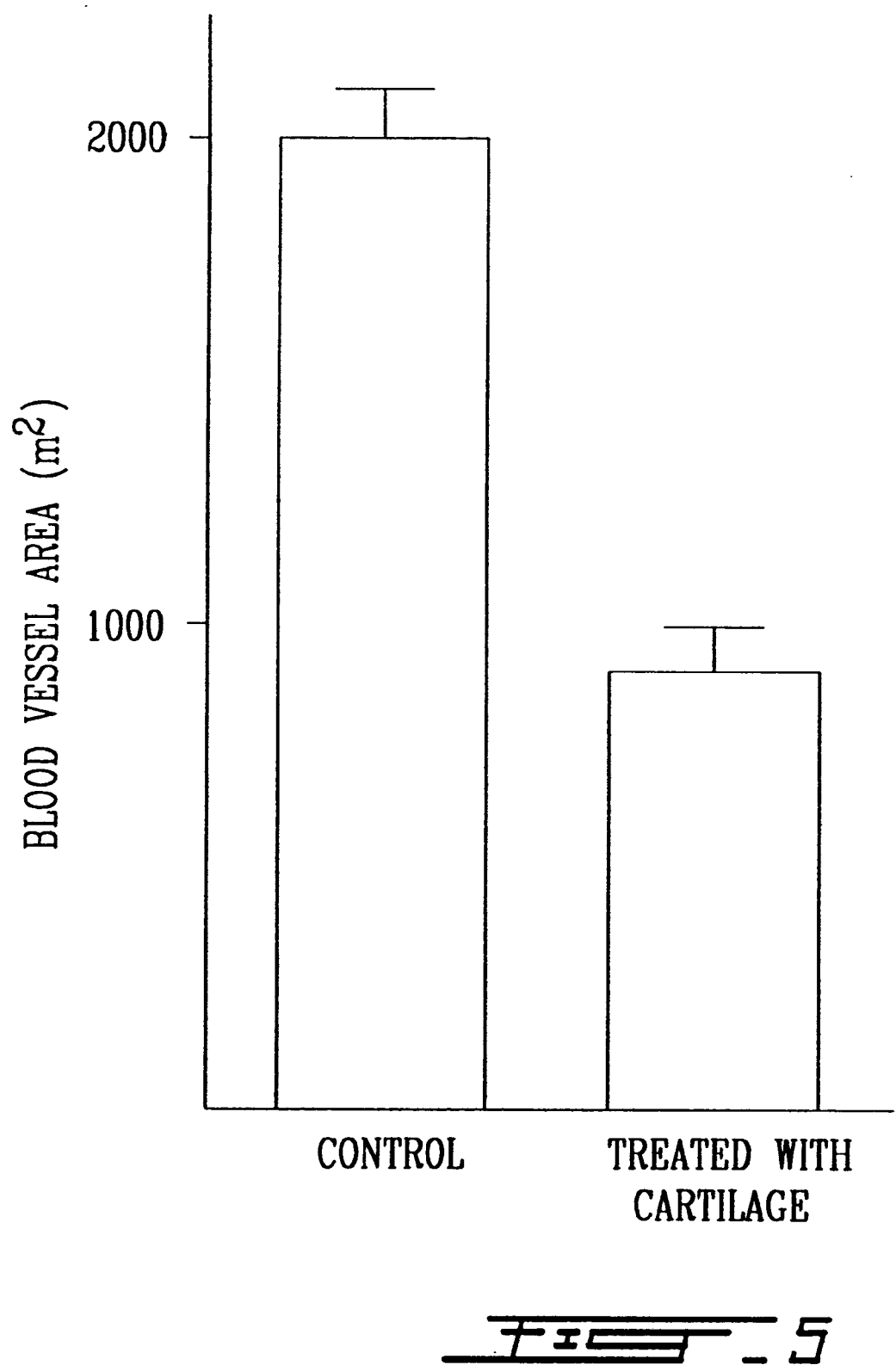
FIG_5

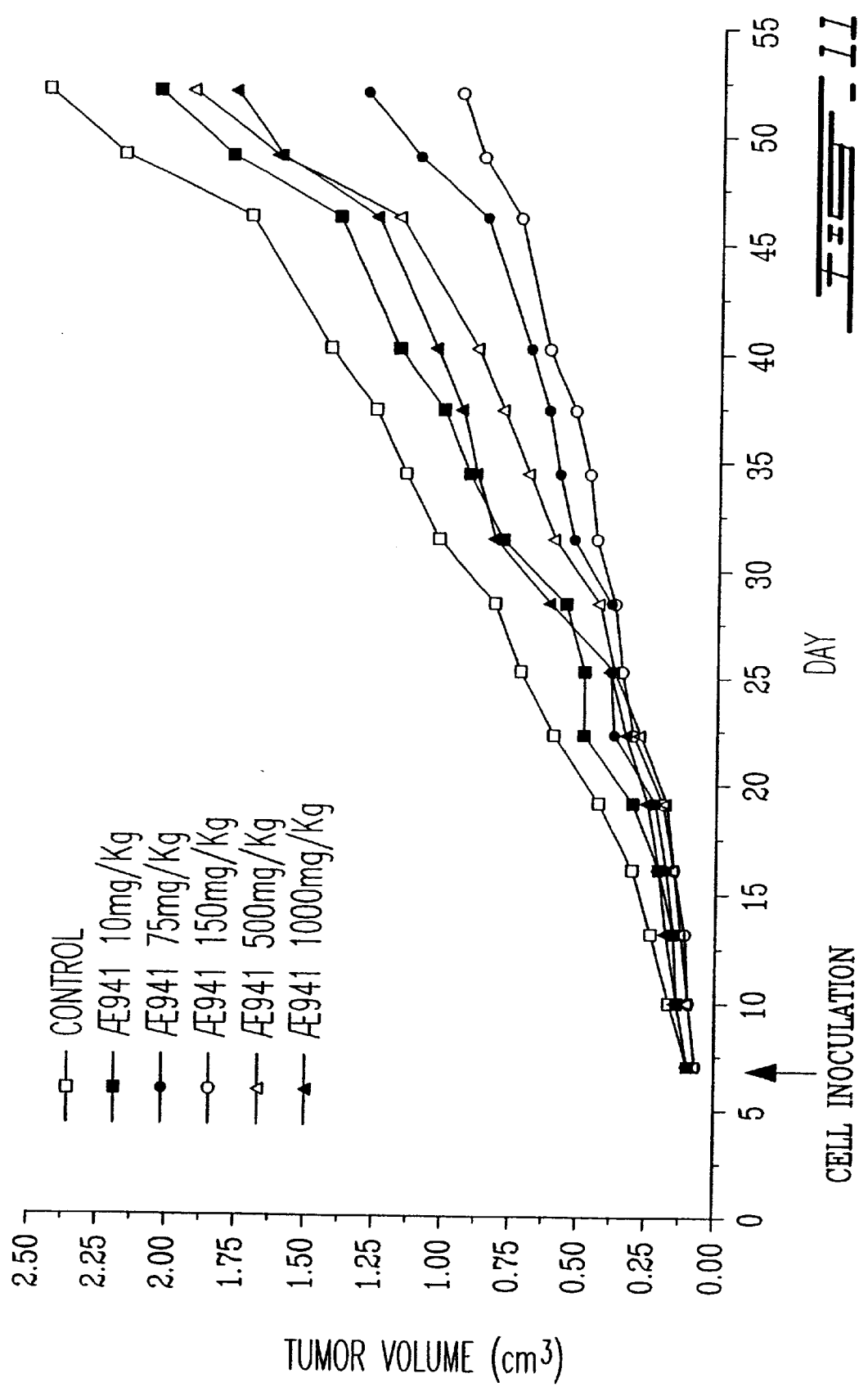

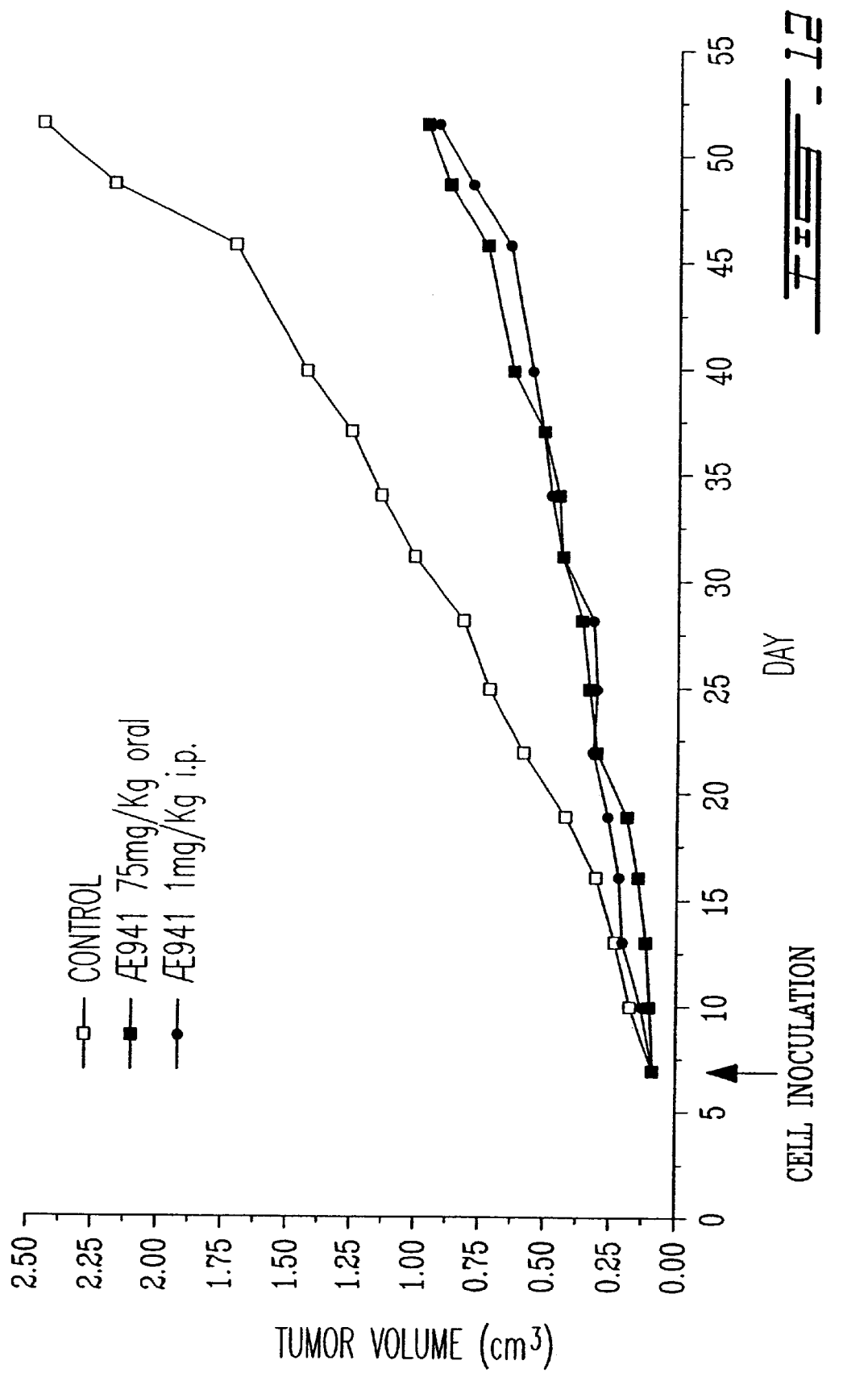

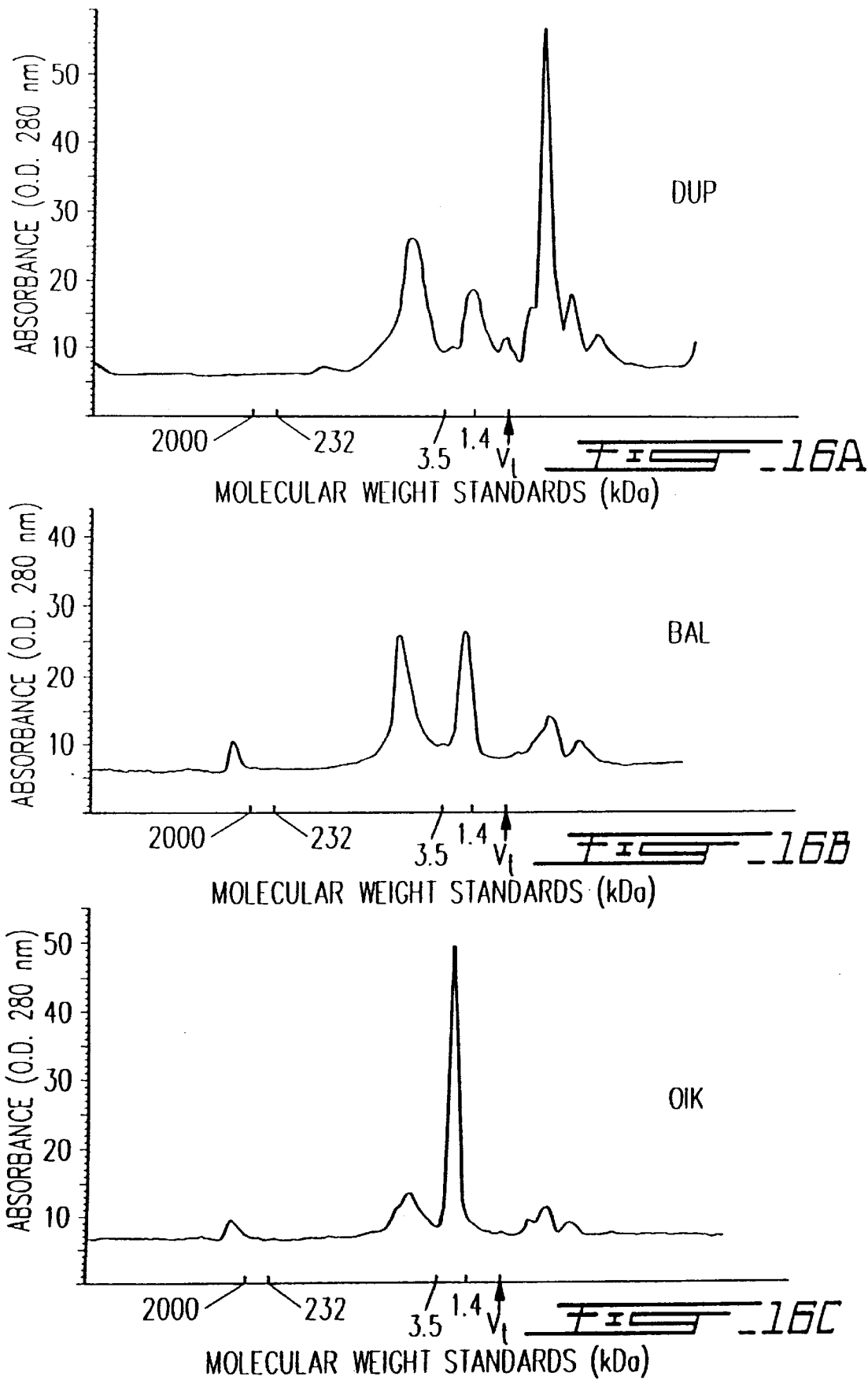

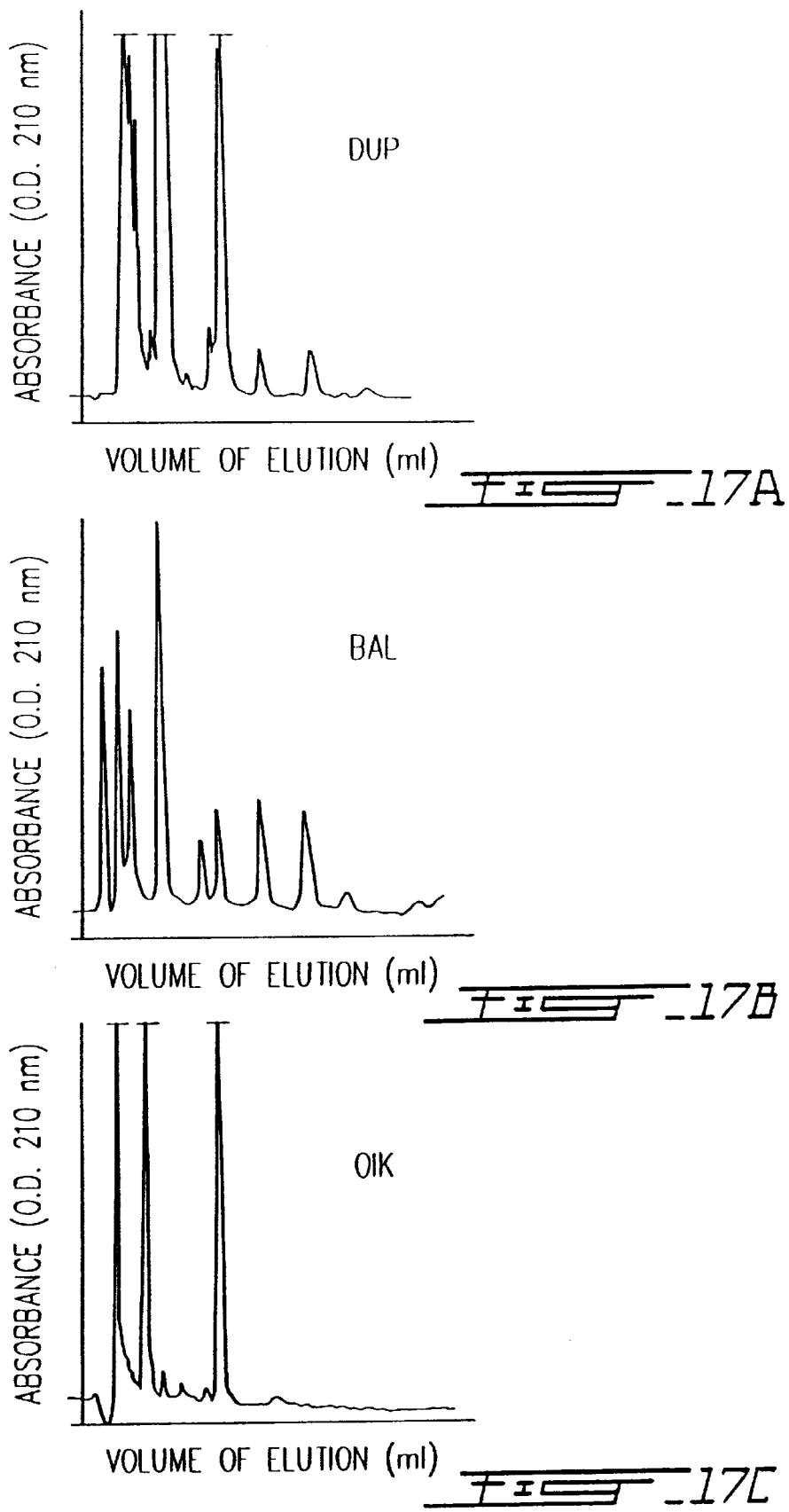

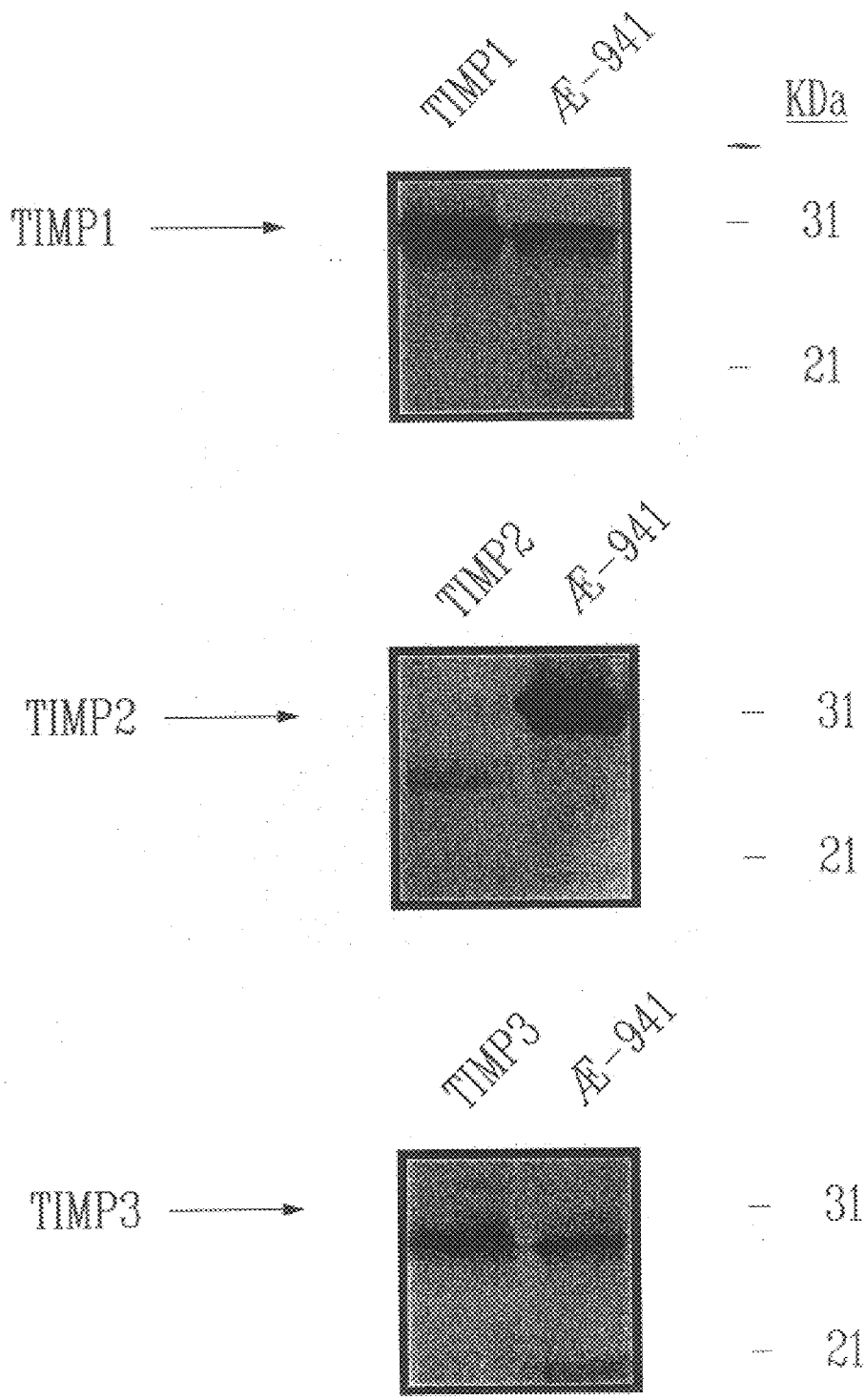

SHARK CARTILAGE EXTRACT: PROCESS OF MAKING, METHODS OF USING, AND COMPOSITIONS THEREOF

CROSS-REFERENCE TO RELATED APPLICATIONS

This application is a divisional of U.S. patent application Ser. No. 09/504,065, filed Feb. 15, 2000, now U.S. Pat. No. 6,380,366; which is a continuation-in-part of U.S. patent application Ser. No. 08/693,535, filed Aug. 8, 1996, now U.S. Pat. No. 6,028,118; which is in turn a continuation-in-part of U.S. patent application Ser. No. 08/550,003, filed Oct. 30, 1995, now U.S. Pat. No. 6,025,334; which is in turn a continuation-in-part of U.S. patent application Ser. No. 08/384,555, filed Feb. 3, 1995, now U.S. Pat. No. 5,618,925; which is a continuation-in-part of U.S. patent application Ser. No. 08/234,019, filed on Apr. 28, 1994, now abandoned.

BACKGROUND OF THE INVENTION

Cartilage is a/n avascularized tissue and has been studied as a potential candidate containing anti-angiogenic factors. It is also a tissue that is relatively resistant to tumor development. The tumor associated with cartilage, chondrosarcoma, is the least vascularized of solid tumors. Angiogenesis is one of the important factors in the development of a tumor. Discrete solid tumor masses appear if the tumor cells can provoke the adjacent vascular network to expand in order to supply their nutritional needs. The factors involved in the stimulation of angiogenesis have been studied for their role in the development of tumor and anti-angiogenic factors. Drugs having an angiogenic inhibitory activity have been also investigated as tools for controlling the growth or for effecting regression of tumors.

It has been discovered that scapular cartilage in calves contains a substance that inhibits the vascularization of solid tumors (Langer et al. (1976) *Science.* 193: 70–72). Because of its encouraging potential as anti-tumor agent, sources of greater supplier of cartilage have been looked for.

Sharks are a potential source of this kind of angiogenesis inhibitor because their endoskeleton is composed entirely of cartilage (6% of their body weight versus 0.6% in calves). Sharks have a low propensity for tumor development. Many hypotheses have been elaborated to explain this low probability of developing tumors in sharks. It has been shown inter alia that IgM antibodies able to readily attack any aggressing agent, or that macrophages capable of differentiating normal cells from neoplastic cells and of destroying the latter. Rosen and Woodhead (1980) in *Medical Hypotheses.* 6:441–446 have postulated that the rarity of tumors in elasmobranchs (a subclass to which sharks and rays belong) might be due to the high ionic strength of their tissues, which is equivalent to a high body temperature. In these conditions, these authors believe that the immune system exerts a close to 100% immunological surveillance. It has also been discovered that sharks produce an aminosterol having antibacterial and antiprotozoal properties.

Finally, Lee and Langer (1983) in *Science* 221: 1185–1187 and Folkman and Klagsbrun (1987) in *Science.* 235: 442–447 have shown that sharks produce a substance that inhibits neovascularization. Lee and Langer (op. cit.) have isolated this substance by extracting it from shark cartilage in denaturing conditions (guanidine extraction). This process of extraction is however very long (41 days), and the yield of active components is far from excellent. While the active substance isolated from calves has a molecular weight of about 16 kilodaltons (kDa), the same group of researchers has not given a precise molecular weight to the one isolated from sharks. This substance is only defined has having a molecular weight higher than 3500 Daltons.

Oikawa et al. (1990) in A Novel Angiogenic Inhibitor Derived from Japanese Shark Cartilage (I). Extraction and Estimation of Inhibitory Activities Toward Tumor and Embryonic Angiogenesis (*Cancer Letters* 51: 181–186) have applied the same method of extraction as the one described by Lee and Langer, but of a much shorter duration (2 days instead of 41 days). The anti-angiogenic substance isolated from shark cartilage by Oikawa et al. is restricted to a molecule having a molecular weight ranging from 1000 to 10,000 Daltons. Schinitsky (U.S. Pat. No. 4,473,551) has described a water extract of crude powdered shark cartilage which fraction of more than 100,000 Daltons has an anti-inflammatory activity, especially in combination with glucosamine. No suggestion of a component of this extract having an anti-angiogenic or anti-tumor activity is made in this patent.

Kuetner et al. (U.S. Pat. No. 4,746,729) have isolated a olymorphonuclear neutrophil (PMN) elastase inhibitor from bovine cartilage. This inhibitor has been obtained from an aqueous extract of cartilage from which molecules of a molecular weight of less than 50,000 Daltons have been retained. Fractionation on Sephacryl S-200 has given numerous fractions from which those of 10–40 kDa have been pooled after they have demonstrated an anti-elastase activity. The active component has an isoelectric point of 9.5 and might have a molecular weight of about 15,000 Daltons. Kuetner et al. (U.S. Pat. No. 4,042,457) have also shown that bovine cartilage has a component of a molecular weight of less than 50,000 Daltons which has a cell proliferation inhibitory activity without any activity on endothelial cell growth. Balassa et al. (U.S. Pat. No. 4,822,607) have obtained a cartilage extract in an aqueous solution, which extract has an anti-tumor activity. However, we have observed no anti-angiogenic activity in an extract obtained by reproducing Balassa's method. Spilburg et al. (U.S. Pat. No. 4,243,582) have isolated two glycoproteins of molecular weight of 65 kDa and of isoelectric point of 3.8 from bovine cartilage (guanidine-extraction) which show anti-trypsin activity and an endothelial cell growth inhibitory activity.

Calf and shark cartilage contain many biological activities such as pro-inflammatory activity, anti-inflammatory activity, anti-angiogenic activity, lysozyme activity, cell growth-promoting activity, inhibitory activity against types I and IV collagenase, elastase, and other proteases like trypsin, chymotrypsin and plasmin. However, nobody has yet obtained a cartilage extract that comprises a pool of clinically valuable activities, and particularly with new activities.

Shark cartilage anti-angiogenic component(s) have been generally tested in rabbit corneal pocket assay or in chick chorioallantoic membrane (CAM) assay. Up to date, whole powdered cartilage has been tested directly on tumors in vivo, on human melanoma xenograft implanted in nude mice (U.S. Pat. No. 5,075,112), as well as tested in CAM tests for its anti-angiogenic effect. Even though an anti-tumor effect has been assigned to cartilage extracts, this effect has most often been attributed to the anti-angiogenic component that deprives the tumor of blood supply. Up to now, there is no evidence in the art that a shark cartilage has a direct effect on tumor cell proliferation.

A few methods of obtaining shark cartilage extracts and fractions are already known. Some of them produce a powdered crude cartilage without any extraction (U.S. Pat. No. 5,075,112). Others use denaturing or chaotropic agents like guanidine (U.S. Pat. No. 4,243,582). Others perform a pre-treatment of cartilage by way of an enzymatic digestion to get rid of any muscular, nervous or vascular structures surrounding the cartilage, which pre-treatment step is followed by the elimination of fats in organic solvents, and then the active components are extracted in an aqueous phase. (Balassa et al., U.S. Pat. Nos. 3,478,146; 4,350,682; 4,656,137; and 4,822,607). The effect of such pre-treatment on the preservation of the integrity of the biologically active cartilage components is not known. If too extensive, an enzyme digestion may hydrolyze active protein components. For example, Balassa's method (U.S. Pat. No. 4,822,607) produces a liquid extract without anti-angiogenic activity; this loss may be the result of such enzymatic degradation, or else, the anti-angiogenic is masked or antagonized by other molecules. Balassa's method does not include a fractionation step which would further enrich an extract in active components, and which may remove undesirable molecules. Others simply produce aqueous extracts (in water (U.S. Pat. No. 4,473,551) or salt solutions (U.S. Pat. No. 4,746,729) of cartilage by eliminating the unsolubilized material. Among the latter, specific fractions of specific molecular weights have been particularly retained for further study and purification (see discussion above). There is no process in the art that leads to the preparation of a cartilage extract having substantially all the hydrosoluble active components of cartilage.

Moreover, the methods of the prior art are too lengthy to be of a practical purpose and they do not necessarily yield sufficient amounts of active components. Amongst the recovered components, some are not recovered at all or in insufficient yield to show detectable activity or some have been disregarded by focusing on the preparation of one specific component having one activity.

Angiogenesis is not only involved in cancer development. Many diseases or conditions affecting different physiological systems (indicated in parentheses) are angiogenesis-dependent among which the following examples: arthritis and atherosclerotic plaques (bone and ligaments), diabetic retinopathy, neovascular glaucoma, macular degeneration, ocular herpes, trachoma and corneal graft neovascularization (eye), psoriasis, scleroderma, rosacea, hemangioma and hypertrophic scarring (skin), vascular adhesions and angiofibroma (blood system). Therefore, any new and potent anti-angiogenic "factor" could find an use in the treatment of these diseases as well as in cancer therapy and other angiogeno-dependent diseases. Moreover, since many of the above-mentioned diseases and conditions also have an inflammatory etiological component, any new and potent anti-inflammatory "factor" or component could find a use in the treatment of these diseases and conditions as well as of any other inflammatory diseases or conditions. Furthermore, since metalloproteases like collagenases are involved in a diversity of diseases and conditions like cancer, inflammation and premature ageing of the skin (collagen degrading activity), a new and potent anti-collagenolytic "factor" could be useful in the treatment of diseases or conditions having a collagenolytic or a matrix metalloprotease etiological component. Because angiogenesis, inflammation and proteolysis may be encountered alone or in combination in a large variety of diseases or conditions, a product capable of antagonizing at least all these activities without affecting normal body functions would be of a great therapeutic value. Furthermore, a product which would have a direct anti-tumor activity would also have a significant therapeutic value.

BRIEF SUMMARY OF THE INVENTION

The present invention provides a new method of producing cartilage extracts which has the advantage of containing a plurality of therapeutically valuable activities. Amongst those, anti-angiogenic, anti-inflammatory, anti-collagenolytic, in vivo anti-tumor proliferating and direct in vitro anti-tumor proliferating activities have been confirmed to be present in satisfying concentrations in a cartilage extract obtained from shark. All activities have been obtained in a liquid extract of shark cartilage, and some of them have been obtained or verified as being present in a solid extract of the same.

The present invention relates to a new method of preparing a fractionated cartilage extract comprising water soluble biologically active components, the majority of which have a molecular weight of less than about 500 kDa. The method comprises the step of:

first fractionating a crude cartilage extract comprising water-soluble biologically active components obtained from cartilage material, such that a major portion of the biologically active components having a molecular weight of greater than about 500 kDa are separated from a major portion of biologically active components having a molecular weight of less than about 500 kDa to form a first fractionated cartilage extract.

A first fractionated cartilage extract that has been obtained from shark cartilage is referred to herein below as a "cartilage extract." The term fractionated will be omitted, even though the cartilage extract has been fractionated to remove molecules heavier than about 500 kDa.

This method has the advantage of being easy to perform and efficient. High yields of cartilage extract have been obtained, which extract, particularly obtained from fresh or frozen/thawed shark cartilage, contains at least all the above-mentioned biological activities. Other sources of cartilage can be used in this process. It is preferably performed at cold, cool or ambient temperatures (about 0° to 20° C., although the biologically active components can withstand temperatures as high as about 40° C.), in non-denaturing conditions (preferably, the extraction medium is an aqueous solution or pure water), at a near neutral pH (about 5 to 8) to maximize the probability of recovering compounds of a priori unknown physio-chemical characteristics.

According to this process, cartilage components can be extracted in a low volume of solution (as low as 1 L for 1 kg of cartilage). Homogenization of cartilage may be performed for a short period of time (as short as 10 to 20 minutes). Homogenization and extraction in the extraction medium results in the formation of particles and a crude extract which are separated by mechanical and physical means. The crude extract is then fractionated to remove molecules having a molecular weight higher than 500 kDa. A liquid extract is the fractionated extract comprising water-soluble biologically active components having a molecular weight less than about 500 kDa. In one embodiment, the solid extract comprises the insoluble particles separated from the liquid extract. In another embodiment, the solid extract is a dried form of the liquid extract. Homogenization reduces the size of cartilage particles and thereby maximizes the extractable surface area of the cartilage. Other known ways of reducing the particle size of solids, in particular cartilage, may be used, as long as a major portion of the biologically active components being extracted are preserved and remain extractable.

This invention relates to cartilage extracts, particularly to extracts from elasmobranch species, more particularly shark. The solid extract has shown activity. It may contain collagen and non-hydrosoluble components. It may also contain a residual activity of what was extracted in the cartilage extract. The cartilage extract is very rich in activities. It can be used as such or it can be concentrated. A concentration step which favors the maintenance of biological activities is conducted. Ultrafiltration on a membrane having a nominal molecular weight cut-off value of about 1 kDa has been used to concentrate the cartilage extract of this invention. Nanofiltration on a membrane having a nominal molecular weight cut-off value of about 100 Daltons should even be better to concentrate the biological activities of the cartilage extract, preventing the loss of any activity assigned to very small molecules. Finally, concentration by evaporation or lyophilization can also be performed, in so far as such treatment does not substantially reduce the activity of the extract. Stabilizers may be used to protect the cartilage extract to minimize loss of activity during lyophilization.

The cartilage extract (<500 kDa) has been further fractionated to characterize the active components thereof. Active fractions have been obtained by performing additional fractionation steps. Some fractions tested for their anti-tumor activity on tumor cell lines have been grossly characterized by their molecular weight and isoelectric point. Others have been assigned an activity, particularly anti-collagenolytic, anti-metalloproteasic or anti-angiogenic. Therefore, valuable activities are recovered in cartilage extract and fractions thereof, which may be advantageously used. In lieu of administering high amounts of powdered cartilage, a more acceptable and enriched extract may now be administered.

The present invention also relates to any therapeutic or cosmetic compositions comprising as an active ingredient an effective amount of a concentrated or dilute cartilage extract preferably obtained from shark. These compositions are generally used in dermatological or cosmetic formulations due to the observed activities of the cartilage extract. In this respect, the observed anti-angiogenic, anti-metalloproteasic and anti-inflammatory activities, and the antagonistic effect of cellular differentiation mediated by the protein kinase C signal transduction pathways in keratinocytes, and the antagonistic effect on VEGF (vascular endothelium growth factor) activity, are all considered as possible mechanisms upon which new uses of the shark cartilage extract can be developed.

The invention also provides a method of treating a variety of mammalian skin diseases or disorders including, for example, Reiter's syndrome, pityriasis rosea, lichen planus, pityriasis rubra pilaris, secondary syphilis, mycosis fungoides, ichthyosiform eruptions, sclerodermia, hyperthrophic scar, papulosquamous disease, psoriasis, rosacea, eczema and acne. Preferred embodiments of the invention provide the following:

1) a method for inhibiting angiogenesis in mammalian skin;
2) a method for reducing telangiectesia in mammalian skin;
3) a method for reducing spider veins or varicose veins in mammalian skin;
4) a method for inhibiting endothelial cell proliferation in mammalian skin;
5) a method for treating cancer in mammalian skin, particularly a melanoma;
6) a method for decreasing the expression of rosacea in mammalian skin;
7) a method for reducing papulosquamous skin disease in mammalian;
8) a method for reducing the appearance of peri-orbital dark circles in mammalian;
9) a method for reducing inflammation in mammalian, be it caused by a chemical irritant, a physical abrasion, U.V. radiation, an allergen or an infectious agent;
10) a method for soothing irritated skin in mammalian;
11) a method for inhibiting activated-keratinocyte differentiation in mammalian skin;
12) a method for reducing acne in mammalian skin;
13) a method for decreasing the expression of eczema in mammalian skin;
14) a method for inhibiting metalloprotease activity in mammalian skin;
15) a method for treating warts in mammalian;
16) a method for enhancing wound repair in mammalian;
17) a method for enhancing skin barrier function in mammalian;
18) a method for regulating wrinkles and atrophy in mammalian skin; and
19) a method for retarding premature aging in mammalian skin.

A plurality of diseases or disorders having simple or complex etiologies will benefit from treatment with the present cartilage extract. Other medical fields of use, including but not limited to dermatological use, are within the scope of this invention. Dermatological diseases or disorders that have up to date been difficult to treat with actual short and long term therapies because of their complex etiology, are susceptible to treatment with the cartilage extract of this invention. Furthermore, since the cartilage extract has been successfully tested in a variety of cancers, arthritis, psoriasis, rosacea, and acne cases, compositions and methods for treating diseases, conditions or disorders having one or more etiological components selected from tumor proliferation, angiogenesis, inflammation and metalloprotease activity such as collagenolysis, are within the scope of this invention, without any limitation as to the dosage form, the route of administration way and the tissue to be treated.

BRIEF DESCRIPTION OF THE SEVERAL VIEWS OF THE DRAWINGS

The present invention will be more readily understood by way of the specific embodiments shown in the appended figures which various embodiments of the invention.

In the drawings:

FIG. 2 shows a dose-response inhibitory activity of shark cartilage (solid) extract on ZR75-1 and MCF-7 cell lines.

FIG. 3 illustrates dose-response curves of MCF-7 cells in the presence of increasing concentrations of estradiol with or without two concentrations of solid cartilage extract.

FIG. 5 show that the vascularization of the mammary gland and tumor in cartilage-treated rats is decreased by 50%.

FIG. 11 shows the effect of various doses of liquid cartilage extract on tumor growth inhibition in mice.

FIG. 12 shows that intraperitoneal administration of the liquid cartilage extract can significantly increase the efficacy of liquid cartilage to inhibit tumor growth.

FIG. 16 shows a FPLC migration pattern of three different extracts of shark cartilage. In panel A, DUP stands for a liquid cartilage extract according to this invention. In panels B and C, BAL and OIK stand for extracts of the prior art, Balassa et al. and Oikawa et al., respectively.

FIG. 17 shows a HPLC migration pattern of the same extracts defined in FIG. 16.

FIG. 32 shows an immunoblot of the cartilage extract revealed with anti-TIMP antibodies. Five µg of TIMP-1, TIMP-2 and TIMP-3 proteins and 35 µg of the liquid cartilage extract proteins were subjected to SDS-PAGE and blotted using respective specific anti-TIMP antibodies coupled to horseradish peroxidase.

DETAILED DESCRIPTION OF THE INVENTION

Figure 1:
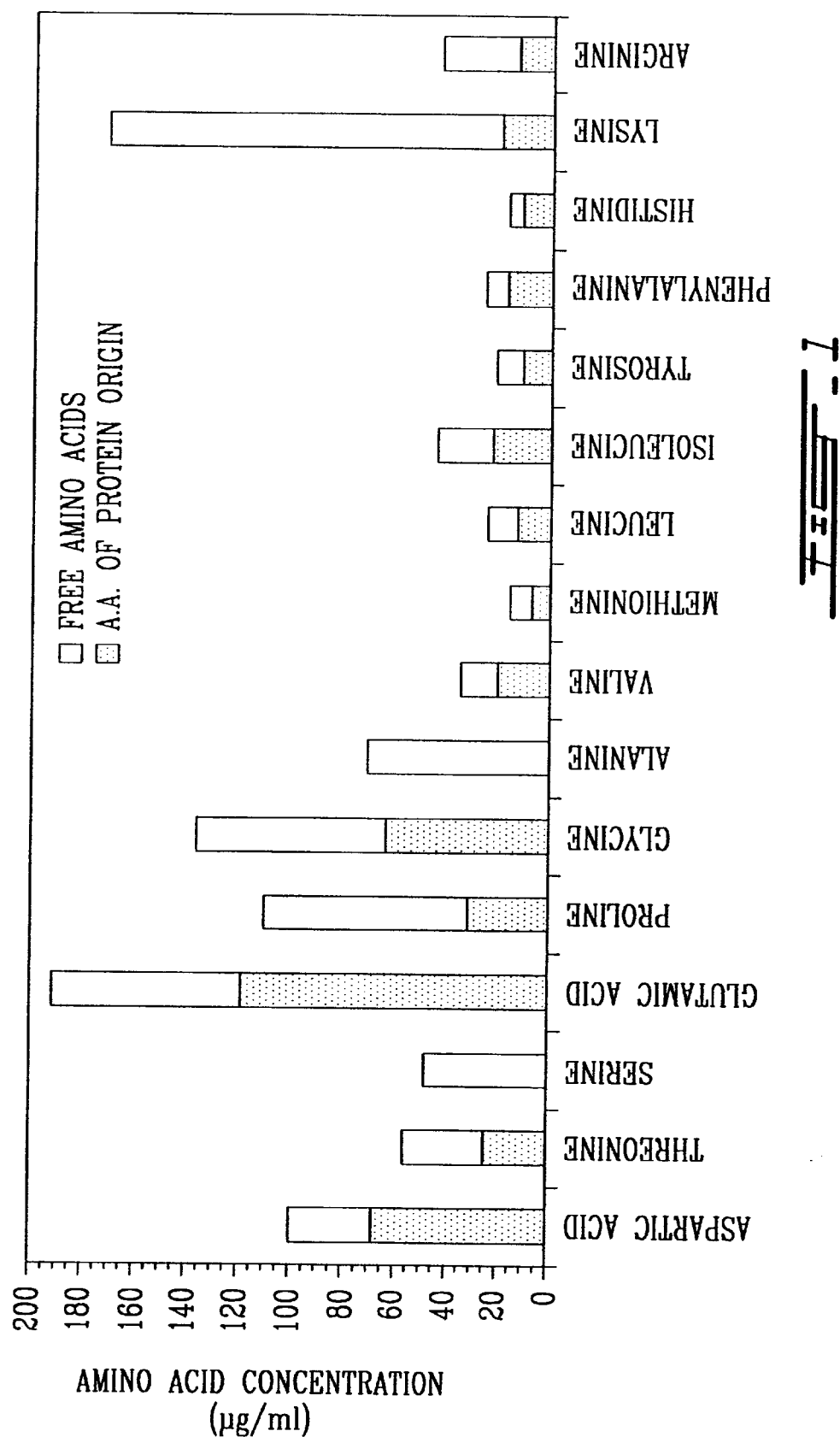
FIG. 1 shows the specific amino acid composition of the cartilage extract (liquid).

In a specific embodiment, cartilage has been obtained from healthy small coastal sharks (Dog Fish, smooth hound). Any muscular and connective tissue has been removed by scraping with ethanol-treated scalpels and scissors. The cartilage was then vacuum-packed in plastic bags and frozen to −20° C. for further use. Any source of cartilage may be used in the present invention. It is believed that cartilage from any elasmobranch species (which includes sharks and rays as species of this subclass), will provide about equivalent products. The cartilage extract prepared herein may differ in its nature and concentration of biologically active components obtained by the present process when compared to an extract of a mammalian source of cartilage.

Any variation in the preparation of cartilage prior to its extraction may be used as long as it does not substantially affect the activity of the product of interest (a cartilage extract or a particular sub-fraction thereof, for example). Some active components may be resistant to the proteolytic digestion used by Balassa et al. (U.S. Pat. No. 4,822,607) to rid the cartilage of surrounding tissues, while others may not be stable to such treatment. Therefore, if one wants to produce a liquid extract containing as much as possible of all the hydrosoluble active components described herein, such a digestion step during the extraction procedure should be avoided or carefully monitored to prevent extensive hydrolysis or proteolysis.

Preparation of Cartilage Extracts

Clean cartilage was used fresh, thawed to 4° C., or frozen. Cartilage was then passed numerous times (more particularly three times) through the pores of an ethanol-aseptized meat chopper together with an adequate volume of water (an equal quantity (weight/volume) is about a minimal volume but can be increased without bearing any deleterious effect on the yield of recovery of valuable components). A low volume is preferred since it is more convenient to manipulate than unnecessary high volumes, from a practical point of view. In the practice, water has been purified by inverse osmosis and multiple filtrations down to 0.1 μm filter. Many aqueous solutions (containing salts, for example) could be used in lieu of water. When recovery of a plurality of hydrosoluble activities is contemplated, working at a near neutral pH (5.0 to 8.0) and non-denaturing conditions is preferred to avoid lysis or denaturation of some of the cartilage active components. The behavior of unknown proteins in aqueous solvents is not predictable; some may be more stable in an acidic pH, some at a basic pH. Furthermore, some proteins may be extractable in mild denaturing conditions, if such denaturation does not irreversibly affect the renaturation of these proteins in aqueous solutions. For the sake of clarity, any extraction medium that is compatible with the preservation of biologically active hydrosoluble cartilage component is within the scope of this invention. Therefore, performing the extraction in pure water is preferred. Other preferred embodiments include those wherein salts and/or chaotropic agents are added to the water prior to or during extraction.

The cartilage/water mixture was then homogenized at maximum speed in a kitchen blender at about 4 to 20° C. for about 20 minutes. During homogenization, the temperature may be as high as about 40° C. The speed of the agitation as well as the volume of aqueous solution may influence both time and yield of extraction. The homogenization (to yield particle size of less than 500 μm particles) may last from 10 minutes to as 24 hours, preferably between about 10 and 60 minutes.

Liquefaction of this homogenate is performed by disintegration with a Polytron disintegrator for about 10 minutes at about 4° C. to 20° C., if the blender did not sufficiently reduce the size of the particles. Alternatively, the cartilage/water mixture is simply homogenized in a higher performance blender-disintegrator which, in our hands, saved 10 min in the liquefaction step. Upon completion of the homogenization step, the average residual particle size is preferably less than about 500 μm. The size of the particles after homogenization does not need to be ultra small, although a very small size should increase extraction efficiency. Indeed, pulverization of cartilage in the form of a powder before aqueous extraction may be used to reduce size particles prior to extraction, in so far as this does not denature valuable activities. In our process, homogenization of cartilage allows size reduction and extraction of active components to occur almost simultaneously.

The homogenate, which is a mixture of particles and of a crude extract, was centrifuged at 13,600× g during 15 minutes at about 4° C. to 20° C., which step is one way to separate quickly and efficiently a supernatant from a pellet. Variation and adjustment of these parameters are well within the knowledge of the skilled artisan, merely depending on the volume of homogenate and of the equipment used.

The resulting pellet was lyophilized for 24 to 48 hours. This first fraction will hereinbelow be defined as the lyophilizate or "solid extract."

The supernatant can be filtered on a 24 μm Whatman filter, if necessary, to get rid of particles susceptible to affect the performance of an ultrafiltration column. The filtered material was then separated into fractions. Separation may be achieved by different methods and separation media including but not limited to:

Chromatography: (adsorption, ionic exchange, gel filtration)
Electrophoresis
Ultrafiltration
Ultra centrifugation with zonal density gradients, and
Adsorption extraction.

In a specific embodiment, the crude extract was ultrafiltered at about 4° C. to 20° C. (although temperature could increase to about 40° C.) on a tangential flow filtration column having a membrane of a porosity of about 500 kDa, which allowed a first fractionated extract to be obtained, comprising hydrosoluble molecules of a molecular weight comprised between 0 and about 500 kDa. This fractionated extract was filtered on 0.22 μm filter, and aliquoted in aseptic bottles for further use. This fraction will be further referred to as the "first fractionated extract" or "cartilage extract" or the "liquid extract."

An alternative, higher performing centrifuging procedure has been developed to obtain the pellet and the supernatant. The step of centrifuging at 13600× g for 15 minutes followed by a gross filtration on Whatman filters has been replaced by a centrifugation in a CEPA centrifuge equipped with a nylon pocket of a porosity of 1 μm, at 3000–4000×g. A 25 kg/25 L preparation can be centrifuged in that manner within 30 minutes and provide about 29 liters of supernatant. The aqueous volume obtained is higher than the starting volume of water, suggesting that a part of the water content of the cartilage itself has been harvested. The solids recovered upon centrifugation and referred to as the "solid extract" were optionally lyophilized. In one example, the solid and liquid extracts had the following approximate composition which grossly takes into account the variations observed from batch to batch, and when using different material:

| Solid Extract: | |
| --- | --- |
| Lipids | 7.35%[1] |
| Proteins | 46.2%[2] |
| Humidity | 20.4% |
| Sodium | 4.16 mg/g[3] |
| Potassium | 2.64 mg/g |
| Calcium | 114 mg/g |
| Magnesium | 1.49 mg/g |
| Zinc and iron | traces |
| Liquid Extract: | |
| Lipids | 0.10–0.20%[1] |
| Proteins | 8–25 mg/ml[2] |
| Dry weight | 8–25 mg/ml |
| Humidity | 97–99% |
| Sodium | 30–220 mg/100 g[3] |
| Potassium | 30–40 mg/100 g |
| Calcium | 2.0 mg/100 g |
| Magnesium | 1.1 mg/100 g |
| Zinc and iron | traces |

[1,2]Measured following directives published in AOAC Official (1984) sections 16.219–220 and 2.055, respectively.
[3]Measured following the SAA procedure.

The protein content is evaluated by the Kjeldahl method, which indeed measures organic nitrogen (N). Organic nitrogen is converted to equivalent protein by using the following equation:

$$\text{Proteic content (mg/ml)} = \frac{(\% N \times 6.25)}{100}$$

Carbohydrate content was not determined, but carbohydrates were assumed to be present in the form of proteoglycans and/or mucopolysaccharides. It is possible that these compounds are included in the measured level of humidity. The solid extract contains an unexpected level of humidity which was measured by the OH groups to be about 20% water content, which is close to the percentage of carbohydrates normally retrieved in cartilage.

The (liquid) cartilage extract was analyzed for its amino acid content. The average amount of total amino acids was approximately 1.1 mg per ml, with the free amino acids accounting for 0.67 mg (61%) and the amino acids of protein origin accounting for 0.44 mg (39%). The distribution of each amino acid is shown in FIG. 1. Significant amount of taurine was also detected (not shown).

The major amino acids present in the (liquid) cartilage extract are representative of proteins and peptides from cartilage. For example, lysine, glycine, aspartic acid and glutamic acid represent a large proportion of the amino acid content of the liquid extract and are the main components of the N-telopeptide intermolecular cross-linking in collagen (Hanson et al. (1992) J. Bone & Min. Res. 7: 1251–1258).

Microbial limit of the liquid extract has been controlled, applying USP XXIII <61> standards.

Activity Assays

Solid Extract

In vitro Assays

These assays have been conducted on the hormone-dependent cancer cell lines MCF-7 and ZR75-1 (ATCC (R) numbers 22-HTB and 1500-CRL, respectively).

ZR75-1 Cells

Basal RPMI Medium: 52 g RPMI 1640 without phenol red (Sigma R8755), 17.875 g Hepes (free acid; Sigma H0763), 0.55 g sodium pyruvate (Sigma P5280) and 10 g $NaHCO_3$ were mixed in 5 L of pure water and made pH 7.40 with NaOH.

If not used immediately, this solution must be protected from light to preserve photolabile substances. This solution was filtered, distributed in 500 mL sterile bottles and stored at 4° C. for a maximal period of three months.

Cell Culture Maintenance Medium: Basal RPMI medium was supplemented with 10% (v/v) FBS (fetal bovine serum), 100 U penicillin G/50 µg streptomycin sulfate (Sigma P0906)/mL medium, 2 mM L-glutamine (Sigma G1517) and 1 nM $E_2$ (β-estradiol Sigma E8875).

Experimental Medium: Basal RPMI medium was supplemented with 5% FBSA (fetal bovine serum adsorbed on dextran-charcoal), 2 mM L-Glutamine, 100 U penicillin G/50 µg streptomycin sulfate/mL medium and 50 ng/mL insulin (Sigma). To this medium was added increasing concentrations of the above-described solid extract as well as different concentrations of $E_2$ ($10^{-12}$ to $^{-5}$ M). MCF-7 Cells:

BASAL DME-FI2 Medium: DME-FI2 medium (without bicarbonate and without red phenol; Sigma) was reconstituted following the manufacturer's directives in pure water. For one liter, 1.2 g of sodium bicarbonate was added and the pH made to 7.40 with NaOH/HCl. This solution was filtered, distributed in 500 mL sterile bottles and stored at 4° C. for a maximal period of three months.

Cell Culture Maintenance Medium: Basal DME-FI2 medium was supplemented with 10% (v/v) FBS (fetal bovine serum), 100 U penicillin G/50 µg streptomycin sulfate/mL medium, 2 mM L-Glutamine (Sigma) and 1 nM $E_2$.

Experimental Medium: Basal DME-FI2 medium was supplemented with 5% FBSA (fetal bovine serum adsorbed on dextran-charcoal), 2 mM L-Glutamine, 100 U penicillin G/50 µg streptomycin sulfate/mL medium and 50 ng/mL insulin (Sigma). As described for the ZR75-1 cells, solid extract and $E_2$ were added at the same concentrations.

Preparation of FBSA: Fetal bovine serum was mixed with 1% (w/v) charcoal (carbon decolorizing alkaline). A solution of dextran T70 was added to the charcoal-serum solution to achieve a concentration of 0.1% (w/v). The mixture was agitated overnight at 4° C. After centrifugation at 4° C. for 30 minutes at 10,000×g, the serum was decanted, mixed again with the same proportions of charcoal and dextran, agitated at room temperature for three hours and re-centrifuged. The serum was then heat-inactivated at 56° C. for 20 minutes, sterile filtered and aliquoted in sterile conical Falcon tubes.

Experimental Culture Assays and Results

ZR75-1 and MCF-7 cells were grown to reach a density of population of 20 000 cells/well on 24-well plaques or 150 000 cells/well on 6-well plaques, and treated in the presence or absence of different concentrations of solid extract as prepared above. To this effect, the solid extract is resuspended in culture medium and sterile filtered, so that hydro-soluble components thereof are recovered and tested. All experiments have been performed in triplicates. Culture media have been withdrawn and replaced by fresh media every two days. Cells were grown in an incubator under a constantly humidified atmosphere containing 5% $CO_2$, at 37° C., for 17, 7, 3 or 3 days, corresponding to the first, second, third or fourth experiment, respectively. Cell growth inhibition was measured by direct counting of the cells or by measuring the total DNA content of a well.

TABLE 1

|  | Cell Inhibition (%) | |
| --- | --- | --- |
| Concentration of solid extract | MCF-7 | ZR75-1 |
| 1st experiment: 17 days | | |
| 1 mg/ml | 1.5 | 2.0 |
| 5 mg/ml | 14.33 | 33.6 |
| 10 mg/ml | 62.66 | 90.8 |
| 2nd experiment: 7 days | | |
| 1 mg/ml | 3.73 | 0.97 |
| 5 mg/ml | 15.7 | 29.0 |
| 10 mg/ml | 68.37 | 66.0 |
| 3rd experiment: 3 days | | |
| 50 mg/ml | 95.8 | 95.0 |
| 100 mg/ml | 94.6 | 98.0 |
| 4th experiment: 3 days | | |
| 10 mg/ml | 34.4 | 51.5 |
| 20 mg/ml | 62.5 | 70.5 |
| 50 mg/ml | 95.8 | 95 |
| 100 mg/ml | 94.6 | 98 |

The above percentages of inhibition of cell growth demonstrate that the solid extract can inhibit in a dose-dependent manner the growth of these two cell lines.

FIG. 2 shows that doses of 50 and 100 mg/mL of the solid extract clearly provoke hypoplasia on these cell lines, after three days of treatment.

FIG. 3 shows that, in the presence of $10^{-12}$ to $10^{-9}$ M $E_2$, treated cells respond like control cells by being non-stimulated by these hormone dosage rates. However, above 1 nM, control cells are strongly stimulated, and concentration of DNA reaches 3.75 µg in the presence of $10^{-7}$ M $E_2$ (versus 0.69 µg in control without $E_2$). In cells treated with 30 and 50 mg/mL of solid extract, DNA measured at the maximal stimulation is 1.9 and 1.8 µg, respectively. FIG. 3 shows that the affinity constant (Km) of the treated cells for $E_2$ is 3 and 16 times higher (31.3 nM and 174.0 nM) than the value of Km of the control cells (11.7 nM), in the presence of 30 and 50 mg/mL of solid extract, respectively. This means that higher concentrations of $E_2$ are necessary to achieve the same growth of the cells when the solid extract is present. Therefore, this extract diminishes the maximal response (90% inhibition thereof) and increases the affinity constant of the treated cells to $E_2$. The results with the solid extract are indicative of a hydrosoluble component remaining entrapped therein, and which is extractable in an aqueous phase. Hydrosolubility is a key feature that should normally be satisfied prior to achieving a biological activity.

In vivo Assays

DMBA Induced Rat Mammary Breast Cancer Model

Description of the Test System: Four hundred 40 day old female Sprague-Dawley rats (purchased from Charles River Co., St-Constant, Quebec, Canada) were adapted to their environment for 12 days. At that time, 20 mg DMBA in 1 mL corn oil (9, 10-Dimethyl-1, 2-Benzanthracene; purchased from Sigma Chemical Co.) was administered by gavage. Three months after this treatment, 240 rats having developed a mammary breast cancer have been selected and distributed in two groups. The first group consisted of five sub-groups of rats. The rats of the treated groups were given a daily dose of increasing concentrations of the solid extract in 3 mL of water for eight weeks while the control group received the same volume of water. The second group consisted of four sub-groups of rats. The rats of the treated groups were also given a daily dose of the solid in 3 mL of water combined with or without the liquid extract, for ten weeks while the control group received the same volume of water. Only one sub-group of the second group of rats treated with a concentration of 3000 mg/Kg/day of the solid and 3 mL of the liquid extract was also given an intraperitoneal (i.p.) injection of a smaller dose of the liquid extract (about 8 mg of protein in 1 mL of water).

Rats weighed 151–175 g at the beginning of the two experiments and received food and water ad libitum. The first group of rats had tumors of average diameter of 0.9 cm while the second group of rats had a tumor of average diameter of 0.6 cm.

b. Anti-Tumor Activity: The results are summarized as shown in Table 2:

TABLE 2

| Daily doses of solid extract administered by gavage | % tumor growth inhibition (decrease of tumor diameter versus control) |
|---|---|
| 1st experiment: duration 8 weeks | |
| Placebo | 0 |
| 500 mg/Kg/day | 2 |
| 1000 mg/Kg/day | 4 |
| 3000 mg/Kg/day | 14 |
| 5000 mg/Kg/day | 15 |
| 2nd experiment: duration 10 weeks | |
| Placebo | 0 |
| 3000 mg/Kg/day | 12 |
| 3000 mg/Kg/day 3 mL liquid extract | 18 |
| 3000 mg/Kg/day + 3 mL liquid extract + 1 mL liquid extract i.p. | 20 |

These results demonstrate that the solid extract contains an active component that is absorbed in the gastrointestinal tract and slows down tumor progression. This inhibition might be a direct effect on the tumor cells or an anti-angiogenesis mediated effect interfering with tumor growth.

The liquid extract also contains inhibitory activity since its administration caused an additional reduction of tumor size of about 6%.

These results suggest that the solid extract contains residual hydrosoluble active components, which could be re-extracted in an aqueous solution to recover hydrosoluble components maximally, if the yield can be still improved.

c. Histopathology: For evaluating the non-toxicity of the solid extract, the animals used in the above in vivo experiments were killed by decapitation and the following tissues were taken for analysis: liver, lung, kidneys, heart, brain, muscle and mammary glands. Fat was taken out of these tissues. After that, they were fixed for two days in Bouin fluid. After dehydration in ethanol, the fixated tissues were embedded in paraffin. Sections thereof were obtained and mounted on glass slides, stained with haematoxylin and visualized under microscope.

The histological examination revealed that no deleterious effect was visible when using the largest doses of solid extract alone or when using the solid extract in combination with the liquid extract (data not shown).

This suggests that the solid extract and the liquid extract have a selective tumor size regressive activity.

Figure 4A:
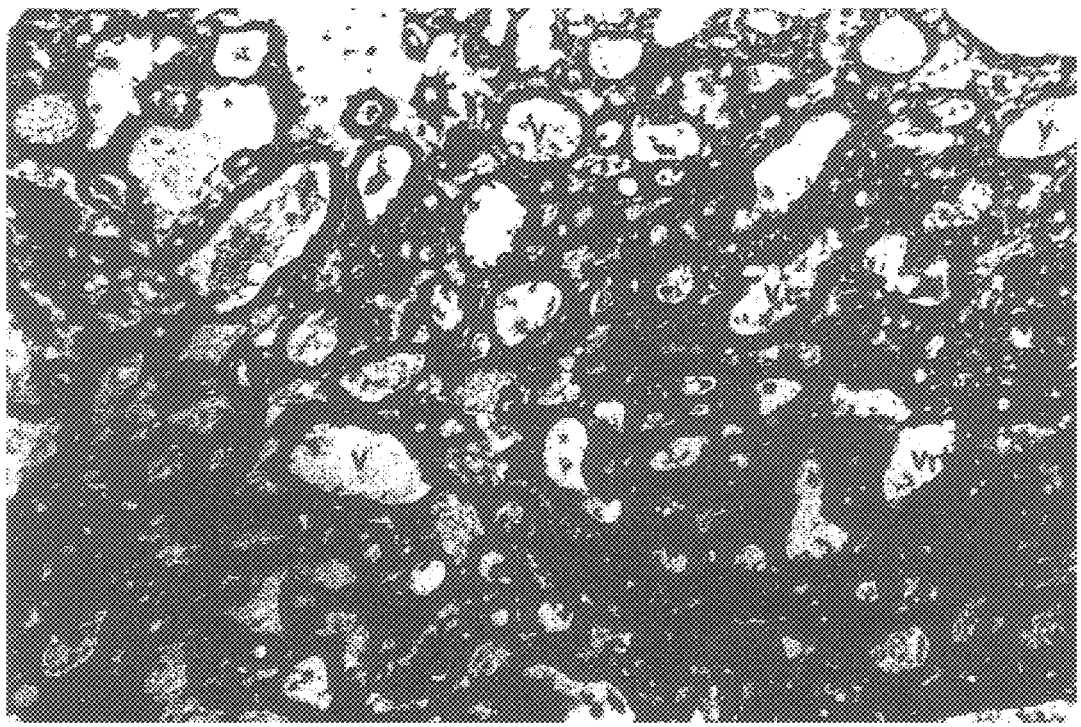
FIGS. 4a) and b) show a comparison of mammary gland tumor sections of rats which have been administered by gavage of water (A) or a combination of solid and liquid cartilage extracts (B).
Figure 4B:
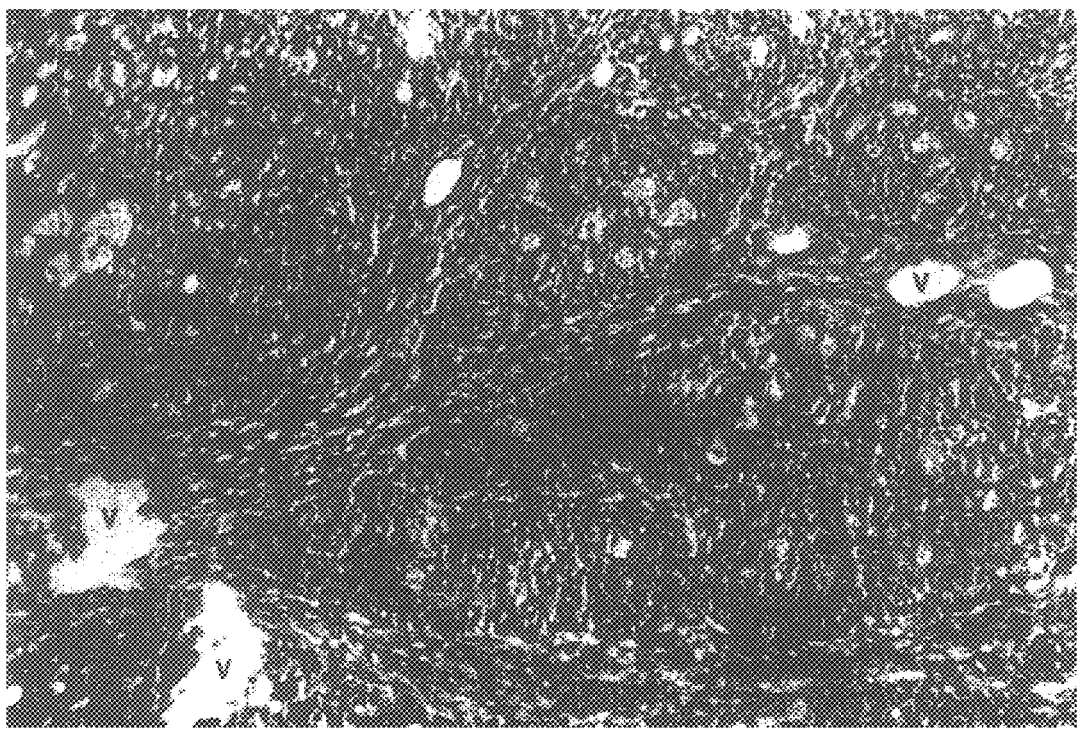

In mammary gland tumors (see FIGS. 4a and b), an important diminution (55%) of the area of blood vessels was observed in the group of rats having received solid and liquid cartilage extracts (FIG. 5).

The diminution of the tumor size might be due to an important decrease in its vascularization, to a direct effect on tumor cells, or a combination of both phenomena. The anti-angiogenic effect of these extracts is well depicted above. The direct hypoplasiant effect has been observed in vitro on hormone-dependent cells, which has been confirmed in vivo.

Because the above-mentioned results showed that the liquid extract had an increasing effect over and above the effect of the solid cartilage extract on ZR75-1 cells, the components thereof were further investigated.

Liquid Extract

In vitro Assay

Tumor Cell Lines

Several tumor cell lines were grown in the presence of liquid cartilage extract to examine whether the hypoplasiant activity observed with the solid extract (above section) was present in the liquid extract.

Briefly cells were plated in 96 well plates and grown in culture media (specific for each cell type; for example, MCF-7 cells were grown as described in above section) in presence or absence of various concentrations of liquid extract. Cell proliferation was measured using a MTT assay following 3 to 5 days of culture. The tumor cell lines were:

| CHANG | Tumor hepatocytes |
|---|---|
| Hep-G2. | Tumor hepatocytes |
| A2780 | Ovarian adenocarcinoma cells |
| MCF-7 | Breast adenocarcinoma cells (estrogen dependent) |
| MCF-7-ADR | Adriamycin-resistant breast adenocarcinoma cells. |

The liquid cartilage extract showed antiproliferative activity on all tumor cell lines. The strongest inhibitions, 50 and 80%, were obtained at a concentration of 8.5 mg/mL (dry weight of liquid extract/mL of culture medium) on MCF-7 and A2780 cells, respectively.

Primary Cultured Cells

Fibroblasts from Neovascular Glaucoma: In order to evaluate the specificity of biological activity on tumor cells, the liquid extract was tested on mesenchyme originating cells, human TENON fibroblasts (HTFs), which are normal fibroblasts. HTFs from two patients (one with neovascular glaucoma, NVG, and the other with primary open angle glaucoma, POAG) have been used.

Subculturing and Maintenance of HTFS: Each confluent culture was passaged by washing and detaching with –0.5 mL of 0.05% trypsin/0.5 mM EDTA (Gibco 610-5300 AG) for 5–10 minutes at 37° C. DME/F-2 medium (1.5 mL) containing 15% fetal bovine serum (FBS) was then added to neutralize trypsin/EDTA.

Association of the cells was made by triturating and transferring into 25 $cm^2$ T-flasks, into which additional medium containing 10%(FBS) was added. After confluence was reached, the HTFs were transferred into 75 $cm^2$ and eventually, into 180 $cm^2$ T-flasks. When enough cells were obtained, some cells were utilized for the experiments as described below, and others were simultaneously frozen to preserve identical passages for future experiments.

Experimental Protocols: When confluence was reached, cells from one patient growing in two or three identical 180 $cm^2$ T-flasks were dissociated by the procedure described above. After a short low speed centrifugation, they were counted with a ZMI Coulter Counter 216013, equipped with a 256-Channelyzer.

For all the in vitro experiments that follow, approximately fifty thousand cells were inoculated in 1 mL of DME/F-2 medium containing 1% FBS into each 16 mm dish and a 12-well plate. Seventeen hours (hrs) after seeding, 1 mL of fresh identical medium supplemented with 1% FBS ("absolute" controls) was added. Depending on the experimental design (see above and below), the 1% FBS medium was supplemented or not with GFs (Growth Factors) or with the liquid cartilage extract, and sterile filtered. On this day (day 0), some samples of cells were also counted to determine plating efficiency (which should be equal or greater than 95%).

Forty-eight hours after the onset of the experiments, the cells were rinsed, dissociated and counted again. The number of cells was expressed as a percentage of that obtained in the "absolute" controls.

Each "absolute" control, containing 1% or 5% FBS, respectively, and each experimental group, supplemented with 1% FBS and with an individual GF or liquid cartilage extract consisted of triplicate samples.

Each experiment was carried out on the cells of one or two patients at a time, and was repeated at least twice.

In these experiments, GFs, porcine platelet-derived growth factor (PPDGF) and human recombinant basic fibroblast growth factor (hr bFGF) were added in concentrations of 10 to 100 ng/mL in 1% FBS, respectively. Forty-eight hours after the onset of the experiment, the cells were dispersed by Trypsin-EDTA and counted on the Coulter counter. All triplicate values (columns 1, 2 and 3) appearing below equal one twentieth of counts per well.

Figure 6:
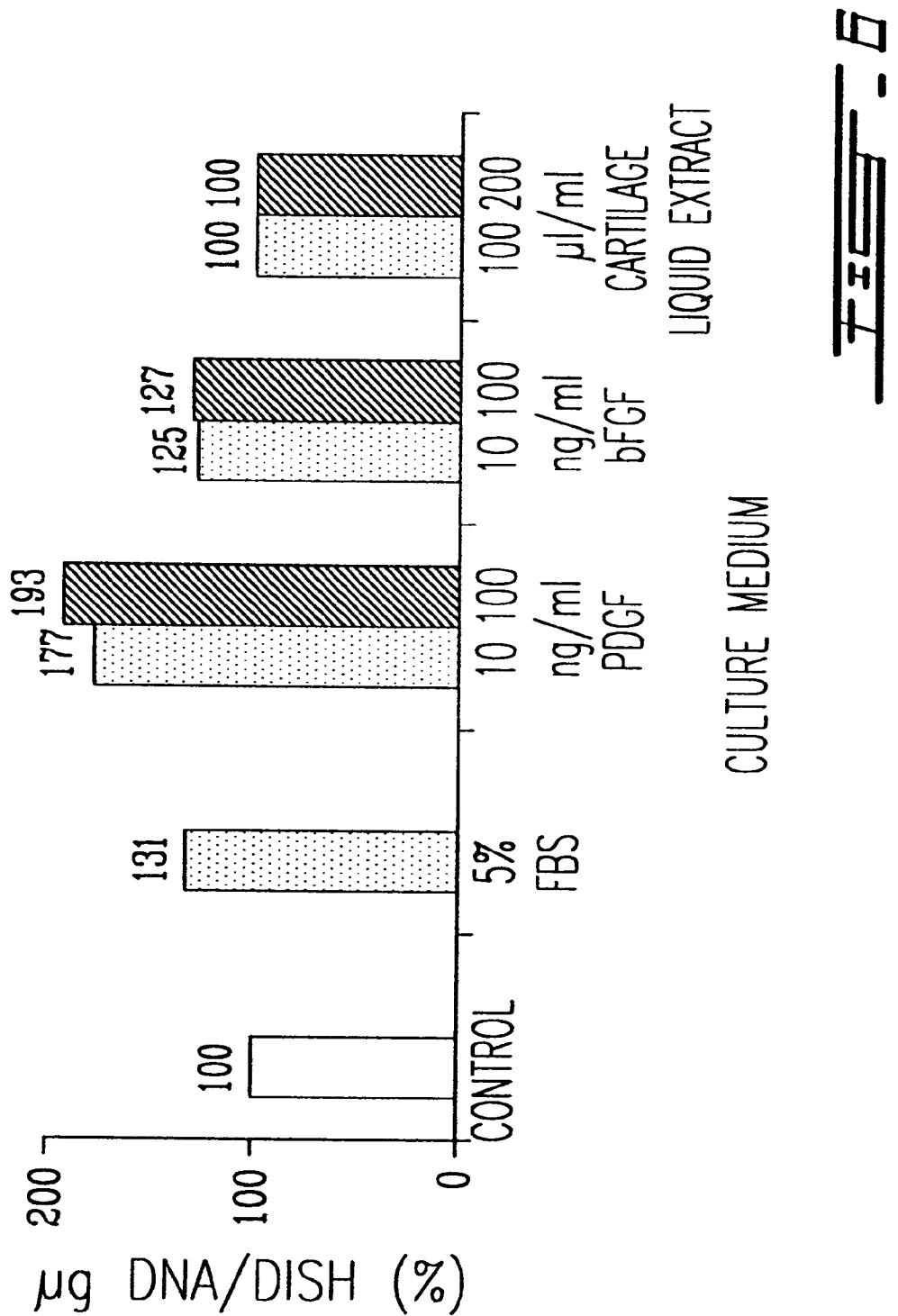
FIG. 6 shows that the liquid cartilage extract has no effect on fibroblast cell proliferation.

Results: The results are summarized in FIG. 6. HTFs were obtained from the glaucoma of a 53 year old man. While growth factors like PDGF and bFGF showed a stimulating activity on HTFs (*$P<0.02$, **$P<0.01$; determined by Student-Fisher Test), no effect, positive or negative, was obtained when these cells were grown in the presence of liquid cartilage extract (I Kg/2L). This suggests that the hypoplasiant activity of the liquid cartilage extract on tumor cells is not universal and does not affect the growth of fibroblasts. The same cartilage extract neither had an effect on another type of fibroblast cells, HSF (Human Skin Fibroblasts; data not shown). Even though not tested, it is assumed that the solid extract also produces no effect on normal cells.

Endothelial Cells from Human Umbilical Vein (HUVECs): HUVECs were extracted with collagenase-controlled digestion as described in Jaffe et al. (1973). Pure endothelial cells were used before the fourth passage (trypsin-EDTA at each passage). Quality of the cells were analyzed for their capacity to incorporate di-acetylated LDL and to be labeled with factor VIII.

Endothelial cells were plated at a density of 2 500 cell/$cm^2$ into sterile dishes coated with gelatin. Cells were cultured with complete medium (Medium199+heparin (90 µg/ml)+L-glutamine (2 mM)+bicarbonate+Fetal Bovine Serum (10%)+Endothelial Cell Growth Stimulant (120 µg/ml)) during 24 h to insure cell adhesion. Then, the cells were washed 3 times with PBS and the culture medium was added according to experimental conditions. The last PBS wash was considered as time 0.

Each experiment was performed in triplicate and statistic analysis was performed for comparison. Culture medium was changed after 24 h, and every other day. After 168 h of culture, BrdU (10 mM final) was added to each culture media and incubated 2h at 37° C. Then, cells were detached with short trypsin-EDTA digestion and transferred into 96-well plates to allow ELISA detection of BrdU. ELISA was performed with a kit from Boehringer Mannheim. A control was performed without cells to determine the background. Another control was performed by measuring the DNA content in the culture medium at the end of the incubation period to sort out whether the liquid cartilage extract affected cellular adhesion.

Cell proliferation was also evaluated with the amount of DNA present in the petri dishes. Each experiment was performed in triplicate and statistical analysis was performed for comparison. Culture medium was changed daily. After 168 h of culture, cells were lysed with Na-Citrate-sodium dodecyl sulfate solution and incubated with the Hoescht 33358 dye. Samples were read at 365 nm with a spectrofluorometer.

Finally, the amount of cells present in petri dishes was evaluated by measuring acid phosphatase activity. Each experiment was performed in triplicate and statistical analysis was performed for comparison. The activity of this enzyme showed a strong correlation with the number of endothelial cells in petri dishes (BrdU incorporation and Hoescht labeling; data not shown). Acid phosphatase activity was measured with a kit from Sigma Chemical Company.

Results

Figure 7:
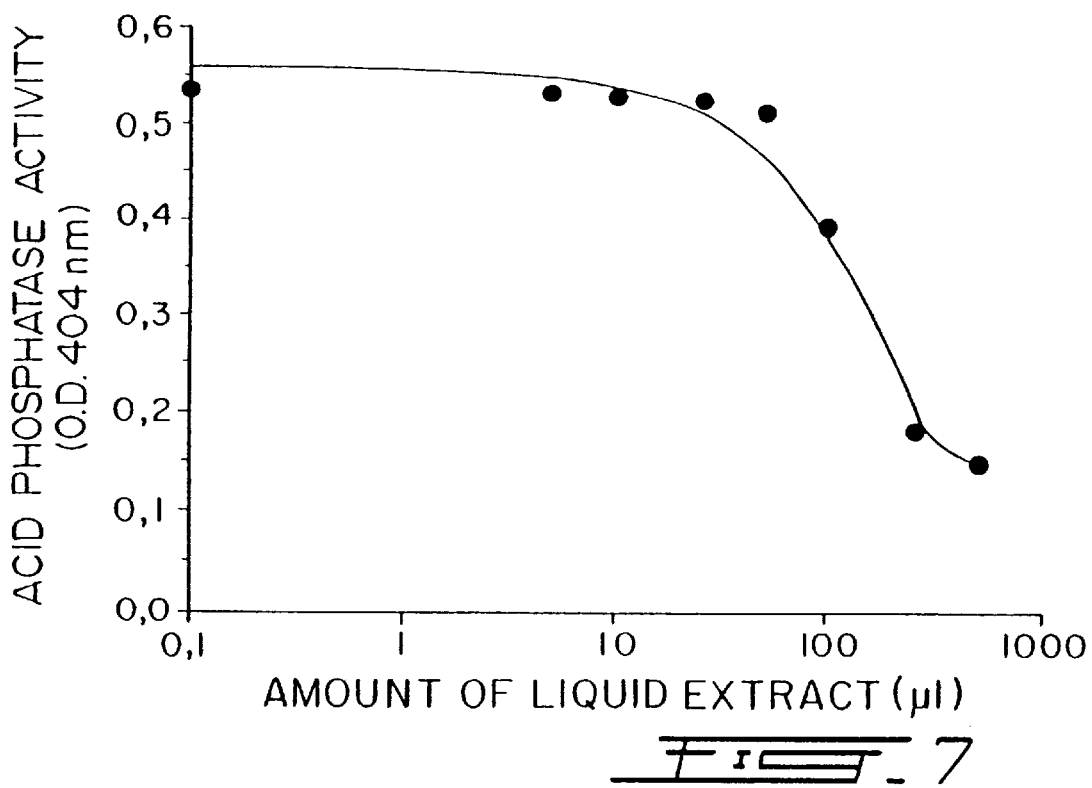
FIG. 7 shows a dose-response curve inhibition of liquid cartilage extract on HUVECs proliferation.

The results demonstrated a dose-response inhibition of endothelial cell proliferation with the liquid cartilage extract (FIG. 7). The ED50 obtained is approximately 90 µl of liquid cartilage extract (equivalent to approximately 1.5 mg dry weight present in the liquid extract).

Keratinocytes: Liquid cartilage extract was tested in keratinocytes which Protein Kinase C (PKC) was activated by triphorbol acetate (TPA), a known agonist of this cellular transduction pathway.

Normal human epidermal keratinocytes were established as primary cultures (Matsui et al. (1992) J. Invest. Dermatol. 99: 565–571). Cultures were grown in a serum-free defined medium (KGM) containing epidermal growth factor (10 ng/ml), insulin (5 μg/ml), hydrocortisone (0.5 μg/ml) and bovine pituitary extract (70 μg/ml) in a modified MCDE 153 formulation.

Keratinocytes were grown to 70% confluence, and 48 h after refeeding with fresh medium, treated with either 200 ng/mL TPA or 2 μl/mL DMSO with no additional refeeding. Various concentrations of liquid cartilage extract were added or not to the culture medium.

Results

Figure 8:
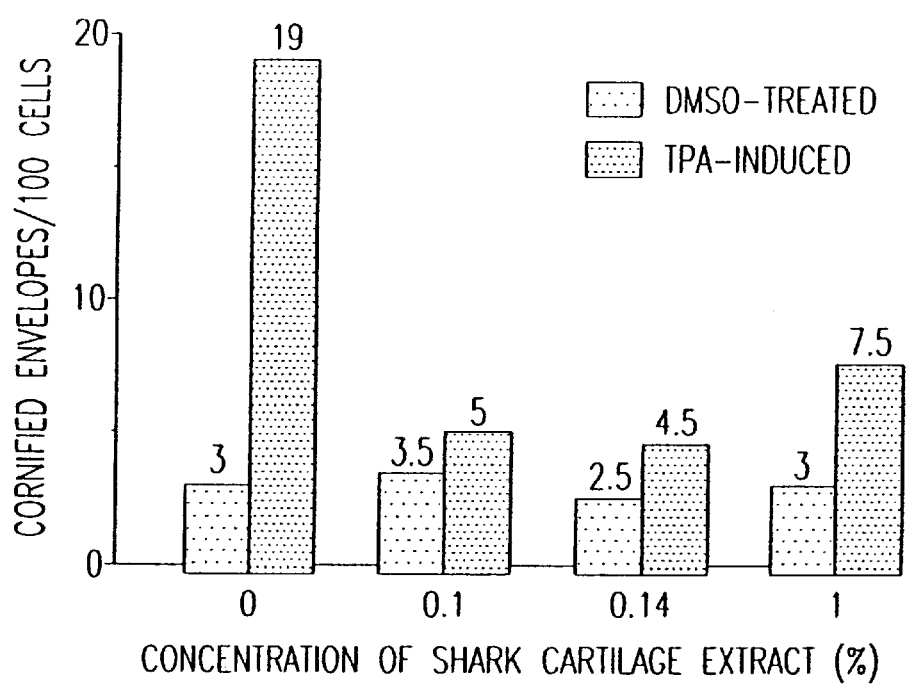
FIG. 8 shows that liquid cartilage extract inhibits TPA-induced keratinocyte differentiation.

The results showed no effect of the liquid extract on keratinocyte proliferation; it also had no effect on TPA-induced inhibition of proliferation. However, liquid cartilage extract was able to inhibit TPA-induced keratinocyte differentiation (FIG. 8). The level of differentiation of the keratinocytes was increased 5-fold by TPA. Liquid cartilage extract by itself had no effect on cornified envelope formation. However, liquid cartilage extract inhibited TPA-induced cornified envelope formation by more than about 60%.

Recent publications have shown that PKC activation led normal keratinocytes to produce increased amounts of interleukin-8 (IL-8), a mediator of inflammation (Chabot-Fletcher et al. (1994) J. Invest. Dermatol. 103: 509–515). Moreover, psoriatic keratinocytes produce very high amounts of IL-8, which further promote neovascularization in psoriatic plaques (Nickoloff et al. (1994) Am. J. Pathol. 144: 820–828). It therefore appears that psoriasis has at least two key etiologies: inflammation and angiogenesis. Other possible etiologies include metalloprotease activity and endothelial cell proliferation. Other cytokines, growth factors and integrins are also involved in psoriasis.

It is not known whether TPA-induction mimics psoriatic keratinocytes. If such is the case, these results suggest that cartilage may have no deleterious effect upon normal keratinocytes in vivo, while it may have an effect on psoriatic (or activated) keratinocytes. Inhibition of the production of IL-8 in TPA-activated keratinocytes as well as in psoriatic plaques or keratinocytes by the liquid cartilage extract remains to be verified. Decreased IL-8 levels and/or other growth factors might explain the anti-inflammatory and anti-angiogenic effects of this extract.

Collagenase Assay

This assay is described in Knight et al. ((1992) FEBS Let. 296, 263–266). The method utilizes a fluorogenic peptide substrate mimicking the active site of metalloproteinases. This substrate has a fluorescent group at one end and a fluorescence quenching group at the other. In the intact substrate, the quenching group effectively masks the fluorescence. Upon enzyme cleavage of the substrate, the fluorescence in the test tube increases.

Collagenase activation is described in Weingarten et al. (1985) in Biochemistry vol. 24, p. 6730. 1 μg was diluted to 100 μl with 50 mM Tris-HCl, 10 mM $CaCl_2$. The pH 7.5, 1 μl at 10 mg/mL solution of trypsin (in 1 mM HCl) was added and incubated for 15 min at 20° C. Activation was terminated by adding 10 μl of soybean trypsin inhibitor (SBTI, 5 mg/ml). To each microcuvette was added:

25 or 50 μl inhibitor* (made up to 50 μl with water);
40 μl 50 mM Tris-HCl, 200 mM NaCl, 10 mM $CaCl_2$, pH 7.5;
8 μl activated collagenase** (67 ng final); and
2 μl substrate (1 mM stock solution in DMSO, 20 μM final).

Fluorescence was recorded at λex=328 μm, λem=393 nm.
*: the inhibitor is defined as a control substance (such as EDTA or Orthophenanthrolene) or the liquid cartilage extract.
**: the collagenase is defined as human type I, type IV, and amphibian tadpole collagenase; gelatinase has also been used.

Twenty-one ng of activated collagenase was added to 5 μg of calf skin collagen (Worthington) +/−inhibitor in a final volume of 20 μl. Reactions were incubated for 16 h at 35° C., then stopped by adding SDS-PAGE sample with 40 mM EDTA, boiled and loaded on a 8% polyacrylamide gel.

Results

Figure 9:
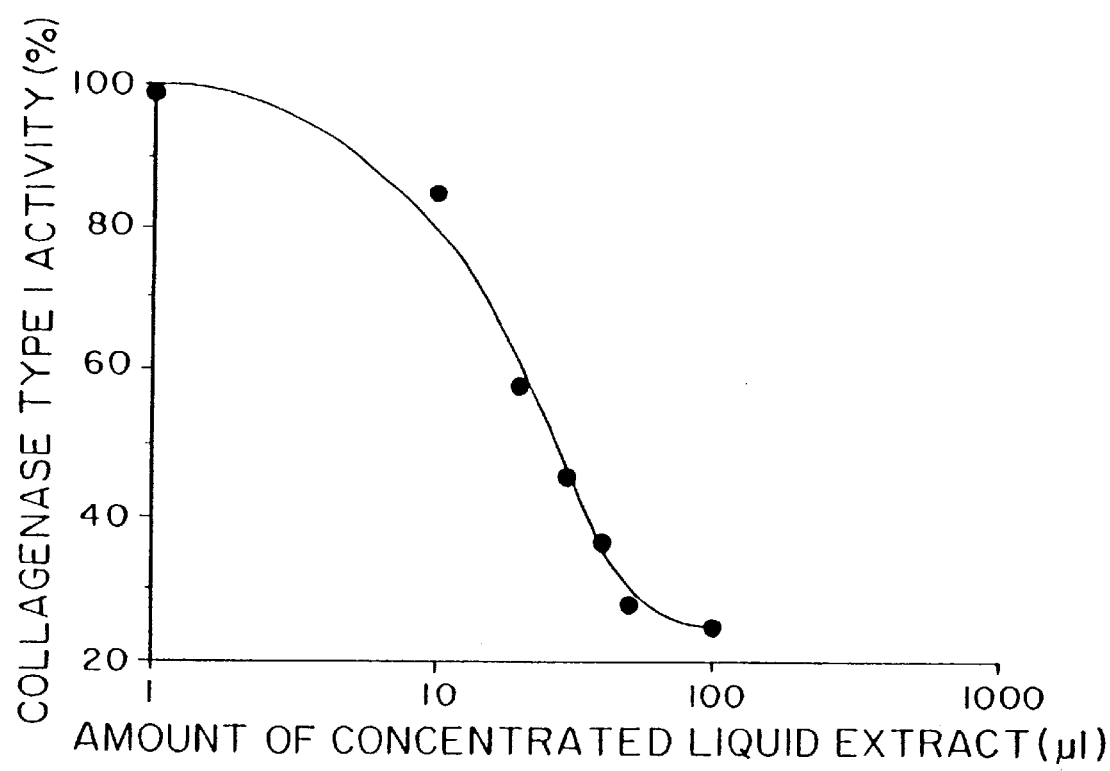
FIG. 9 shows a dose-response curve inhibition of liquid cartilage extract on collagenase activity.

The results obtained with liquid cartilage extracts showed a dose-response inhibition of collagenase activity. FIG. 9 shows results obtained with collagenase assay. The $ED_{50}$ is obtained with 30 μl of liquid extract (or 0.51 mg dry weight present in 30 μl of liquid extract).

Assays for Evaluating the Interference with VEGF

The formation of new blood vessels is essential for a variety of physiological processes. It requires the co-operation of a variety of molecules that regulate cellular processes such as extracellular matrix (ECM) remodeling, invasion, migration and proliferation. (Ingber, Sem. Cancer Biol. (1992) 3: 57–63; Schwartz, S. M. et al. (1993) J. Cardiovasc. Pharmacol. 21(Suppl. 1): S31–S49; Auerbach, W. et al. (1999) Pharmac. Ther. 1994; 63:265–311; Moses, M. A. et al. (1995) Int. Rev. Cytol. 161:1–48; Brooks, P. C. (1996) Cancer Metastasis Rev. 15:187–194.) Abundant evidence also suggests that angiogenesis is preceded and/or accompanied by enhanced microvascular permeability. Vascular permeability is also one of the key events of inflammation. This means that collagenolysis, inflammation and angiogenesis share common mechanisms or at least have mechanisms that are inter-related.

In general terms, angiogenesis is organized into three major phases: an initiation phase, a proliferative/invasive phase and a differentiation/maturation phase (Brooks, P. C. (1996) Eur. J. Cancer 32A: 2423–9). The initiation phase can be triggered by activation of vascular cells via a variety of angiogenic cytokines and other physiological mediators (Klagsbrun, M. et al. (1991) Annu. Rev. Physiol. 53:217–32; Ferrara, N. (1995) Nature 376–467; Koch, A. E., et al. (1995) Nature 376:517–19; Bussolino, F. et al. (1996) Eur. J. Cancer 32A: 2401–12; Mazure, N. M. et al. (1996) Cancer Res. 56:3436–40; Ferrara, N. et al. (1997) Endocrine Rev. 18:4–25; Sandner, P. et al. (1997) Kidney Int. 51:448–53). A partial list of the more well-characterized growth factors known to promote angiogenesis include basic fibroblast growth factor (bFGF), vascular endothelial growth factor (VEGF), platelet-derived growth factor (PDGF) and tumor necrosis factor alpha (TNF-alpha). These cytokines and other angiogenic molecules can be released from a number of sources, including endothelial cells, inflammatory cells, mast cells and macrophages, as well as from a variety of tumor cells (Knighton, D. R. et al. (1983) Science 221:1283–85; Scheweigerer, L. et al. (1987) Nature 325:257–9; Hamada, J. et al. (1992) Br. J. Cancer 66:349–354; Rak, J. E. et al. (1994) J. Cell Physiol. 159:245–55; Rak, J. et al. (1996) Eur. J. Cancer 32A: 2438–50; Moses, M. A. (1995) et al. Int. Rev. Cytol. 161:1–48; Proost, P. et al. (1996) Int. J. Clin. Lab. Res. 26:211–23; Polverini, P. J. (1996) Eur. J. Cancer 32A:2430–7; Ferrara, N. et al. (1997) Endocrine Rev.

18:4–25). The proliferative/invasion phase of angiogenesis is characterized by cell replication (Form, D. M., et al. (1986) *Lab. Invest.* 55:521–530), re-organization of proteins of the cytoskeleton and those involved in membrane adhesion (Pepper, M. S. et al. (1992) *J. Cell Physiol.* 152;196–205; Klein, S. et al. (1993) *Mol. Biol. Cell* 4:973–82; Klein, S. et al. (1996) *J. Biol. Chem.* 271:22583–90) and production of proteases that are secreted to promote endothelial cell migration in the surrounding matrix (Mignatti, P. et al. (1994), *J. Cell. Biol.* 113:1193–201). Finally, the differentiation/maturation phase is characterized by endothelial cell production of a basement membrane, lumen formation and junctional coupling with other cells (Pepper, M. S. et al., *Biochem. Biophys. Res. Commun.* (1992) 189:824–31; Bischoff, J. (1995) *Trend Cell Biol.* 5:69–74).

VEGF is a multifunctional angiogenic growth factor. It stimulates the endothelial cells to proliferate and to migrate. It is also a permeabilising agent that renders the endothelial tissue hyperpermeable, leading to the extravasation of plasma proteins. This conducts to a transformation of the extracellular matrix and a stimulation of angiogenesis.

Accordingly, the effect of the present shark cartilage extract on the VEGF activity was established both in vivo and in vitro: it blocks the stimulation of endothelial cell proliferation, it competes with the binding the VEGF to its receptor, and it blocks the extravasation induced by VEGF. Therefore the shark cartilage extract (also called AE-941) has anti-metalloprotease, anti-angiogenic and anti-inflammatory activities that appear to be due in part to its action on VEGF activity.

Endothelial Cell Proliferation

Human Umbilical Vein Endothelial Cells (Clonetics Corp.; San Diego, Calif.) were cultured in M199-bicarbonate buffered medium supplemented with heparin 100 µg/ml, L-glutamine 2 mM, ECGS 20 µg/ml, 10% FBS, and penicillin-streptomycin (1%). Four thousand cells were seeded in 96-well sterile culture dishes and cultured for a 6- to 8-hour period to allow cell attachment. Afterward, the cells were starved for 24 h in M199-bicarbonate buffered medium supplemented with 2% FBS and antibiotics. Then, fresh medium (2% FBS and antibiotics) containing increasing concentrations of VEGF or bFGF was added to the cell cultures. Cells were incubated for 3-day period. Cell number was then evaluated by a colorimetric assay using the cell proliferation reagent tetrazolium salt WST-1 according to the procedure established by the manufacturer (Boehringer Mannheim).

Bovine Artery Endothelial Cells (BAEC): The BAEC were isolated from fresh aortas in our laboratory. Their identification was established by their cobblestone monolayer morphology, factor VIII immunochemistry and by negative smooth muscle cell α-actin staining. The BAEC were cultured in DMEM supplemented with 5% FBS and penicillin-streptomycin (1%).

Results

Figure 28A:
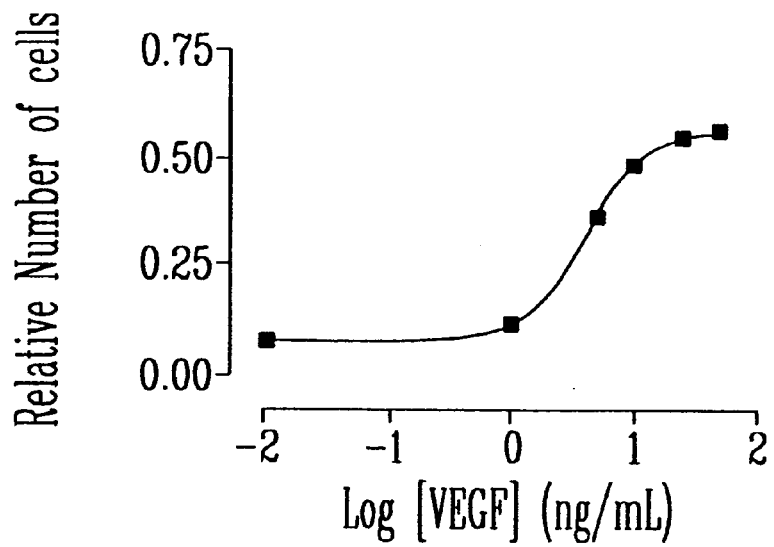
FIG. 28a) shows the effect of VEGF on HUVEC proliferation.
Figure 28B:
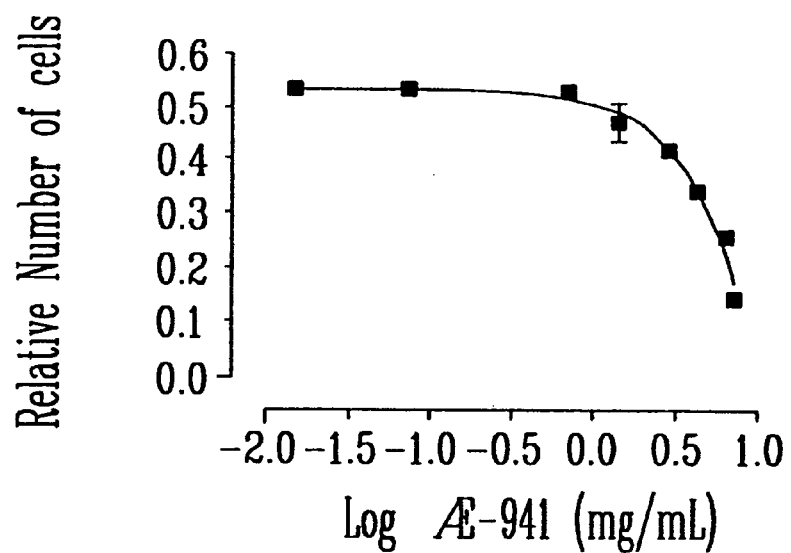
FIG. 28b) shows that the present cartilage extract counteracts VEGF activity on HUVEC proliferation.

The presence of functional VEGF receptors expressed in HUVEC is shown by a dose-dependent stimulation of the proliferation by VEGF (FIG. 28a). Moreover, it was demonstrated that the present shark cartilage extract can inhibit the proliferation of HUVEC induced by VEGF (10 ng/mL) (FIG. 28b). The resulting $IC_{50}$ of the cartilage extract Æ-941 in VEGF-stimulated HUVEC corresponds to 2.55 mg/mL.

TABLE 3

Kd and Bmax of VEGF and bFGF receptors in HUVEC

| Binding site | Kd (nM) | Bmax (fmol/10 cells) |
|---|---|---|
| VEGF | 0.12 | 2.6 |
| bFGF | 0.36 | 4.5 |

Radioreceptor Binding Assay With $^{125}$I-VEGF or $^{125}$I-bFGF

Binding studies were performed on HUVEC and BAEC grown at confluence in 24- or 12-well tissue culture plates, respectively. The binding buffer was M199 media supplemented with 5 mM Hepes and 0.1% gelatin at pH 7.3. Saturation of VEGF and bFGF receptors were determined by adding 0.2 mL (for HUVEC) or 0.5 mL (for BAEC) of binding buffer containing increasing concentrations of $^{125}$I-VEGF or $^{125}$I-BFGF (0.05–10 mg/well) to the endothelial cells in culture for a 2-hour period at 4° C. Non-specific binding was determined at each concentration by adding a 100-fold excess of unlabeled VEGF or bFGF. At the end of incubation, cells were washed twice with ice-cold M199 containing 1 mg/mL of bovine serum albumin. The cells were collected after trypsin incubation, and the radioactivity evaluated on a γ counter. Binding site competition studies for $^{125}$I-VEGF or $^{125}$I-bFGF (4 ng/well; a concentration close to the saturation) was evaluated in the presence of increasing concentrations of unlabeled VEGF or bFGF (0–400 ng/well), or cartilage extract (0–7.2 mg/well). Each determination was performed in triplicate.

Results

Figure 29A:
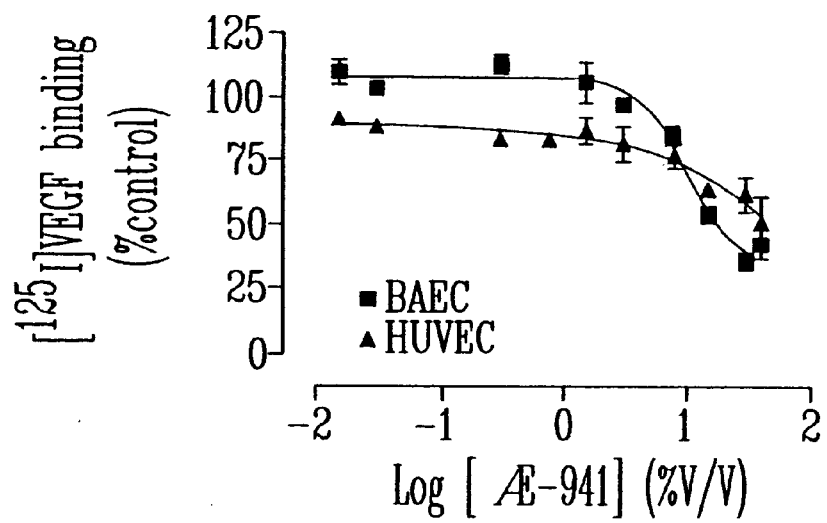
FIG. 29a) shows that the present cartilage extract interferes in some way with the binding of VEGF to its receptor in HUVEC and BEAC models. This effect is specific to VEGF since (FIG. 29b)) shows that no such competition is observed against the binding of bFGF to its receptor.
Figure 29B:
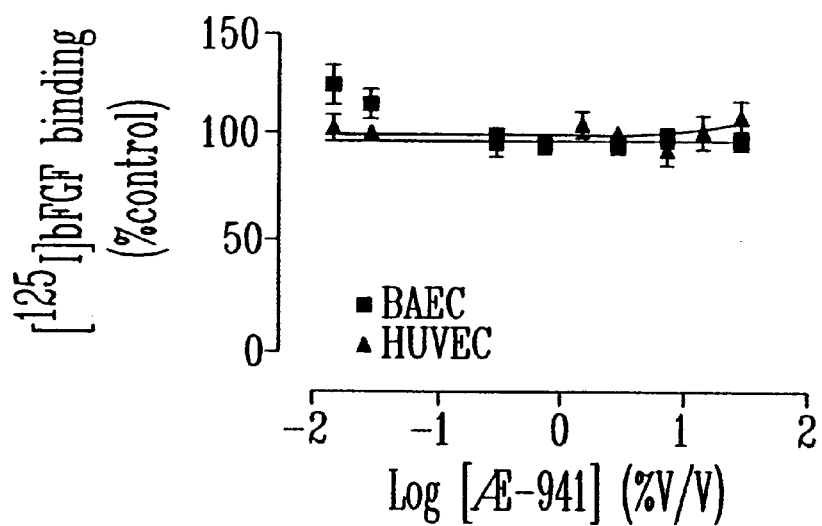

Competitive binding assays of the present cartilage extract for VEGF were conducted in HUVEC and bovine artery endothelial cells (BAEC). Results indicated that present cartilage extract competes with the binding of VEGF to its receptor while it did not for bFGF (FIGS. 29a and 29b), although it inhibits bFGF mitogenic activity (not shown).

TABLE 4

Competition of Æ-941 to the binding of VEGF and bFGF to their respective receptor binding sites

| Radioligand | Cold ligand | $IC_{50}$ |
|---|---|---|
| $^{125}$I VEGF (4 ng) | VEGF | 0.48 nM |
| $^{125}$I-bFGF | Æ-941 | 2.71 mg/mL |
| $^{125}$VFGF (2 ng) | bFGF | 0.57 mM |
| $^{125}$I-bFGF | Æ-941 | Not applicable |

Inhibition of VEGF Induced Extravasation

This study aimed at determining whether oral administration of Æ-941 could inhibit the extravasation of Blue Evans (BE) dye in mice. Toward this end, mice were orally treated with Æ-941 (150 mg/ml) or saline prior to I.V. administration of VEGF (0.1 nmol/kg) and BE (20 mg/kg).

Results

Figure 30:
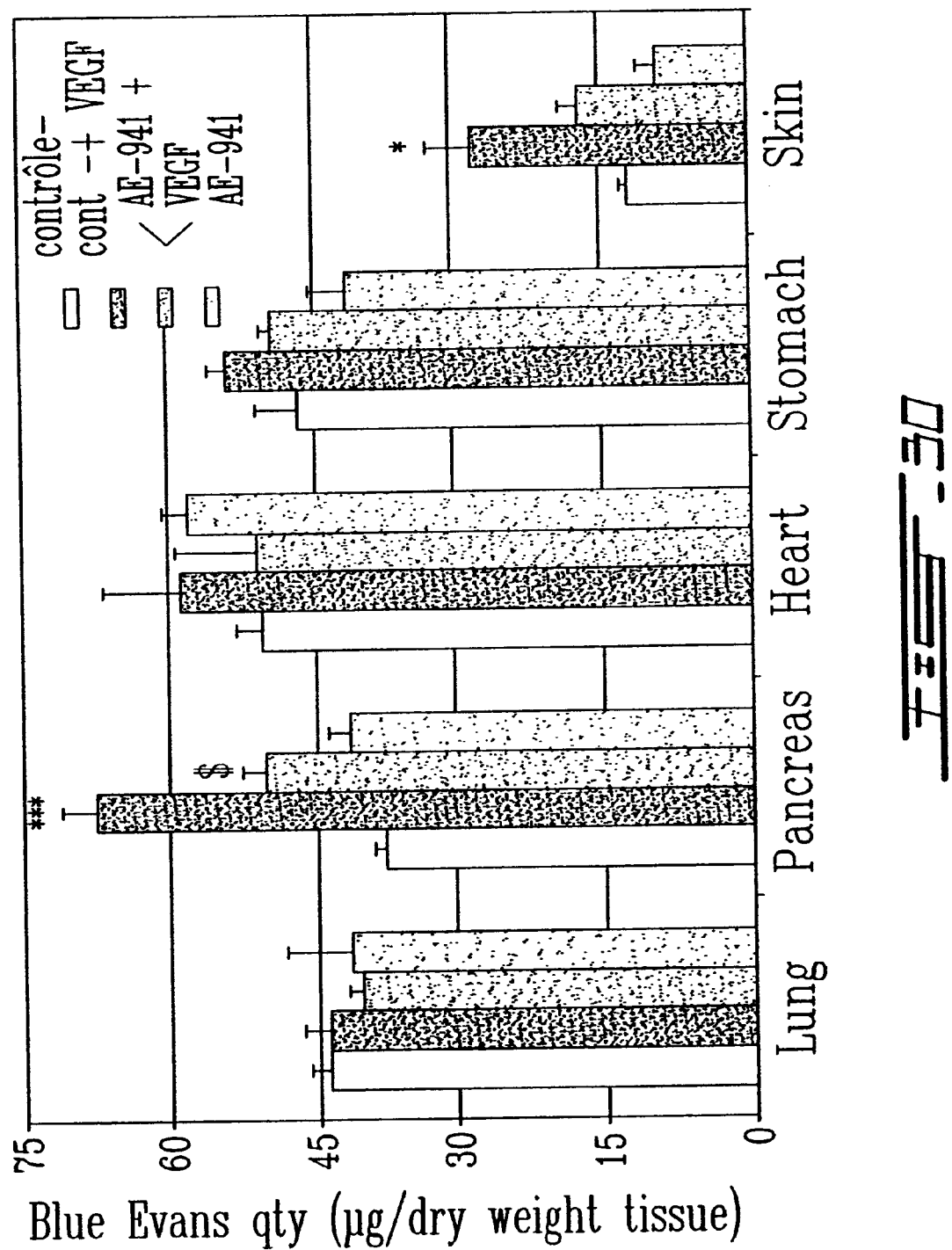
FIG. 30 shows that the present cartilage extract inhibits the extravasation induced by VEGF. This is presumed to be one of the ways by which the extract hinders the initiation of edema and inflammation at the origin of a cascade of events involved in extracellular matrix remodelling.

The amount of BE present in various organs 10 min after VEGF administration was illustrated in FIG. 30. These results indicate that oral administration of Æ-941 cartilage extract in mice significantly reduces the induction of extravasation by VEGF and support its oral bioavailability.

Inhibition of VEGF Receptor Phosphorylation

The effect of the liquid extract upon VEGF receptor phosphorylation was determined to elucidate a possible mechanism by which the cartilage extract blocks the action of VEGF. The effect of VEGF on VEGF-receptor phosphorylation was determined on BAEC that were pre-treated with the liquid extract.

BAEC were treated during 18 hours in a serum free medium in the presence or absence of the cartilage extract (7 mg/ml; 50%). Cells were then stimulated with VEGF (1 nM) for one minute or $CNF_1$ toxin (1 µg/ml) for six hours. Afterward, the cells were lysed and the VEGF receptors were immunoprecipitated with antibodies specific for either the type 1 or type 2 receptors. The degree of phosphorylation of these two receptors was determined by immunoblot with an anti-phosphotyrosine antibody.

Results

Figure 31:
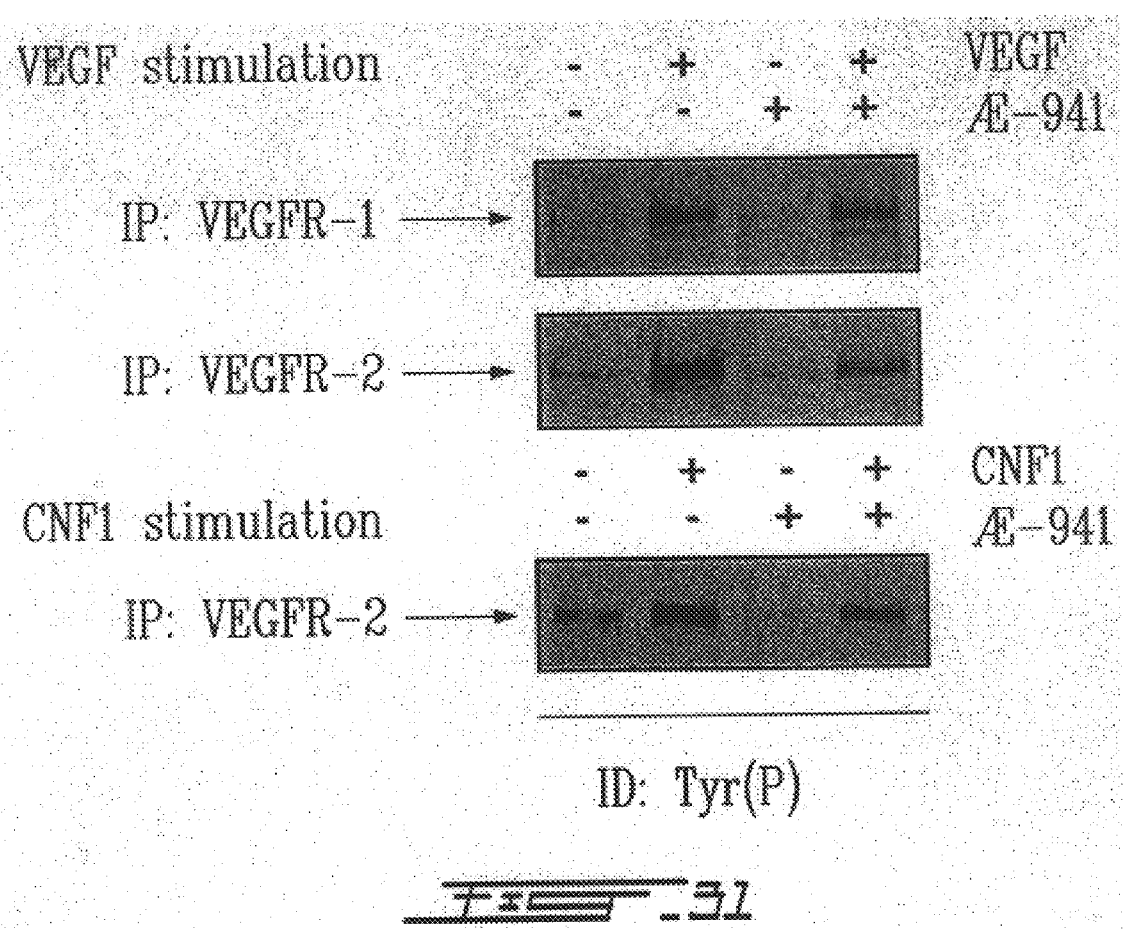
FIG. 31 shows that at least a part of the interference of the cartilage extract with VEGF activity is due to an inhibition of the phosphorylation of VEGF receptor.

As illustrated in FIG. 31, the liquid extract reduced the ability of VEGF to stimulate VEGF-receptor phosphorylation by approximately 50%. This effect appears more pronounced for the type 2 VEGF-receptor than for the type 1 VEGF-receptor. Similar results were obtained with the $CNF_1$ toxin, which induces the phosphorylation of type 2 VEGF-receptor. These results indicate that the liquid extract contains components that interact directly with the VEGF-receptor.

Other Anti-Metalloprotease Activities

Other molecules that are targeted by the components of the present cartilage extract have been investigated. The anti-angiogenic and anti-collagenolytic activities of the latter indicates that an anti-matrix metalloprotease activity is present therein. Other proteases including other matrix metalloproteases have been tested for their putative role as targets for the cartilage extract. By fluorometric assays, strong inhibition has been observed against gelatinolytic and elastinolytic activities for gelatinase A (MMP-2), gelatin B (MMP-9) and against the elastinolytic activity of metalloelastase (MMP-12), porcine pancreatic elastase (PPE) and human leucocyte elastase (HLE). Zymography also revealed a strong inhibition of gelatinolytic activity of MMP-2 and MMP-9 and of caseinolytic activity of MMP-12. No inhibition was measurable against urokinase and plasmin proteolysis, which indicates a specificity of the inhibitory activity against matrix-degrading proteases. The gelatinolytic activities of a variety of molecules are inhibited by the cartilage extract (amongst them, MMP-7, MMP-13, papain). The cartilage extract comprises an inhibitor capable of binding antibodies directed against human tissue inhibitors of metalloproteases (TIMPs). These results suggest that the cartilage extract comprises TIMP-like inhibitors. A TIMP crossreactive molecule of molecular weight of about 31 KDa has been identified in the liquid cartilage extract by Western blotting (see FIG. 32). The 31 KDa entity strongly reacts with anti-TIMP-2 antibody, but also with anti-TIMP-1 and -3 antibodies. Serine elastases like PPE and HLE are inhibited by the cartilage extract, while TIMPs are ineffective against serine elastases. Therefore, a TIMP-like inhibitor as well as a serine elastase inhibitor appear to be present in the cartilage extract. The cartilage extract is a more potent inhibitor of the elastinolytic activity than of the gelatinolytic activity of elastase, MMP-2 and MMP-9, which suggests that it comprises an analogue of elastin.

Ex vivo Assays

Embryonic Vascularization Test (EVT)

Definition of the Best-System: The normal development of the chick embryo involves the formation of an external vascular system located in the vitelline membrane that carries nutrients from the vitellus (yolk of an egg) to the developing embryo. When placed onto the vitelline membrane, anti-angiogenic substances can inhibit the blood vessel development that occurs in the vitelline membrane. To facilitate access to the vitelline membrane, chick embryos are transferred to a sterile culture box (Petri dish) and placed in a humidity- and temperature-controlled incubator. Embryos can then develop in this ex ovo condition for several days.

An aliquot of liquid cartilage extract is mixed with a methylcellulose solution and allowed to air-dry into thin discs. During this procedure, intrinsic NaCl present in the liquid cartilage extract interferes with the EVT when the amount of liquid cartilage per disc is over 25 µg. Therefore, desalinating the liquid extract may be necessary. Dialysis with a membrane cut-off smaller to 100 Daltons or electrodialysis have been found acceptable methods.

Methylcellulose forms an inert matrix through which the liquid extract can diffuse slowly. Methylcellulose discs containing the liquid extract are placed on the external border of the vascular perimeter of the vitelline membrane where the angiogenic process is still active.

The effect of discs-containing liquid cartilage extract on proximal vascular development is always compared to that of discs-containing water plus equimolar amount of NaCl. The discs are placed on the embryo's vitelline membrane on Day 0 or Day 1 of the ex ovo growth process; at this point, only beginnings of the main blood vessels are invading the vitellus. The embryos are then put in culture conditions until vascularization is assessed (approximately 24 h). Water- and liquid extract- containing discs are always simultaneously added on the vitelline membrane of the same embryo. Both discs are arranged in a symmetric fashion with respect to the cephalo-caudal axis of the embryo in order to minimize inter-individual variations when comparing shark cartilage extracts with controls.

Anti-Angiogenic Activity: EVTs were performed using different concentrations of protamine (37, 75 and 150 µg) as a positive control or liquid cartilage extract. After one day of culture, the level of vascularization in the area covered by the disc is graded by a pair of scientists in the usual blind fashion. To facilitate the location of the discs, a black O-ring is placed around it just after its deposition on the vitelline membrane. Evaluation scale for the EVT-test is based on the 1-2-3 score (score=3). Normal vascularization when compared to the opposite horizontal quadrant or the matching quadrant of a control embryo (score=2). Blood vessels enter the area covered by the disc, but vanish at mid-course. Major blood vessels cross the area covered by the disc but their trajectory is clearly affected or a decrease in the lateral branching density is observed (score=1). No blood vessels are observed in the area covered by the disc, or their path is rapidly deviated to avoid the area covered by the disc. Blood vessels do not grow beyond the area covered by the disc except if they bypass the latter and go beyond it.

Figure 10:
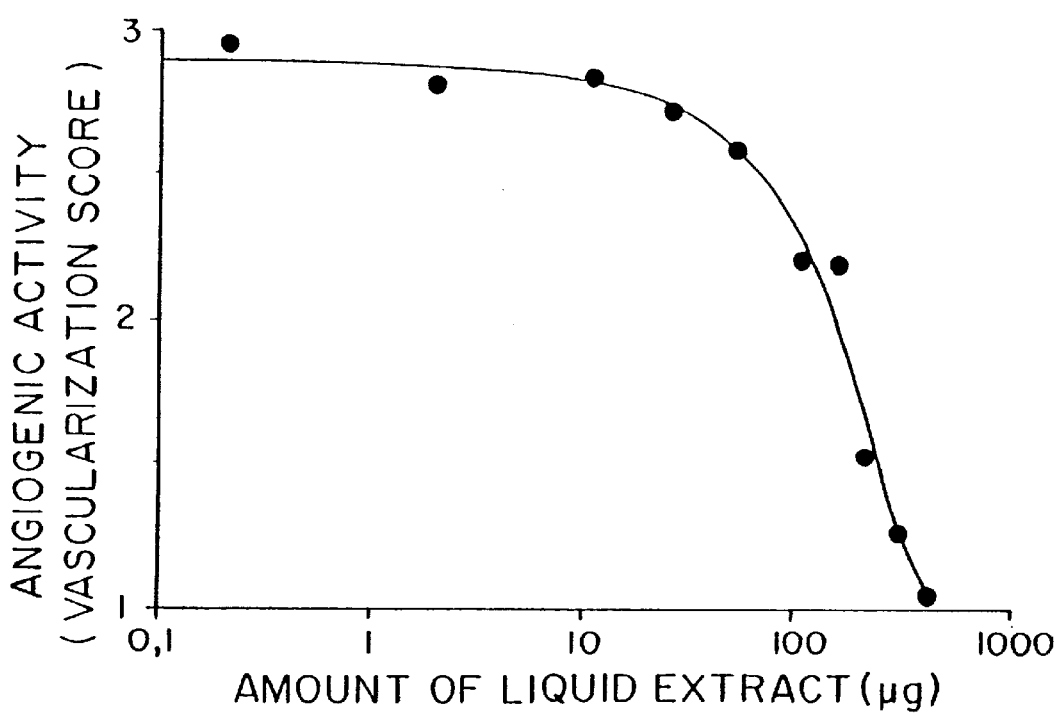
FIG. 10 shows a dose-response curve inhibition of liquid cartilage extract on the Embryonic Vascularization Test (ex ovo).

A dose-response inhibition was obtained with protamine (data not shown) and the liquid cartilage extract (FIG. 10). The ED50 was obtained with about 170 µg of dry liquid extract (dry weight present in the liquid extract) Wilcoxon-signed rank statistical test was used to compare the significance of the differences between the two discs (water and liquid cartilage extract) placed on the same egg.

Mouse Mammary Adenocarcinoma Model

Description of the Test-System: The anti-tumor potential of the liquid cartilage extract was tested with a mouse mammary adenocarcinoma model (allograft). The test-system consisted to subcutaneously inoculate BALB/C mice with 1×10⁶ DA3 cells. These cells originate from a murine mammary adenocarcinoma induced by 7,12-dimethylbenzanthracene (DMBA). The model was established by Daniel Medina (1969) (J. Natl. Cancer Inst. 42: 303–310; ibid. (1976) 57: 1185–1189). Inoculated cells slowly grow in vivo and form a solid tumor with a low metastatic prognosis.

DA3 cells were maintained in RPMI 1640 medium supplemented with 1 mM mercaptoethanol, 1 mM Hepes buffer solution, 100 mM Na pyruvate, 200 mM L-glutamine, 10 mM nonessential amino acids, 1 M vitamins, 10% fetal bovine serum, 1% penicillin-streptomycin at 37° C. with 5% $CO_2$. For tumor induction, cells were grown to 70% confluence in complete medium and then collected using trypsin-EDTA solution. Cells were then centrifuged and washed three times with phosphate buffer solution, and resuspended at a dilution of 1×10⁶ cells/0.1 ml.

DA3-cells inoculated mice (n=15) received daily oral administration of a shark cartilage liquid extract or a placebo (saline solution). The treatments began 7 days after DA3 cells inoculation. Various concentrations of liquid extract were tested. The amount of liquid extract administered is expressed with the amount of dry weight present in the liquid extract. The test articles were prepared as described here: liquid extract was lyophilized and resuspended in water at various concentrations (0.2, 1.5, 3, 10, and 20 mg per 200 µl). The final doses that were administered daily were 10, 75, 150, 500, and 1000 mg/kg of body weight.

Anti-Tumor Activity: Results show that the maximum inhibition of tumor progression was obtained with the oral administration of about 75 mg/kg of liquid extract (FIG. 11). Interestingly, larger doses were less potent. This suggests that the liquid extract contains substances that can inhibit tumor progression and other substances that can inhibit the action of the tumor inhibitors. This phenomenon has already been reported for biological drugs.

Finally, intraperitoneal administration of (1 mg/kg) liquid extract shows the same anti-tumor activity as an oral dose of about 75 mg/Kg.

Toxicity: With all treatments there was no loss in body weight or liquid extract-related death. There were no symptoms or behaviour changes observed with daily examination of mice during the treatment period. At the end of the treatment, mice were sacrificed and the gross morphology of all organs was analyzed by a certified pathologist; no abnormality was detected. Blood analyses did not show any sign of abnormality.

Histopathology: Tumor histopathology did not reveal any gross changes between tumor from placebo- or liquid extract-treated mice. The extent of tumor viability was quite high in all groups. Analysis of various organs (lung, liver, kidney, pancreas, stomach, intestine, ovary, breast, brain, and heart) did not reveal any specific alteration that can be related to the liquid extract.

Mouse Hypersensitivity Model (CHS)

Description of the Test System: Dinitrofluorobenzene (DNFB) is a powerful skin irritant that can induce a strong inflammatory reaction in BALB/C mice. The liquid cartilage extract was tested to examine whether it could reduce the inflammation response to DNFB in mouse.

At day 0, 10 mice were sensitized by painting their belly with 25 µl 0.5% DNFB. Mice were challenged on the right ear by painting 10 µl 0.2% of DNFB 5 days after sensitization. Ear swelling was measured over several postexposure times as an index of tissue irritation.

Results

Oral administration of shark cartilage extract (0–500 KDa 0.2 mL per day) during 5 to 8 days prior to sensitization reduced by 37–64% the inflammatory response. The extract administered after exposure to irritant, e.g., during the elicitation or challenge phase, did not have any significant effect on the inflammatory response. We have further demonstrated that the liquid extract decreased the level of pro-inflammatory cytokine in mRNA such as IFN-γ and TNF-α in lymphatic nodes as well as IL-1α in skin of mouse DNFB hypersensitivity model (see below) following the p.o. administration of about 175 mg/kg/day of the liquid extract. Interestingly, an increased expression of anti-inflammatory cytokines such as IL-10 was observed in skin as well as in lymph nodes. These results, along with the results obtained in acne and psoriasis cases, confirm that the inflammatory response is observed with per os as well as with topical compositions comprising a shark cartilage extract. The anti-inflammatory activity therefore shows an oral bioavailability.

Preparation of Liquid Fractions Containing Active Molecules

In vitro Assays

Tumor Cell Lines

Preparation of Test-System: Shark cartilage was harvested and processed the same as described above. After centrifugation, the pellet was discarded and the supernatant was ultrafiltrated as described, up to the sterile filtration on 0.22 p-m filter. The so obtained liquid extract was further fractionated by different methods. Tumor cell lines were grown as described in above section.

FPLC Conditions: Column Hiload 26 mm×60 cm Sephacryl S-300. FPLC system: from Pharmacia. All samples were filtered on 0.22 µm filter before loading on the column. The elution buffer was phosphate buffer saline (PBS) filtered and degazed during 15 minutes. The volume of the loaded sample was usually 3.2 mL (could be up to 13 ml). The flow rate was 1 ml/minute. Fractions of 10 mL were collected. The eluted compounds were detected by their U.V. absorbance (280 nm). A calibration chart was obtained by using the MW-GF-1000 calibration kit from Sigma, this calibration sample having the same volume as the loaded sample to analyze (3.2 ml). The elution volume of a sample was deduced from the plotting of the molecular weight of the compounds of the calibration kit versus their elution volume to which was subtracted the void volume of the column. The void volume was obtained by injecting dextran blue (MW= 2,000,000).

The fractions were tested on ZR75-1 cells for their activity. The fractions of interest were identified and their characteristics were corroborated by further study, described below.

Additional characterization of the active components of the permeate was conducted on Rotofor (BioRad 170-2950; see isoelectrofocalization below) and on Amicon filters of different cut-off values to obtain fractions of molecular weight between 10–30 kDa, 30–100 kDa and over 100 kDa.

Isoelectrofocalization Conditions: A preparation of shark cartilage liquid extract (46 mL of 1 Kg/L) was dialysed overnight against 4 liters of pure water containing 5% glycerin at 4° C. using a membrane Spectra pore #7 MWCO 3500 kDa (Spectrum 132110). The dialyzed solution was mixed with 2.75 mL of ampholytes (Pharmacia #80-1125-87) pH 3.5–10.0 and 0.5 g CHAPS (Sigma C3023; 3-[(3-Cholamidopropyl)-dimethylammonio]-1-propane-sulfonate). The volume was completed to 55 mL with pure water. The solution was loaded on Rotofor and isoelectrofocalization was conducted at 4° C., at a constant power of 12 watts (3000 xi power supply BioRad 165-0554), under constant water circulation for insuring maintenance of the temperature. At the beginning of the separation, the voltage was 380 volts and the amperage 31 mA. When the amperage was stabilized (at 14 mA), the voltage read 870 volts. The isoelectrofocalization was stopped and 20 fractions were collected.

TABLE 5

| FRACTION | VOLUME (ml) | pH |
|---|---|---|
| 1 | 3.7 | 3.56 |
| 2 | 2.1 | 4.01 |
| 3 | 2.2 | 4.18 |
| 4 | 2.3 | 4.31 |
| 5 | 2.2 | 4.63 |
| 6 | 2.1 | 5.03 |
| 7 | 2.5 | 5.30 |
| 8 | 2.1 | 5.5 |
| 9 | 2.4 | 5.81 |
| 10 | 2.5 | 6.26 |
| 11 | 2.3 | 7.00 |
| 12 | 2.4 | 7.29 |
| 13 | 2.4 | 7.64 |
| 14 | 2.5 | 7.94 |
| 15 | 2.3 | 8.32 |
| 16 | 2.5 | 8.62 |
| 17 | 2.4 | 8.94 |
| 18 | 2.9 | 9.30 |
| 19 | 3.1 | 9.88 |
| 20 | 3.6 | 10.71 |

The identification of these proteins was made by estimating their molecular weight on an electrophoresis gel (Laemmli, U.K. (1970) Nature (Lond.) 227: 680).

Figures 13A, 13B:
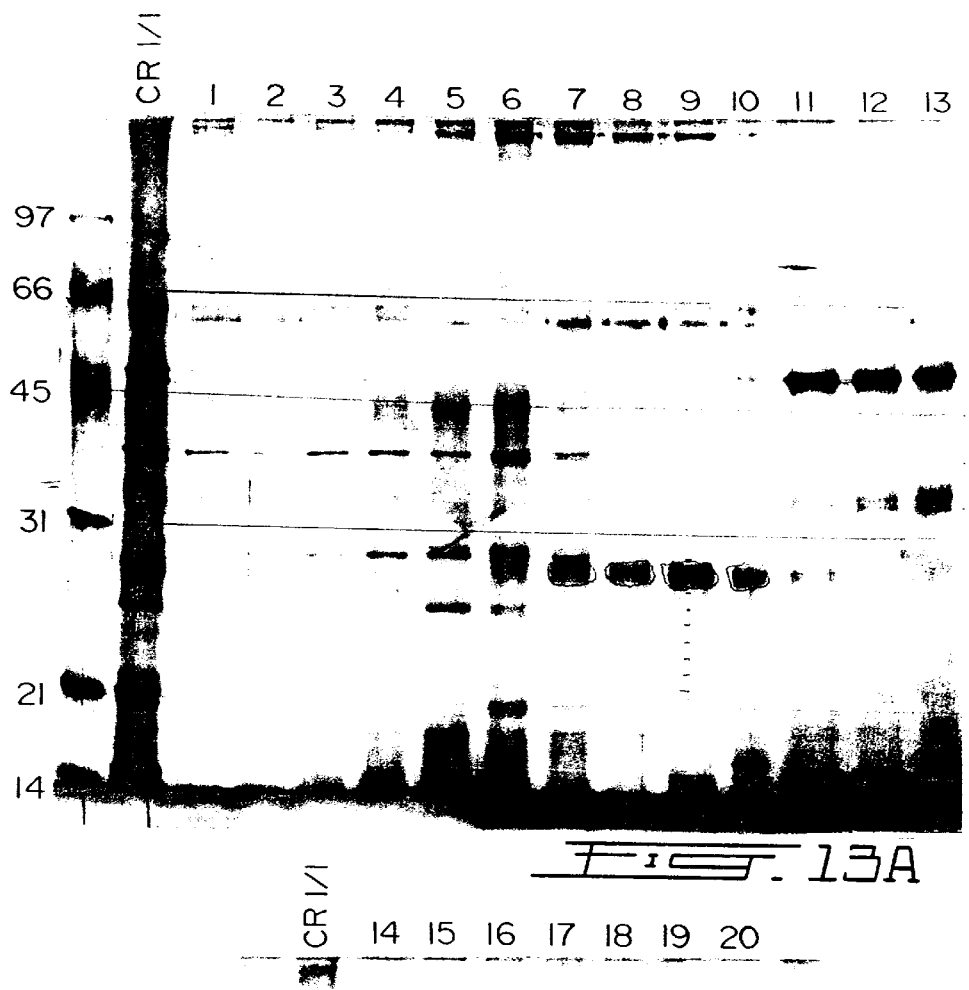
FIG. 13 represents the electrophoretic profile in non-denaturing conditions of liquid fractions separated on Roto-for; molecular weight markers appear at the left followed by a sample of liquid extract before fractionation, for comparison with the isolated fractions.

These fractions were four-fold diluted with a loading buffer (see Laemmli) and 8 μL aliquots were submitted to electrophoresis in non-reducing conditions. FIG. 13 shows the electrophoretic profile of each fraction and of the material before isoelectro focalization.

All the fractions were sterile-bottled under a laminar flow hood by passing them through a sterile Millipack-60 filter having a porosity of 0.22 μm.

d. Inhibitory Activity on Tumor Cells: Liquid cartilage extract were tested on ZR75-1 cells at different concentrations in culture medium. The protein content of the fractions was evaluated by the Lowry dosage method. The results are summarized as follows (Tables 6, 7, and 8):
1st Test: Tests performed on Rotofor fractions (the liquid cartilage extract was concentrated by evaporation).

Protein Identification

TABLE 6

| Fractions Identified | Isoelectric Point | Median Value | Molecular Weight |
|---|---|---|---|
| 7-8-9-10 | 5.30 to 6.26 | 5.78 | 29 +/− 1 kDa |
| 7-8-9 | 5.30 to 6.26 | 5.68 | 60 +/− 1 kDa |
| 12-13-14 | 7.29 to 7.94 | 7.62 | 48 +/− 1 kDa |
| 13-14 | 7.64 to 7.94 | 7.79 | 35 +/− 1 kDa |

2nd test: Tests performed on FPLC fractions (the permeate was concentrated by evaporation):

TABLE 7

| Fractions | Molecular Weight |
|---|---|
| 6 and 7 | 0.1–2.5 kDa |

3rd test: Tests performed on 100 μl fractions obtained on Amicon molecular filters:

TABLE 8

| Concentration tested | Molecular Weight | Inhibition of ZR75-1 Cell Cultures |
|---|---|---|
| 100 μg/ml | MW > 100 kDa | 64% |
| 100 μg/ml | 30 kDa < MW < 100 kDa | 114% |
| 100 μg/ml | 10 kDa < MW < 30 kDa | 127% |
| 400 μg/ml | MW < 10 kDa | 149% |

FPLC fractions 6 and 7 contain active components of a very small molecular weight: 0.1 to 2.5 kDa.

The hypoplasiant effect of the fractions can be up to 33 000 times higher than the one observed with the solid extract.

e. Further Identification of the Active Components of the Eluate: The active fractions (tested on ZR75-1 cells) are retrieved in the following range of molecular weight, determined by another type of purification starting with the same liquid extract (1 kg/L) on a 10 mm diameter×30 cm length Superose-12 column using the FPLC and rotofor procedures described above. A flow rate of 1 ml/min was selected. Forty-five 45 fractions of 1 mL were collected.

TABLE 9

| Fractions 20–21 | activity in fractions corresponding to a molecular weight of 70 to 120 kDa |
| Fraction 22 | activity in fractions corresponding to a molecular weight of 60 to 70 kDa |
| Fraction 29–32 | activity in fractions corresponding to a molecular weight of 35 to 46 kDa |
| Fraction 34–35 | activity in fractions corresponding to a molecular weight of 29 kDa |
| Fraction 38–39 | activity in fractions corresponding to a molecular weight of 0 to 2.5 kDa |

Collagenase Assay

HPLC Chromatography: A 980 mL sample of liquid extract (DUP) was filtered through a 10 kDa cutoff membrane in a tangential flow ultrafiltration unit (PELLICON, Millipore). The unit was first rinsed with 1 L of water. Final yields were 480 mL of >10 kDa fraction and 1.8 L of <10 kDa fraction. The <10 kDa was concentrated by cold-finger evaporation to 180 mL (<10–10×). Eight times 100 μl aliquots of <10–10× were loaded onto CDC-S Hexyl, 5 μm HPLC column (25×0.94 cm) and eluted first with 100% $H_2O$ at 4 ml/min; then at 8.5 ml/min with 100% MeOH. Fractions were collected corresponding to $OD_{214}$ peaks.

Figure 14:
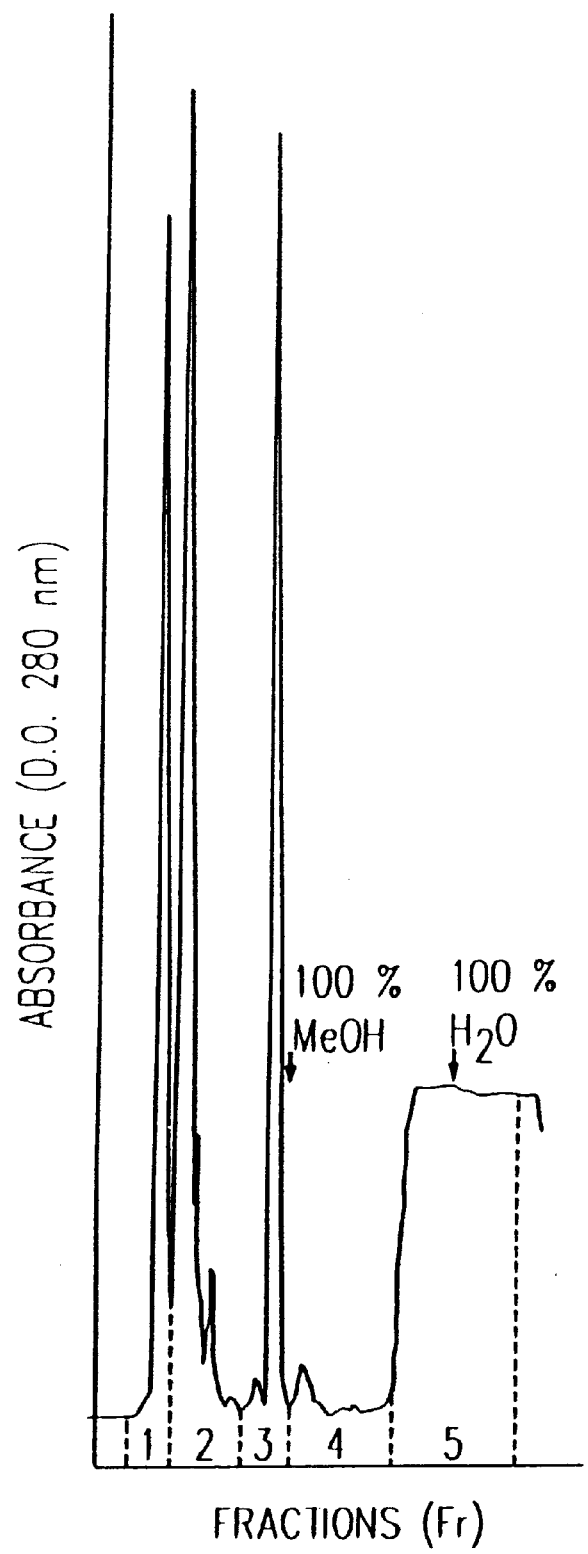
FIG. 14 shows a HPLC migration pattern of a fraction of the liquid extract of this invention having molecular weight lower than 10,000 Daltons, which fraction has been concentrated and separated in five sub-fractions.

Five fractions were collected (FIG. 14): Fr1, Fr2, Fr3, Fr4, and Fr5. The first three fractions include at least a major peak.

Anti-Collagenolytic Activity: Two collagenase assays have been performed to verify which fraction was the most active to inhibit collagenase. The first assay is the one performed above, which makes use of a fluorogenic peptide substrate (Knight et al. op. cit.). The second collagenase assay is described in Welgus et al. (1979) J. Biol. Chem. 256: 9511–9516. The method uses SDS-PAGE to examine cleavage by collagenase type 1 (MMP1). Collagenase type 1 makes a single cut in the native collagen molecule giving two fragments of 75% and 25% the size of the original collagen. After cleavage for several hours, the reaction is monitored by separating the products from the substrate by SDS-PAGE. The ratio of cleaved to uncleaved collagen is assessed visually after staining the gels with Comassie blue (or silver stain).

Results

The results show that Fr1 is the most active fraction to inhibit the collagenase; a lower level of activity is present in all other fractions. These results are confirmed notwithstanding the assay that has been used (fluorogenic assay, see FIG. 14; second assay, see Table 10).

TABLE 10

| SAMPLE | COLLAGEN STAINING | COLLAGEN FRAGMENT STAINING |
| --- | --- | --- |
| Collagen only (C) | ++++ | − |
| C + Enz | + | +++ |
| C + Enz + EDTA | ++++ | − |
| C + Enz + DUP | + | ++ |
| C + Enz + Fr1 | ++++ | − |
| C + Enz + Fr2 | +++ | + |
| C + Enz + Fr3 | +++ | + |
| C + Enz + Fr4 | +++ | + |
| C + Enz + Fr5 | +++ | + |
| C + Enz + >10 kDa | + | +++ |

EDTA 40 mM inhibited collagenase. The total liquid extract DUP showed a low anti-collagenolytic activity. Fractions 1 to 5 were active; the most active was fraction 1. The fraction of a molecular weight higher than 10 kDa showed no significant inhibitory activity. Therefore, an anti-collagenolytic activity is assigned to molecules having less than 10 KDa.

As mentioned above, the present cartilage extract comprises at least two types of inhibitors, one type against matrix metalloproteases MMP-2, -9 and -12, and another type against serine elastases. Thus, although no anti-collagenase activity has been retrieved in the fraction>10 KDa, other inhibitors appear to be present in this high molecular weight fraction.

Ex vivo Assay

Embryonic Vascularization Test (EVT)

Figure 15:
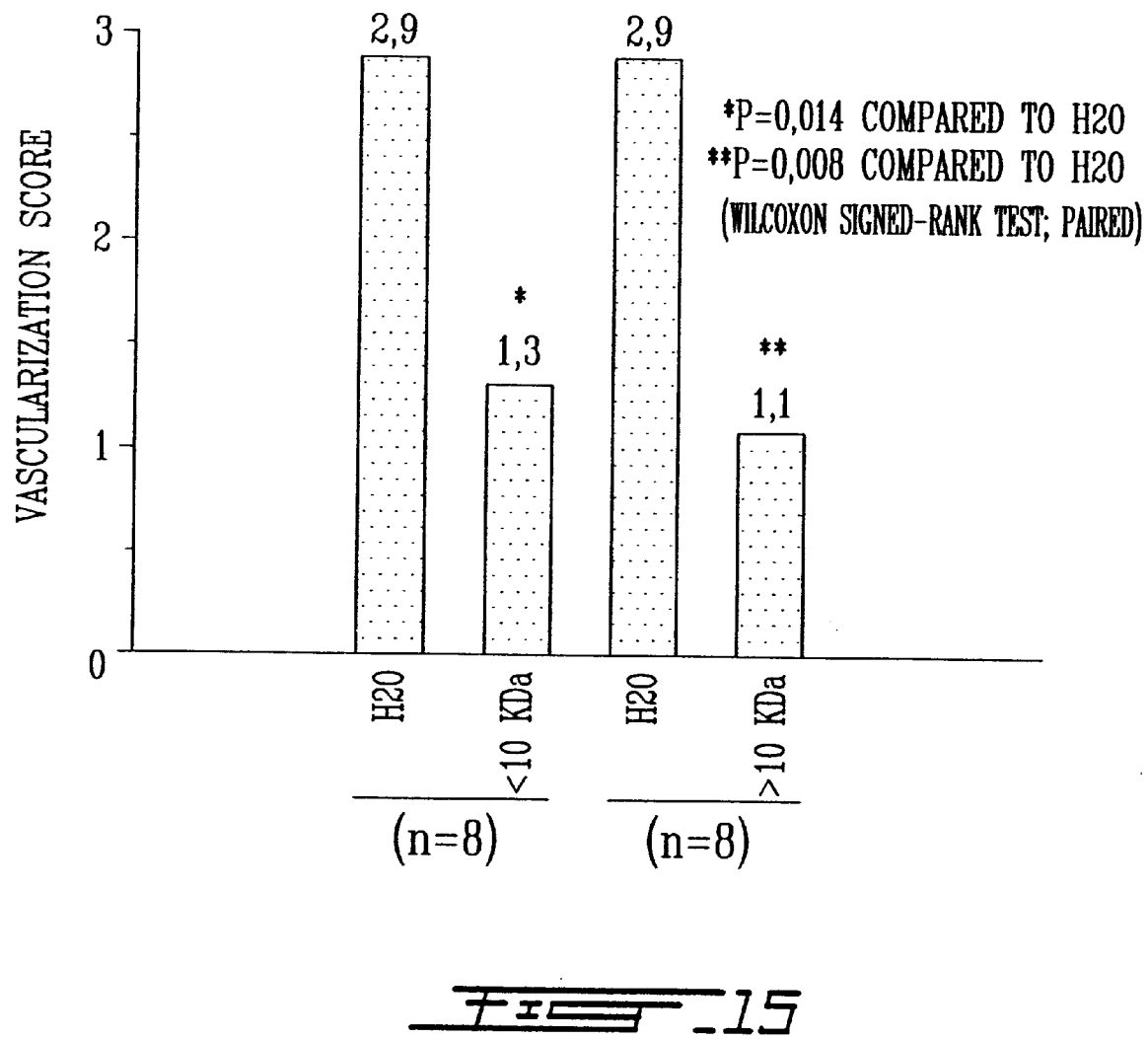
FIG. 15 shows the EVT results obtained with two fractions of liquid extract of shark cartilage of our invention (DUP), one having molecular weight lower than 10,000 Daltons, the other one having molecules higher than 10,000 Daltons.

The liquid cartilage extract was fractionated using a tangential flow filtration apparatus and a 10 kDa filter (Pellicon, Millipore). The lower and higher than 10 kDa fractions of the liquid cartilage extract were tested in the same conditions. They were shown equally potent (FIG. 15) in inhibiting neovascularization. This contrasts with the anti-collagenolytic activity which does not appear to be present in the fraction over 10 kDa. Thus the anti-angiogenic activity is due at least in part to molecules different from an anti-collagenase, e.g., other metalloproteases or other unrelated molecules.

Fraction<10 kDa: The anti-angiogenic factor in this fraction behaved as the anti-collagenolytic factor during the purification steps described above.

Fraction>10 kDa: The fraction was chromatographed on a gel permeation chromatography column (Sephacryl S-300, Pharmacia). A fraction (S300-4) having anti-angiogenic activity was characterized on SDS-PAGE. The active fraction (S300-4) had several protein bands having molecular weights of between approximately 8 and 18 kDa (compared with BioRad SDS-PAGE marker proteins). This fraction was further fractionated using anion exchange chromatography (Mono-Q, Pharmacia) using 25 mm Tris-HCl pH 8.0 and a 0 to 1.0 M NaCl gradient. A fraction eluting at between 0.8–1.0 M NaCl had high anti-angiogenic activity. Fractions eluting between 0.3–0.6 M NaCl and 0.08–0.2 M NaCl had lesser anti-angiogenic activity.

Since we are not the first to find a great interest in cartilage extracts, we have verified the unique character of the shark cartilage liquid extract prepared by the present process in side-by-side comparison tests with two products described or deducible from the prior art, namely products prepared by the process of Balassa (U.S. Pat. No. 4,822,607) and Oikawa et al. (op. cit.).

Oikawa et al. describe a method by which two main fractions are obtained, one having molecules of molecular weights comprised between 1 and 10 kDa, the second having components heavier than 10 kDa. They assign anti-angiogenic properties only to the first fraction, the other being said devoid of any anti-angiogenic activity in CAM test. For adequate comparison of Oikawa's products, we have fractionated our total liquid extract in two corresponding fractions, and we retained the one having 0 to 10 kDa.

Since Balassa describes a process for extracting a total liquid extract, we have compared our liquid cartilage extract (0 to 500 kDa) to the product prepared by reproducing Balassa's method, replacing the calve cartilage by shark cartilage as the starting material.

We assume that if Balassa and Oikawa describe a process equivalent to ours, the patterns obtained on FPLC, HPLC, and CZE should overlap substantially, and the same anti-angiogenic activity should be revealed on EVT. All samples were made to a final concentration of 12 $\mu$g/$\mu$L (dry weight/volume solution) prior to FPLC and HPLC chromatography. Oikawa's product was centrifuged and filtered prior to chromatography because it contained insoluble material.

Samples Preparation

Figure 18A:
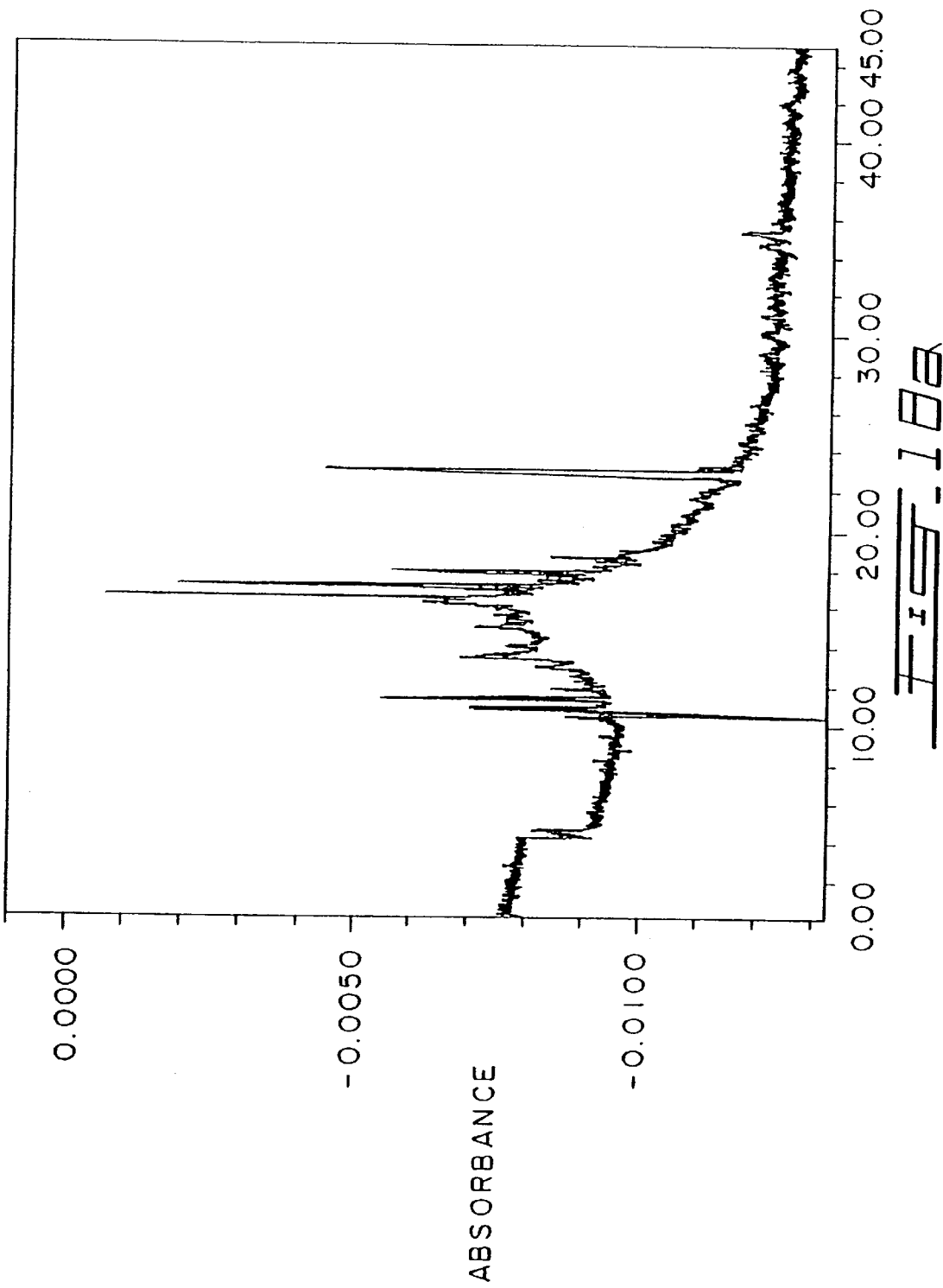
FIG. 18 shows a CZE comparison of the liquid cartilage extract of the present invention with the prior art.
Figure 18B:
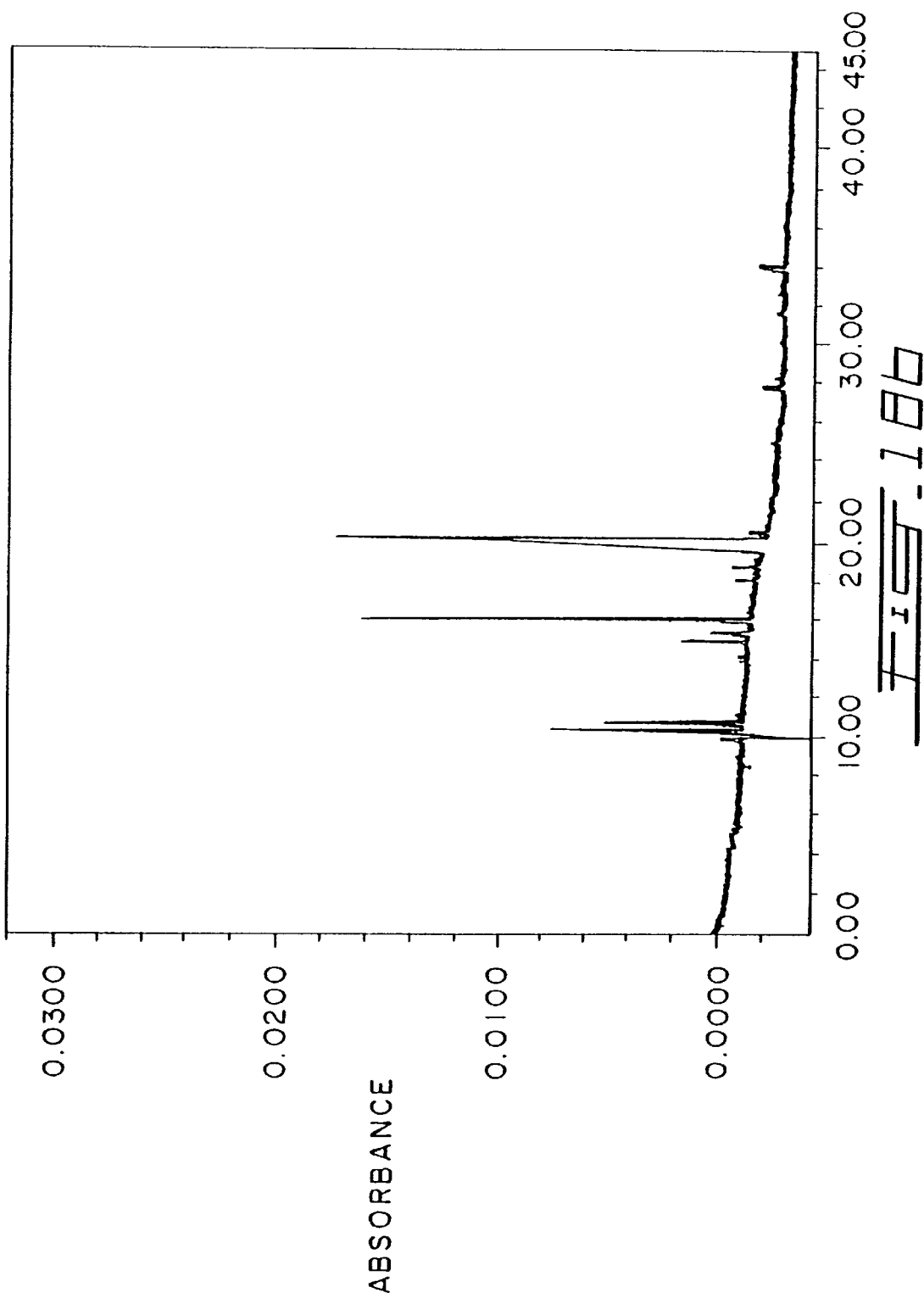
Figure 18C:
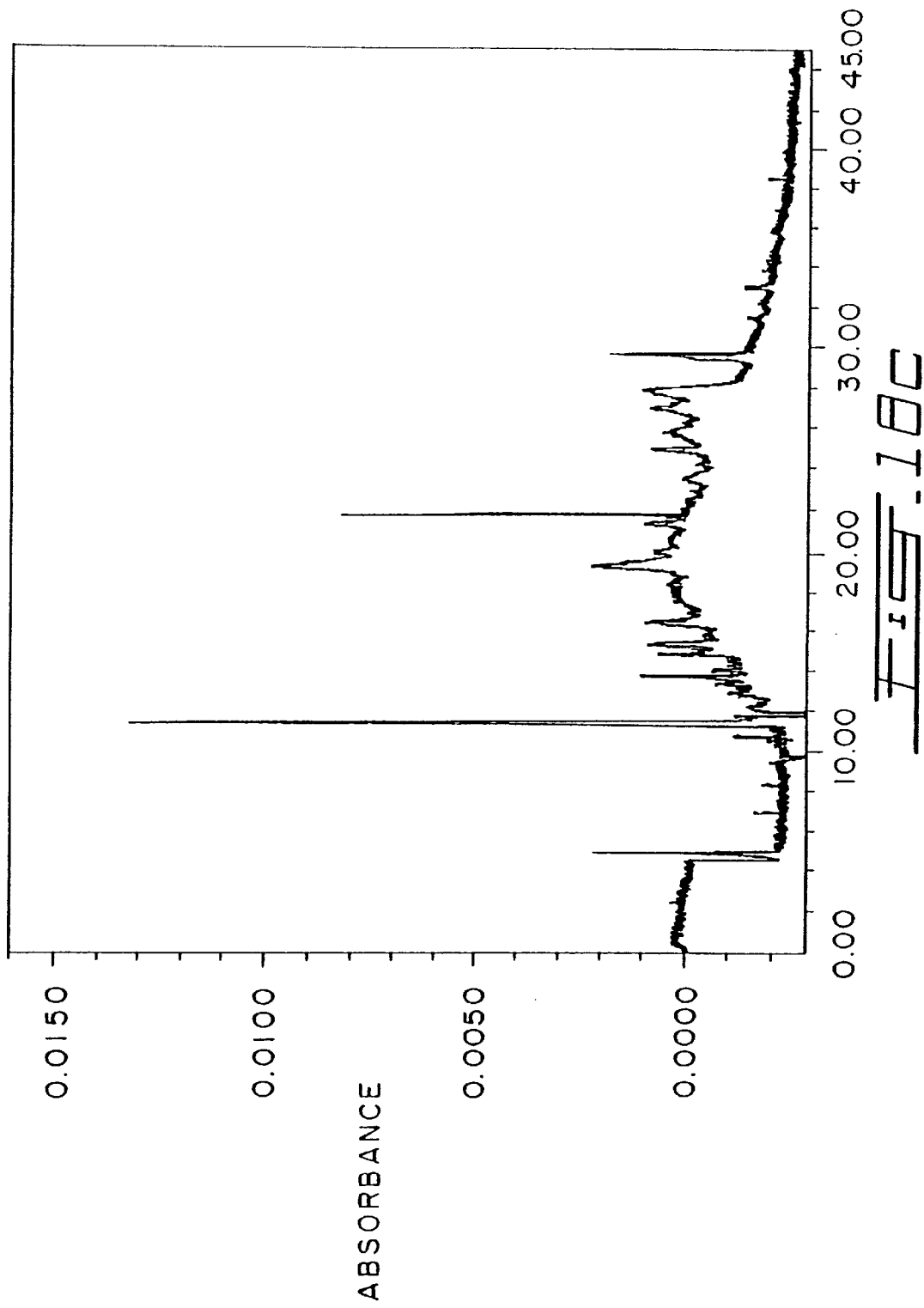

Shark cartilage samples extracted by the three methods were labelled (with estimated dry weight per volume of solution) as follows:

1) DUP is the preparation of the present invention fractionated to contain molecules between 0 to 500 kDa (12 $\mu$g/$\mu$L);
2) BAL is the preparation according to the recipe of Balassa et al. (12 $\mu$g/$\mu$L);
3) OIK is the preparation of fraction 3 according to Oikawa et al. All samples were made to a final concentration of 12 $\mu$g/$\mu$L (dry weight/volume) prior to any analysis. The OIK sample had a high amount of insoluble material that could be pelleted readily by centrifuging at 13,200 RPM or filtering through a 0.2 $\mu$m membrane. Removal by filtration of insoluble material was essential prior to FPLC, HPLC, and CZE (FIGS. 16, 17, 18).

FPLC Comparison

Conditions

Samples were run on a Superose 12 (10/30) gel permeation column with phosphate buffered saline (PBS) as elutent at a flow rate of 0.5 ml/min (chart speed=0.25 cm/min). A 100 μl aliquot of the concentration adjusted samples was filtered through a 0.2 μm membrane before injection. $OD_{280}$ was monitored.

The column was calibrated with the following standards (MW in Daltons): catalase (232,000), aldolase (158,000), albumin (56,000), ovalbumin (44,000), chymotrypsin (25,700), ribonuclease (13,700), insulin (5,700), insulin B chain (3,500), insulin A chain (2,500) bacitracin (1,450), vitamin B-12 (1,355). Molecular weights of the major peaks were calculated by the following equation: $\log_{10} MW = 7.52 - 0.212 \times RT$, where RT=elution volume in mL. $R^2 = 0.976$. Total column volume (Vt) was 21.93 mL as determined using cytidine (246 Daltons). Void volume (VO) was determined to be 8.38 mL with blue dextran ($2 \times 10^6$ Daltons).

Results Summary

In FIG. 16a, our sample (DUP) had a first major peak (1) which eluted at 18.76 mL giving a molecular weight of about 3,500 Daltons. Subsequent peaks at 22.7 (2) and 27.3 mL (3) were beyond the total column volume (21.93 ml, as determined by cytidine). These peaks appear to have some affinity for the column matrix.

In FIG. 16b, Balassa's sample (BAL) had a small peak (1) eluting near the Vo of the column (8.4 ml), a peak (2) at 18.5 mL (4,000 Daltons) and two peaks eluting after the Vt(3) 22.6 min and (4) 28.2 ml.

In FIG. 16c, Oikawa's sample (OIK) also had a small peak (1) at the Vo, peak (2) at 18.9 mL (3,300 Daltons), peak (3) at 21.5 mL (1,000 Daltons) and small peak (4) at 27.3 ml.

In comparing the samples, it is notable that aside from the 3,500 Daltons peak, that the major bands of the DUP sample were not observed at the same intensity in the other samples. The OIK sample did appear to have a small amount of the 27.3 mL peak. The BAL sample had a peak migrating at 28.2 mL which could correlate with one of the minor peaks in the DUP sample.

HPLC Comparison

Conditions

C-S-S-hexyl column 5 μm, 25×0.94 cm, CSC #059-085; reverse phase column.

Results Summary

For HPLC on a hexyl-reverse phase column, $OD_{210}$ and $OD_{280}$ were monitored simultaneously. Fifty μl aliquots of centrifuged samples (all at 12 μg/μl) were loaded and eluted with 100% $H_2O$. Peaks for each chromatogram labelled according to $OD_{210}$ (e.g., 1) and corresponding $OD_{280}$ peaks are noted by (e.g., 1). The $V_0$ of this column was 5.5 mL (1.4 min).

In FIG. 17a, DUP had 3 major peaks that were observed via $OD_{210}$ (1,2,3) and 2 minor peaks (4,5). Two side peaks were observed off of peak 1, labelled 1a and 1b. Significant $OD_{280}$ absorbances were associated peaks 1, 1a, 1b and 3. In comparison, the corresponding $OD_{280}$ absorption for peak 2 is much smaller relative to the $OD_{210}$.

In FIG. 17b) BAL showed more $OD_{210}$ peaks, but the intensities were lower relative to the DUP peaks. As far as overlap of peaks could give an indication of identity of molecules, only peaks 3 and 7 in the BAL appear to correlate with the retention times of peaks in the DUP sample (peak 1a or 1b and peak 4, respectively).

In FIG. 17c), only three major peaks were observed (1,2,3) in OIK extract. Peaks 1 and 3 could correlate to peaks 1 and 3 of DUP sample but no side peaks of 1 were observed in the OIK chromatogram. The height of the peaks in the OIK sample were lower than the DUP. Therefore, FPLC and HPLC patterns are characteristic of distinguished products.

CZE Comparison

Conditions

Apparatus. Beckman system (p/ace system 2050) with goal software (version 7.11 U); Capillary: Silice (TSPO 50375), 50 μm×97 cm; buffer: 2 M formic acid; Coated solution, 5% p/v hexadimethrene bromide and 2% v/v ethylene glycol in water; Detector: UV (200 nm); Current: −30 kV; Injection: 0.5 psi, 20 seconds; Temperature: 22° C.

The capillary was conditioned with 1 M NaOH (20 psi, 20 min), water (20 psi, 10 min), Coated solution (20 psi, 20 min), and buffer (20 psi, 10 min). Then conditions were settled for a run: Buffer (20 psi, 2 min), sample injection (0.5 psi, 20 sec.), run (−30 kV, 45 min), 1 M NAOH (20 psi, 3.5 min), water (20 psi, 3.5 min.), coated solution (20 psi, 4 min), and buffer (20 psi, 4 min.).

Each samples (BAL, DUP, OIK fraction 3) were resuspended at 16.5 mg/ml. The pH of each solution was 7.1, 6.8, and 8.2 in BAL, DUP and OIK, respectively. NaCl concentration of each solution was 2.08, 4.37, and 0.71 mg/mL in BAL, DUP, and OIK, respectively.

Results Summary

The molecular profile of each sample (BAL, DUP, and OIK-3) is shown in FIG. 18. The comparison of DUP and BAL samples showed that the BAL sample was contained a larger proportion of peaks with a % area<1. BAL and DUP share the peaks at MT/EOF=1.06, 1.54, 1.59, 1.66, and 3.22. The peaks with the ratio of 1.06, 1.54, and 3.22 have a similar % area in BAL and DUP whereas peaks at ratio 1.59 is 8 times more intense than in BAL and the opposite is seen at the ratio 1.66.

DUP and OIK samples present a very different electro-chromatogram. OIK has one major peak with several minor peaks. None of these peaks can be related to one of the DUP sample.

EVT Comparison

Figure 19:
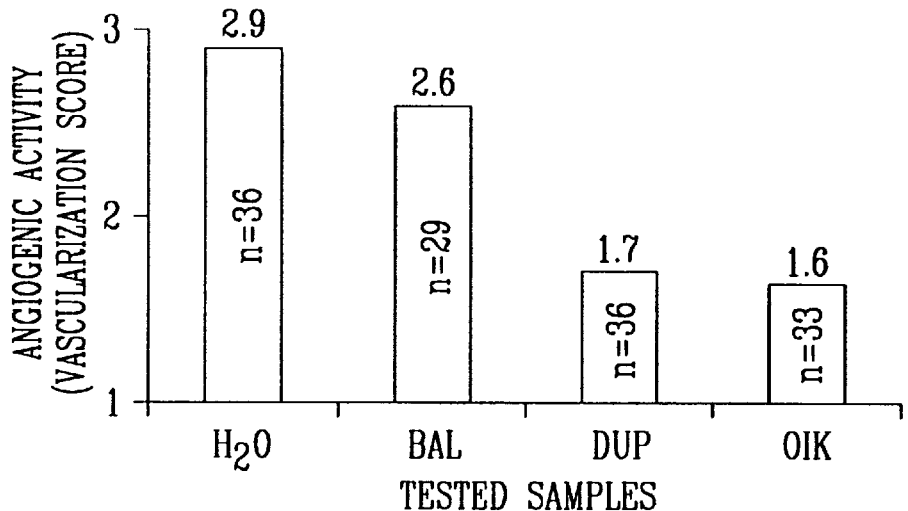
FIG. 19 shows an EVT comparison of the liquid cartilage extract of the present invention with the prior art.

The anti-angiogenic potential of the samples DUP, BAL and OIK was analyzed on EVT (FIG. 19). No significant anti-angiogenic activity was retrieved in Balassa's extract. The DUP crude extract was compared to the fraction 3 in Oikawa OIK. Both DUP and OIK were almost equivalent. Oikawa et al. nevertheless taught away from the present invention since they mentioned that no activity was detectable in the fraction of molecular weight higher than 10 kDa, which is in contradiction with our results of FIG. 15.

Therefore, despite similarities between Balassa's and our processes, the products obtained by both processes are clearly not the same.

Amino Acid Content Comparison

The protein content of BAL, DUP and OIK samples (all of 16.5 mg/mL of dry weight) was measured by the method of Lowry; results show values of 3.31, 0.27, and 4.15 mg/mL for BAL, DUP, and OIK sample, respectively. The ratio of protein/dry weight is very different when DUP sample is compared to BAL and OIK.

Figure 20A:
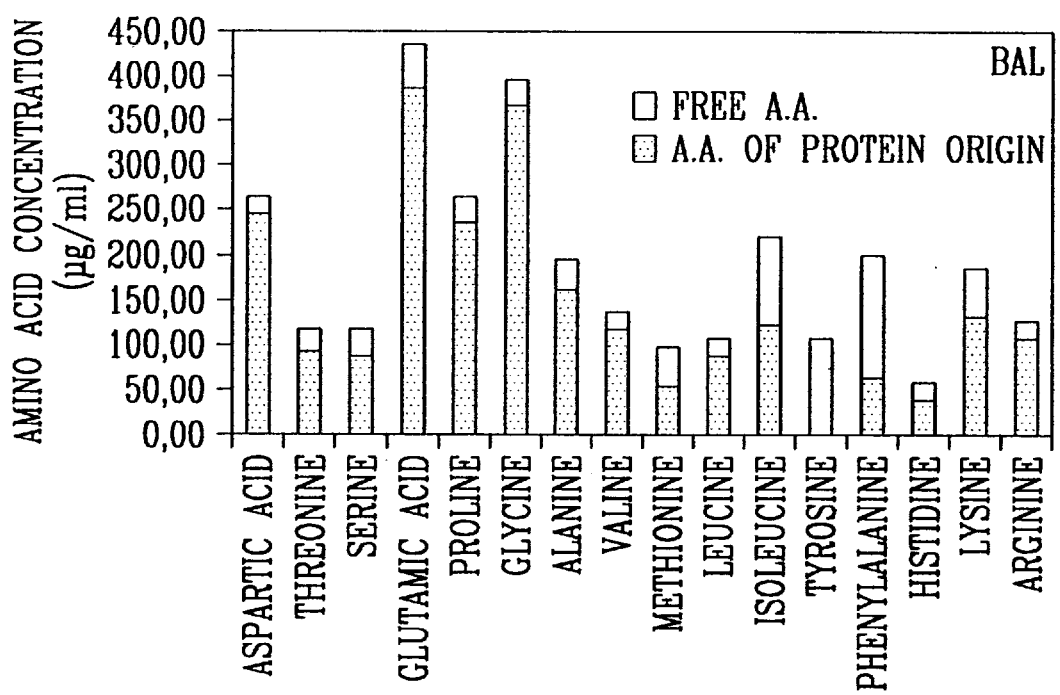
FIG. 20 illustrates a comparison of the amino acid content of the liquid cartilage extract of the present invention with the prior art.
Figure 20B:
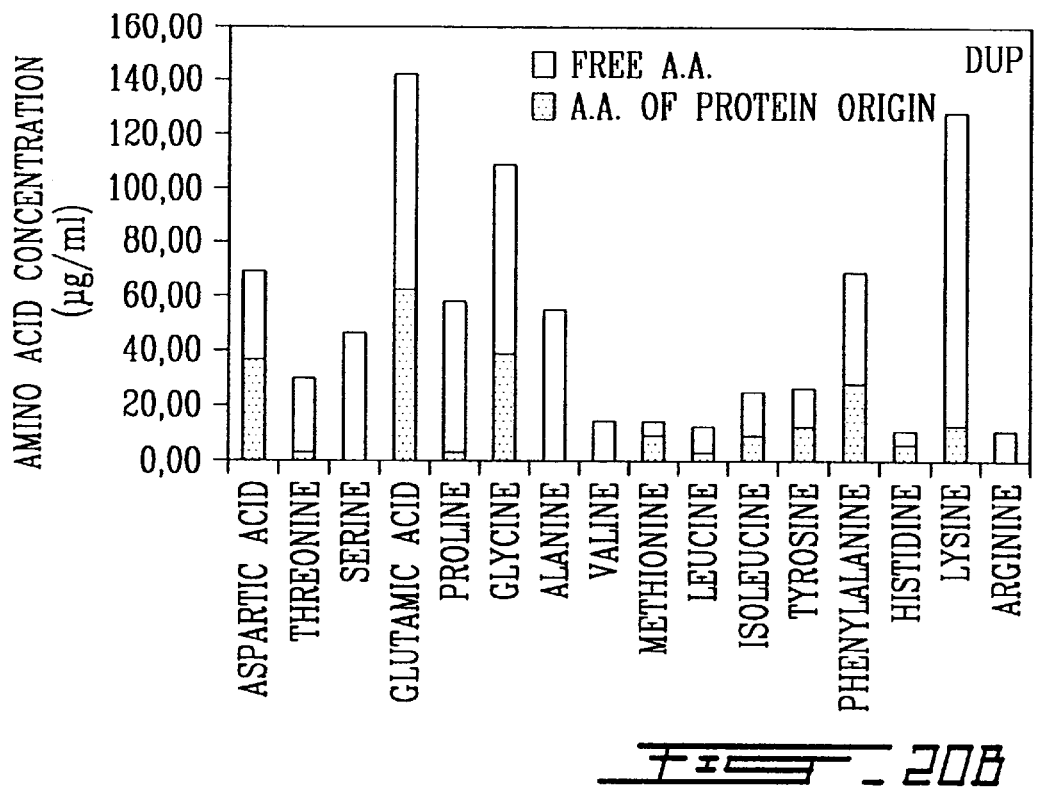
Figure 20C:
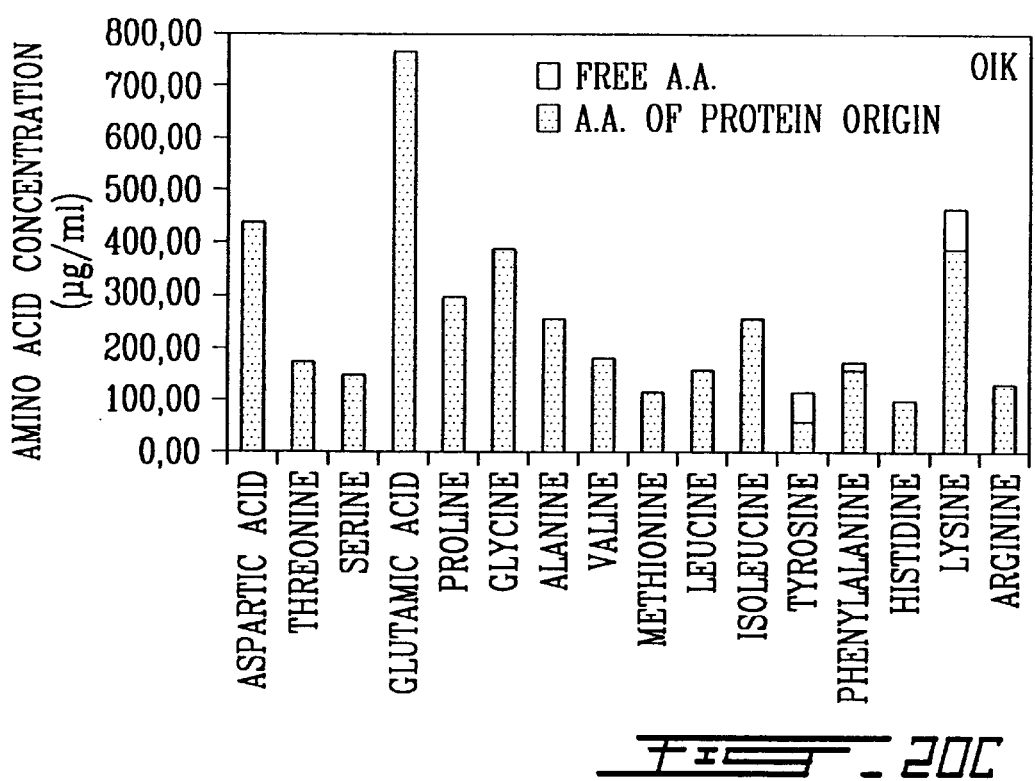

Analyses were performed to further analyze the amino acid content of each liquid cartilage preparation. FIG. 20 illustrates the proportion of each amino acid in BAL, DUP, and OIK samples. The proportion of free amino acids vary between each cartilage preparation: 23%, 73%, and 4% in BAL, DUP, and OIK samples, respectively. Obviously the proportion of amino acids from protein origin also vary between each cartilage preparation: 77%, 27%, and 86% in BAL, DUP, and OIK samples, respectively. See Table 11 for raw data:

TABLE 11

| Cartilage Preparation | Free a.a. content (µg/ml) | a.a. from protein origin (µg/ml) |
|---|---|---|
| BAL | 675 | 2314 |
| DUP | 604 | 223 |
| OIK | 181 | 3910 |

The two prior art products (BAL, OIK) that have been compared to ours (DUP) are yet considered as classical processes to prepare cartilage extracts. The above results show that the present process (DUP) provides a product of unexpectedly good activity, as far as anti-angiogenic, anti-tumor, anti-inflammatory, and anti-collagenolytic activities are concerned. We can assume that the present process has indeed succeeded in providing plural hydrosoluble biologically active components, or factors, in a single extract.

Direct comparison of BAL, DUP and OIK molecular profiles and protein content demonstrated that each cartilage preparations have particular characteristics. Although they seem to share some constituents it is evident that their ratio one to another is different. This is particularly important considering that DUP is anti-tumor when administrated orally at a dosage range below about 75 mg/kg and gradually looses this effect at higher dosage. This result suggests that the amount of more than a single factor is critical in the DUP liquid cartilage extract. Therefore, different cartilage preparations like BAL, DUP and OIK may show very different biological properties, since the protein content and the proportion of each individual component varies between them.

Preparation of Liquid Extracts for Clinical Trials

Preliminary clinical trials were performed with shark cartilage liquid extract of the present invention. The liquid extract obtained after ultrafiltration was filtered of a Millipore filter of a porosity of 0.22 µm. The microbial limit of the liquid extract was controlled according to USP XXIII <61> standard. The liquid extract was distributed in 7 mL aliquots (about 85 mg of proteins) in aseptic flasks, frozen at −60° C. overnight and further stored at −20° C. until utilization.

Anti-Angiogenic Effect

The liquid cartilage extract was used for treating angiogenesis-dependent diseases. Three different types representative of angiogenesis-dependent diseases were tested in the practice in human; the first type being cancer (prostate cancer), the second type being dermatological disorders (psoriasis and rosacea), and the third type being arthritis (rheumatoid arthritis and osteoarthritis). The examples below will illustrate and indicate at least the anti-angiogenic activity of the liquid extract.

The results shown hereinbelow are very encouraging and are deemed predictive of the usefulness of the cartilage extract and fractions thereof in the treatment of all angiogenesis-dependent diseases, and not only the ones specifically tested. Insofar as a disease has an angiogenic component, it is deemed that the cartilage extract of the present invention will be effective in this respect provided that it enters a composition containing an effective amount thereof and that this composition is in a suitable form for proper administration. Therefore, it will be appreciated that the present invention is not limited to the following specific compositions for use in the treatment of angiogenic diseases, since the person skilled in the art would be able to derive numerous compositions wherein choice is guided by the mode of administration thereof and the targeted ill tissue. Compositions may be administered by different routes, e.g., topical, oral, sublingual, rectal, intravenous, intramuscular, intraocular, intraperitoneal, by diffusion, etc.

Because of the fishy taste and smell of the cartilage extract, flavoring agents or fragrances may be added or other gallenic compositions (liposomes, encapsulation, patch, etc.) can be designed to mask any unpleasant taste or smell and to encourage patient's compliance. The term "patient" is meant to designate a human or an animal patient.

Cancer

One patient suffering of prostate cancer has added the liquid cartilage extract to its diet and shows significant health improvement since. An adenocarcinoma was diagnosed in 1986. At that time, radiotherapy was undertaken. In 1991, the PSA (prostatic serum antigen) level was 138 µg/L, when the normal acceptable higher limit is 4 µg/µL. The patient then underwent a completely different therapy by castration combined with anti-androgen therapy (EUFLEX). This treatment was efficient during three years, after which PSA level began to rise again. Since June 1994, this patient added the liquid cartilage extract to its diet (daily oral dose of about 75 mg of dry weight/7 mL of extract, equivalent to about 1–1.5 mg/kg of body weight/day). The PSA levels gradually decreased from 12 to below 4.0 µg/mL (normal limit) the last result being obtained in April 1996. This dose regimen would have to be modified at will in accordance with the route of administration, the bioavailability of the active ingredients and the desired aggressiveness with which the pathology is to be controlled. In this case, the liquid extract is probably absorbed in the gastrointestinal tract in substantial proportions. One can rely upon the results obtained with DMBA-treated rats and inoculated mice (see above). At this time, the non-toxicity has been verified in rat, mouse (see above examples), and monkey (data not shown).

Oral administration of the liquid extract in DMBA-treated rats and DA3-implanted mice suggest a dosage rate between 1 to 300 mg/kg of body weight, which presumably had a great contribution to the inhibition of tumor progression and tumor vascularization in animal models. Intraperitoneal administration of the liquid extract in mice (DA3-model) demonstrated that the route of administration is important to obtain an effective dosage in inhibiting tumor progression. This suggests that the dose rate of 1 mg/kg effective in the prostate cancer case could be lowered to almost 0.01 mg/kg if a parental administration route is selected. It is therefore assumed that a dose of about 0.01 to about 200 mg/kg of body weight per day is a reasonable range of median doses ($ED_{50}$) for treating cancer, at least partly by reducing or abolishing angiogenesis.

Several other patients added liquid cartilage extract to their diet (daily oral dose of about 75 mg of dry weight/7 mL of extract, equivalent to about 1–1.5 mg/kg of body weight/ day) in combination with more traditional therapies (surgery, chemotherapy, antihormonetherapy, etc.). Summaries of some medical cases are provided in the following table. The results suggest that combination therapy with liquid cartilage extract may increase survival rate and quality of life of patients suffering of solid tumors.

TABLE 12

| Type of cancer | Medical History |
|---|---|
| Urinary bladder | Urinary bladder 70-year old man; underwent ablative surgery of several lesions (2 cm and 1.5 cm) and added liquid cartilage extract to his diet; no residual carcinoma since 09/94. |
| Ovarian adenocarcinoma | 47-year old woman; lesions of 15 cm (right), 11 cm (left) and several 2 cm lesions; underwent surgery and chemotherapy in 1991; relapse treated by chemotherapy in 1992; second relapse treated by chemotherapy in 1993; addition of liquid cartilage extract to the diet in 1994; malignant neoplasm of reduced mass since. |
| Rhabdomyosarcoma | 63-year old man; infiltrating tumor of 11 cm in diameter (450 g); underwent surgery and chemotherapy; relapse treated by radiotherapy and addition of liquid cartilage extract to the diet; tumor showing necrosed tissue and stability since. |
| Pancreatic carcinoma with liver metastases | 45-year old woman; pancreatic lesion (9 cm) + liver metastases; chemotherapy and addition of liquid cartilage extract to the diet since; tumor regressed by 80% in 1994; tumor disappeared in 1995. |
| Mammary adenocarcinoma | 67-year old woman; surgery in 1978; relapse and lung metastases (1994); Megace and addition of liquid cartilage extract to the diet; since, partial regression of tumors in size (1.5 cm  1 cm) and number (12  6). |

Further, the liquid cartilage extract has a direct anti-tumor effect against melanoma cell lines. Since it also has anti-angiogenic and anti-metalloprotease activities, topical, parenteral or per os treatment of melanoma is within the scope of this invention.

Psoriasis

The following dermatological composition was made and tried to verify its efficacy in patients suffering of psoriasis:

EMULGADE CLB 29% (W/W)

20× crude permeate 69.5% (W/W)

GERMABEN 11 1% (W/W), and

Lavandula Angustifolia 0.5% (W/W)

EMULGADE CLB, a mixture of stearate esters, fatty alcohols and nonionic emulsifiers (purchased from Henkel Canada Ltd.) was heated at 65–70° C. under agitation. Heating was stopped while the mixture was kept under agitation. When the mixture reached a temperature of 45° C., the essential oil Lavandula Augustifolia and the preservative agents GERMABEN II (diazonidyl urea 30%, methylparaben 11%, propylparaben 3% and propylene glycol 56%; purchased from Sutton Laboratories, N.J., U.S.A.) were added. When the temperature of the mixture reached 30° C., the liquid cartilage extract was added. The 20× liquid extract was concentrated on a membrane having a nominal molecular weight cut-off value of 1 kDa. The composition so obtained was a smooth non-greasy cream; by varying the percentage of EMULGADE, other forms of various viscosity dermatological compositions can be obtained, in accordance with the manufacturer's directives (milk, lotion, ointment). Other vehicles or excipient might be used to obtain pastes, gels and any other form of transdermal preparation.

Figure 21A:
FIG. 21 illustrates the significant improvement of the condition of two patients suffering of psoriasis, one with hyperkeratosis 22a) and b), and the other one without hyperkeratosis 22c) and d), when treated with a topical composition containing an effective amount of concentrated liquid cartilage extract (lower photographs) compared with their initial condition (upper photographs).
Figure 21B:
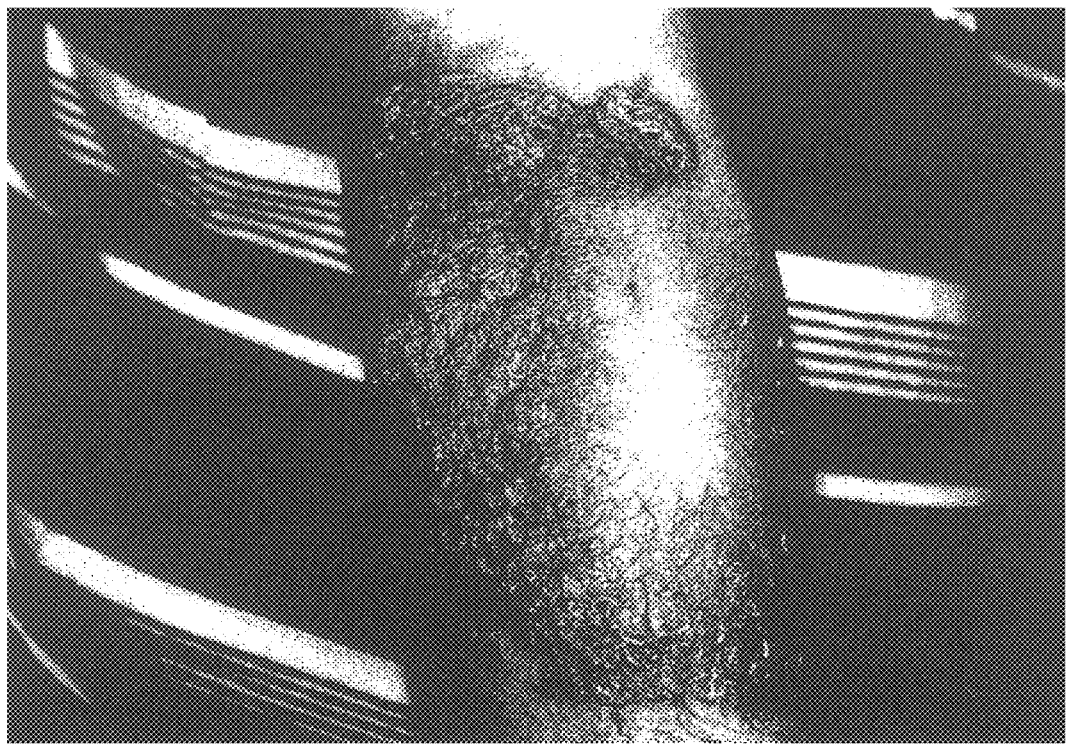
Figure 21C:
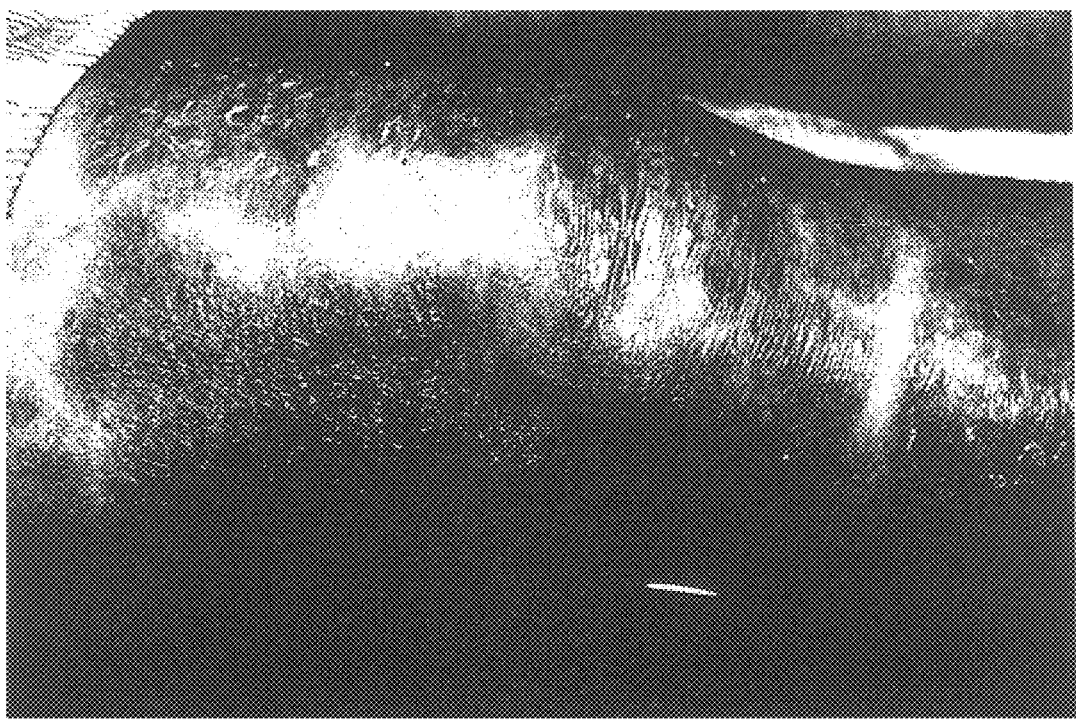
Figure 21D:
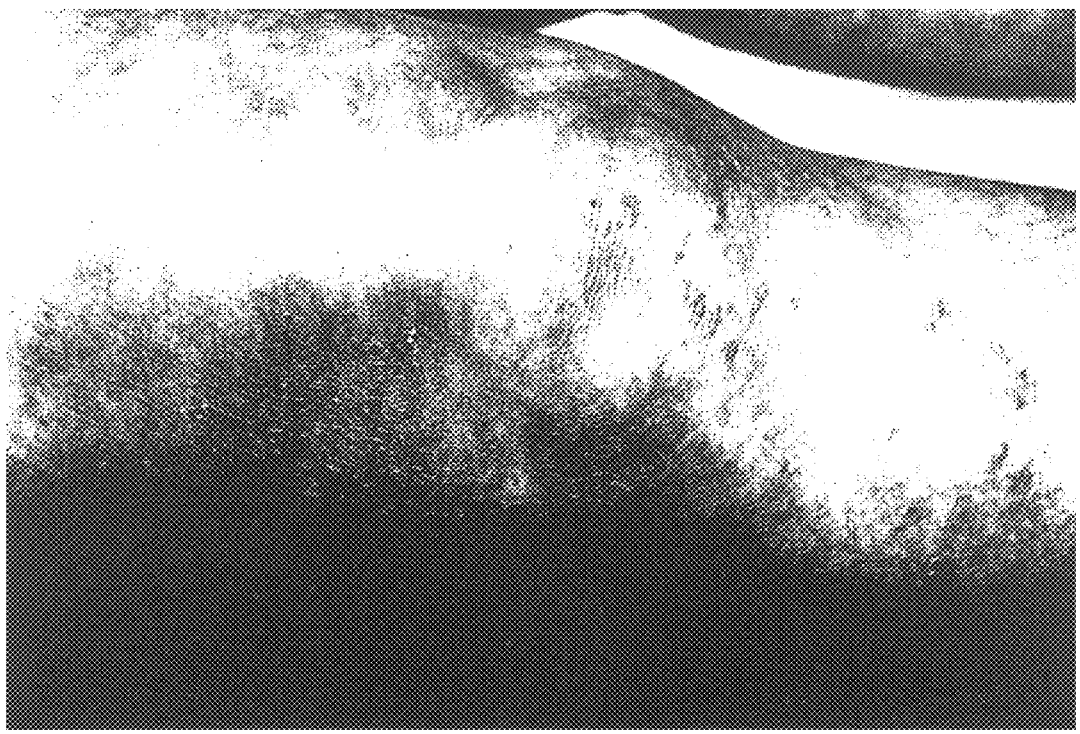

The above formulation was given twice daily during a period of twelve weeks to a panel of nine patients (topical application) suffering of psoriasis that had been responsive to the conventional therapies tried but became refractory to them after a while. For this study, patients were selected for the similar and symmetrical extent of psoriasis on both side members. These trials were conducted in a double-blind fashion, neither the dermatologist nor the patients knowing which affected side was treated with the composition containing the cartilage extract and which one was treated with a control composition. Remarkable improvement was observed in five patients whose psoriasis was not complicated by hyperkeratosis; for those having hyperkeratosis, the results were moderately good. Photographs of parts of two patients, bodies are shown in FIG. 21. In FIGS. 21a and b, it is demonstrated that a patient affected by psoriasis with hyperkeratosis has nevertheless shown a very significant reduction of the erythema, associated with no prurit, after only one month of treatment. The hyperkeratosis remained, however, important. Photographs of the second patient suffering of psoriasis not complicated with hyperkeratosis (FIGS. 21c and d) showed a much better improvement after a three month treatment. Since psoriasis appears to be a multifactorial disease, it is assumed that the response of the patients depends on the importance of the involvement of components like angiogenesis and inflammation in the establishment and in the perpetuation of this condition. The anti-angiogenic activity is indeed present in our extract, as shown in DMBA-treated rats (FIG. 5), endothelial cell proliferation (FIG. 7), and EVT (FIG. 10). The anti-inflammatory activity has also been verified (CHS model in mice). It is probable that better results might be obtained if this kind of formulation is complemented with other therapeutic agents addressing to other factors involved (keratolytic agents, additional anti-inflammatory agents, antihistaminics, immunosuppressors, etc.).

This complementation may take the form of amending the formulation to include an effective amount of a keratolytic agent. For example, it could also be achieved by the separate administration of such a complementary therapeutic agent, concurrently or in alternation with the application of the present topical formulation. Furthermore, the complementary medication does not need to be administered by the same route.

The above formulation has shown no systemic effect (the effect appears to be limited to the treated areas) and no secondary effect despite the high proportions in liquid cartilage extract.

Per os treatment of psoriatic patients also led to an improvement of 20 to 50% in 66% of patients treated with 30 to 240 mL/day shark cartilage extract. This confirms the oral availability of the anti-inflammatory and anti-angiogenic component of the present cartilage extract.

Rosacea

A comprehensive review of this skin disorder by J. K. Wilkin (Arch. Dermatol. (1994) vol. 130, 359–362) indicates that rosacea develops as a combination of one or more of the following cutaneous stigmata: flushing, erythema, telangiectesia, facial edema, papules, pustules, ocular lesions and rhinophyma, depending on the disorder stage development.

Erythema and telangiectesia are vascular disorders, and the other features, although not of a vascular nature, may derive from a vascular disturbance. The erythema is the first feature to be observed and represents an increased number of erythrocytes in a mildly inflamed vasculature. Furthermore a dermal cellulitis may appear as a result of an extravascular fluid accumulation consequent to irritant factors. The edema is the result of an increase extravasation along with a decrease fluid removal by lymphatic vessels. Decrease lymphatic activity appears to be consequent to lymphatic damage occurring during cellulitis. Rhinophyma may be explained by the observation that chronic cutaneous edema is frequently followed by connective tissue hypertrophy and fibroplasia and may also be due to factor XIII expression. It has been further emphasized that the elastin network that surrounds the lymphatic system in the skin serves two important functions. First, it is a tethering that permits the lymphatic endothelium to be sensitive to the volume of fluids in the vicinity of the lymphatic vessels, so that any increase of volume results in greater tension on the anchoring filaments. Second, the elastin network provides a low-resistance pathway through the intersticium along which micromolecules pass to the lymphatic vessels. Elastin degeneration due to actinic exposure is probably a common cause of lymphatic failure in rosacea.

During inflammation, neutrophils are recruited and exacerbate the rapid degradation of a variety of extracellular matrix macromolecules, especially elastin. Neutrophil elastase degrades type IV collagen in the extracellular matrix on which the integrity of the capillary walls depends. When lymphatic failure occurs, a sustained inflammation takes place. When lymphatic failure does not resolve the inflammation becomes self-sustained. The plasma proteins that accumulate in the sustained inflamed tissue appear to contribute to the fibroplasia, which underlies the development of rhinophyma.

Telangiectesia represents the latter phase of the vascular stage of rosacea. The mechanical integrity of the dermal connective tissue is reduced, allowing a passive dilation of the vasculature. The perivascular inflammatory cells thus infiltrate and contribute to rosacea. Dilatation of both dermal blood vessels and lymphatics are prominent in rosacea. Angiogenesis may contribute to the telangiectesia. Angiogenesis depends on the space left between in a tissue where endothelial cells can grow. Edema reduces the tissue compactness, permitting vascularization. Since lymphatic failure results in sustained inflammatory response, the edema thus created would be one the feature that favors angiogenesis.

As already mentioned above, it appears that rosacea is initiated by an inflammatory reaction which does not resorb with time.

Since shark cartilage comprises a plurality of biological activities such as anti-metalloprotease, anti-angiogenic, anti-tumor, anti-inflammatory and also probably (since bovine cartilage contains it) anti-elastase activities, and since it inhibits VEGF activity (it at least inhibits the VEGF-induced extravasation), it is contemplated that the shark cartilage extract will have an effect on all skin diseases involving one or more etiologies related to these biological activities. The shark cartilage extract of this invention comprises a plurality of active ingredients and as such will be effective in treating mono- as well as in pluri-factorial diseases or disorders. The treatment of rosacea is a typical example of such a pluri-factorial disorder wherein inflammation, metalloprotease activity and angiogenesis occur.

For example, a small panel of people suffering from rosacea was treated with a shark cartilage extract topically formulated in a commercial Glaxal Base or with a non-commercial base. The liquid cartilage extract was at a concentration of 5%–10% (20× extract). The formulation was applied twice daily for about four to twelve weeks on affected areas of their faces. A noticeable reduction of redness and of facial blood flow was observed. Measurements with a scanning laser Doppler capillary perfusion monitor showed a 34%, 31% and 32% reduction in blood flow after 1, 2 and 3 months of treatment, respectively. Visual grading of erythema showed improvements of 24%, 27% and 44%, respectively.

These results confirm that the cartilage extract inhibits reddening, e.g., the erythema, of the skin typically associated with rosacea. The erythema forms as a consequence of the migration of erythiocytes into the tissue. It is likely that such a migration was inhibited by the cartilage extract by preventing inflammation and/or metalloprotease activity.

Arthritis

Patients suffering of arthritis have tried on a voluntary basis one to two units of 7 mL total liquid extract per day for several months. These patients saw their condition improved gradually by recovery of joint function, diminution of pain and inflammation (up to about 60%). Since arthritis has angiogenic and inflammatory components, the above effect can be attributed to anti-angiogenic and anti-inflammatory activities of the cartilage extract.

A pilot clinical study was then conducted by a group of specialists in rheumatology. Seven voluntary and enlightened subjects aged between 39 and 60 years of age and suffering from rheumatoid arthritis enrolled in the study. Diagnosis was established based on the classification criteria in the revised edition of the American Rheumatism Association's (Arnett, F. C. et al., 1988, *Arthritis & Rheumatism*, vol. 31, 315–325).

The treatment lasted 30 days and consisted of in ingesting a daily dose of 21 mL of liquid shark cartilage extract (12 mg/mL of dry weight). The efficacy of the treatment was determined with an articular index for the assessment of joint tenderness (Ritchie, D. M. et al., 1968, *Quarterly J. Med, New Series XXXVII*, vol. 147, 393–406). The index is based on the summation of a number of quantitative evaluations of the pain experienced by the patient when joints are subjected to firm pressure exerted over the articular margin or in some instances upon moving the joint. The results show that four patients out of seven have improved when treated with the liquid cartilage extract (Table 13 below), suggesting that the product may be useful in the treatment of rheumatoid arthritis or other conditions complicated by chronic inflammation.

TABLE 13

| | | Ritchie's INDEX | | |
| Patient (no) | Age (years) | Day 0 | Day 30 | Improvement |
| --- | --- | --- | --- | --- |
| 1 | 60 | 30 | 22 | Yes |
| 2 | 43 | 8 | 8 | No |
| 3 | 52 | 12 | 12 | No |
| 4 | 41 | 15 | 19 | No |
| 5 | 46 | 5 | 3 | Yes |
| 6 | 39 | 6 | 2 | Yes |
| 7 | 55 | 14 | 7 | Yes |

Spider Veins

A total of sixteen panelists were recruited for the study. The panelists had visible but not excessive telengectasia on the face. The panel was divided in two groups of eight each. Group A was provided with a cholesterol liposomal base containing 5% liquid cartilage extract while the second group (B) was provided with the cholesterol liposomal base alone. The products were used on the full face, twice a day for three months. A fiber optic surface microscope was used to obtain images of a minimal of four sites of the face showing spider veins. The images were analyzed for grey values via the Zeiss Ibas Image Analyzer. Integrated Optical Density (IOD) was calculated for each site for each panelist. The four sites on each panelist were averaged for each time point.

Figure 22:
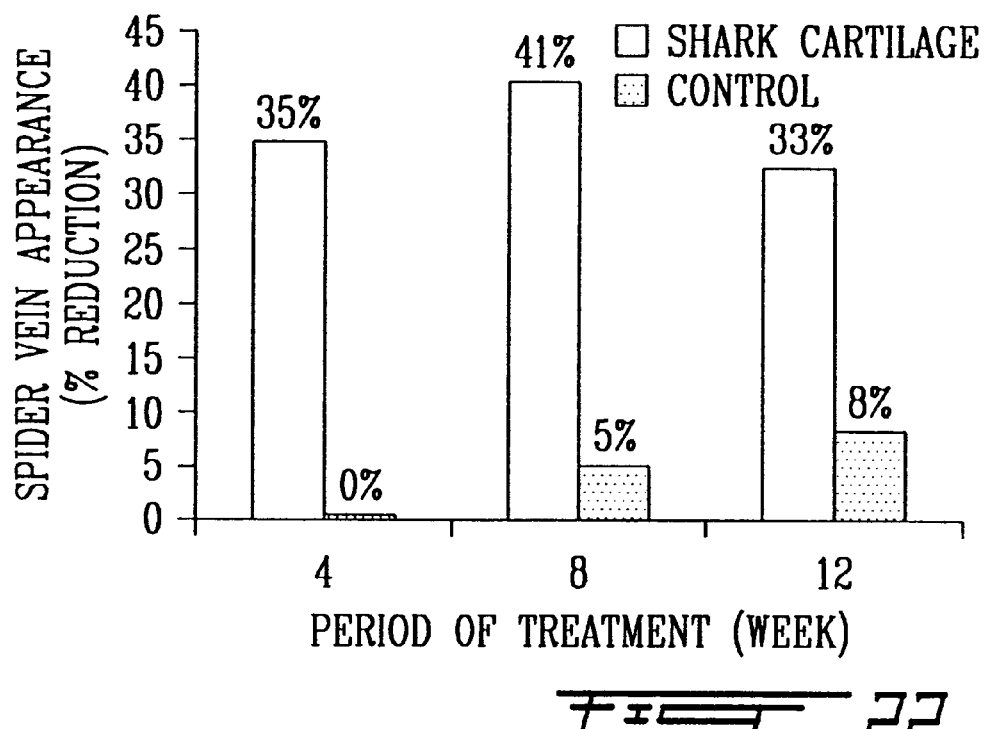
FIG. 22 shows the improvement of the appearance of spider veins in the visage of humans treated with liquid cartilage extract.

The results show there was a 35% decrease in the IOD after four weeks and this effect maintained for the course of the study (FIG. 22). The empty cholesterol liposomal base exhibited a background improvement of 5% and 8% after eight and twelve week use, respectively.

Peri-Orbital Dark Circles

Skin coloration is not entirely due to the presence or absence of melanin, but also blood supply and plasma contents. When the blood flow is sluggish and greater amounts of oxygen are removed for metabolism, the skin appears bluish in color. These color differences are exaggerated in the eye area because of the thinness of the skin (Oresajo et al. (1987) Cosmetics Toiletries 102: 29–34). Vascular changes in the septa that are present under the eye can also exacerbate the appearance of dark circles. Dark circles around the eyes also appear due to fat deposition, edema under the eyelids and leakage of blood vessels around the eye area. These symptoms appear to be inflammation and angiogenesis related. Clinical study was designed to evaluate the effect of shark cartilage liquid extract on controlling angiogenesis around the eye area thereby reducing the appearance of peri-orbital dark circles.

A total of eighteen female volunteers between the age of 18–65 participated in the study. The panelists exhibited distinct dark circles around the eyes. All panelists were normal in health with no evidence of acute or chronic diseases including dermatological or ophthalmologic problems.

Subjects exhibiting current sunburn, rashes, scratches, burn marks, etc., which might interfere with evaluation of test results were excluded from the study. Pregnant or lactating females were also excluded. The test site was devoid of warts, moles, sunburn, suntan, scars, and active dermal lesions observed upon observation.

The panel was divided in two groups, ten in group A and eight in group B, each corresponding to the vehicle containing 5% liquid cartilage extract or the vehicle alone, respectively. The panelists were provided with enough product to be applied around the eye area at least twice a day for twelve weeks. Measurements were obtained at baseline, and after four, eight, and twelve weeks. At each visit photographs were obtained and analyzed via Image Analysis.

Figure 23:
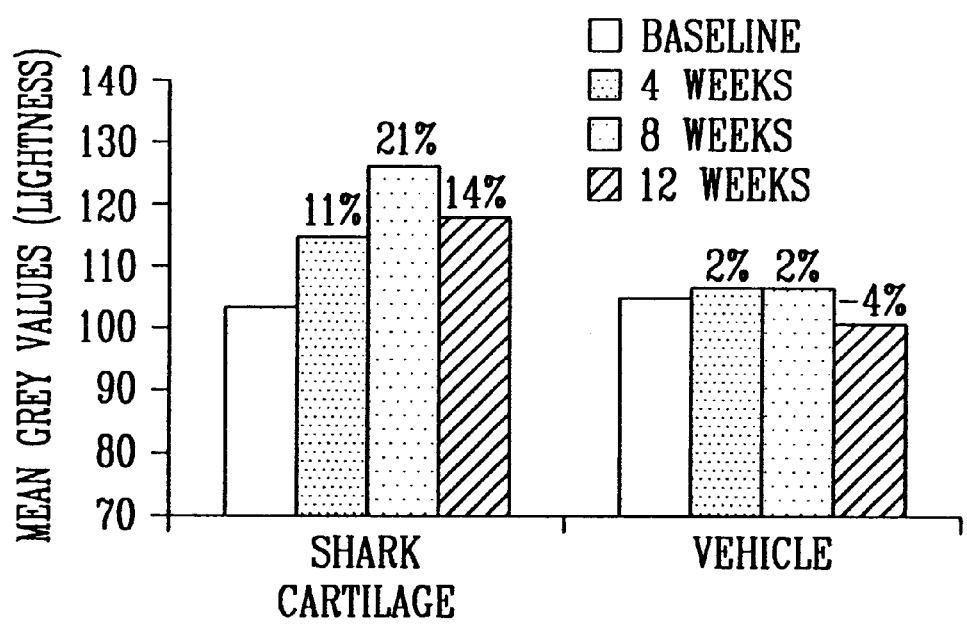
FIG. 23 shows the improvement of the appearance of dark circles around the eyes of humans treated with liquid cartilage extract.

Photographs were analyzed for the gray values that depict darkness/lightness of skin. It is clear that the group treated with liquid cartilage extract exhibited a good increase in gray values (which depicts lightening of dark coloration). After four, eight, and twelve weeks there was 11%, 21%, and 14% lightening of the skin under the eye area of the group treated with the liquid cartilage extract. The group treated with the vehicle alone did not show any change (FIG. 23).

Varicose Veins

A total of twenty panelists completed the study. The panelists had visible but not excessive telangiectasia on the legs. The panel was divided in two groups, Group A (n=9) was provided a liquid cartilage extract containing cream while Group B (n=11) was provided a vehicle cream alone to be used on the full legs, twice a day for three months. A fiber optic microscope was used to obtain images of 2–4 sites of the legs showing varicose veins. The images were analyzed for grey values via the Zeiss Ibas analyzer. Integrated Optical Density (IOD) was calculated for each site for each panelist. All the sites on each panelist were averaged for each time point.

Figure 24:
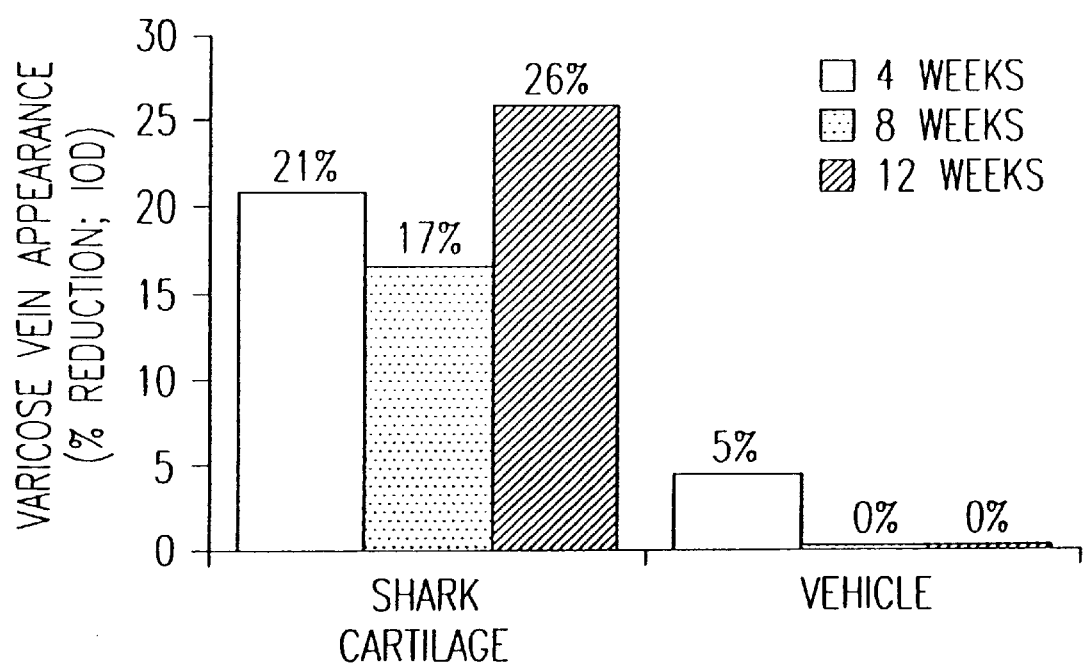
FIG. 24 shows the improvement of the appearance of varicose veins on the legs of humans treated with liquid cartilage extract.

Results are illustrated on FIG. 24. There was 21%, 17% and 26% decrease in the IOD after four, eight and twelve weeks of use, respectively. The control vehicle exhibited a background improvement of 5%, 0% and 0% after four, eight and twelve weeks of use, respectively.

Other Potential Clinical and Veterinary Applications

Ophthalmology: A decrease in vision or blindness can be caused by a number of conditions characterized by abnormal blood vessel growth or neovascularization. These include corneal neovascularization (caused by chemical or physical irritation), corneal infection, corneal graft rejection, neovascular glaucoma, macular degeneration, herpes virus keratitis, and diabetic retinopathy. The liquid cartilage extract could act upon these clinical conditions by inhibiting the formation of new blood vessels, and by reducing telangiectasis and inflammation.

Wound Repair: Wound repair involves a complex interaction between cells, biochemical mediators, extracellular matrix molecules, and the cellular microenvironment. After full-thickness wounding, granulation tissue (fibroblasts, capillaries, and inflammatory cells) first grows from the wound edge in a characteristic sequence. Fibroblasts begin to migrate into the wound space from connective tissue at the wound edge within 24 hours. As they move, fibroblasts produce matrix molecules (collagen and glycosaminoglycans), which form an extracellular matrix. The first capillary buds can be seen in the perfused microcirculation at the wound edge as early as 18 hours after wounding. These buds grow into the wound space and provide the new capillary network for the wound connective tissue. Fibroblast proliferation and migration and capillary growth continue as a unit until the wound space is completely filled with new tissue. Some wound repair conditions that are complicated by overexpression of granulation factors, such as hypertrophic scarring and the healing of the skin of badly burned person, could benefit of the administration of liquid cartilage extract (orally or topically) since decreasing the angiogenic process would slow down the process of wound healing and repress overexpression of granulation factors.

Papulosquamous Skin Disease: The beneficial effect of liquid cartilage extract on psoriasitic lesions suggests that other diseases having common characteristics could also profit of local or systemic administration of the liquid extract. The papulosquamous skin diseases are characterized by red to violaceous papules and plaques that result from thickening of the epidermis and/or underlying dermal inflammation and include psoriasis, Reiter's syndrome, pityriasis rosea, lichen planus, pityriasis rubra pilaris, secondary syphilis, mycosis fungoides, and ichthyosiform eruptions.

Alopecia: The ligature of small lateral arteries driving blood flow to the scalp has been successful to prevent hair loss caused by androgen overexposure. Local application of liquid cartilage extract on some region of the scalp could prevent hair loss by decreasing the vascular network and consequently the exposure to hormones.

Veterinary Applications: Solid and/or liquid cartilage extracts may be administered to animals for the same therapeutic and cosmetic applications that have been described for humans.

Most, if not all, of the above-mentioned diseases, which have been classified as representative of angiogenic-related diseases, appear to have an inflammatory etiological component as well as a matrix metalloprotease etiological component. There is an increasing body of literature that shows that inflammation is one the early events that are involved in signaling a danger to the body. Inflammation initiates other events like blood cell recruitment to the endangered site, which cells are then activated and secrete cytokines. Matrix metalloproteases are secreted in order to break the extracellular matrix down and to facilitate other cell recruitment. Inflammation is usually stopped when the danger has disappeared and the tissue has returned to normal function. However, in some cases, inflammation is self-sustained and leads to chronic disease which tends to aggravate with time. A majority of diseases or disorders is plurifactorial so that it is almost impossible to draw a line between angiogenesis-, inflammation-, metalloprotease-, and cell proliferation-related diseases. In many documented cases, namely rosacea, angiogenesis appears at a late stage, wherein the disorder aggravates as a consequence of a lack of treatment that would have controlled inflammation at an earlier stage.

Non-Anti-Angiogenic Effect

Acne

Even though acne is not generally considered a disease or disorder having an angiogenic component, it was nevertheless tempting to test the liquid cartilage extract in patients so affected on the basis that the liquid extract is also anti-inflammatory. For experimenting the cartilage extract in patients affected by acne, the following gel formulation was made:

CARBOPOL 1.2%
Purified water 77.2%
NaOH 0.3%
PHENOXETOL 0.3%
TWEEN 80 0.3%
2× Liquid cartilage extract 20.0%
40× Aloe extract 0.5%

Figure 25A:
FIG. 25 illustrates the significant improvement of the condition of a patient suffering of acne when treated with a topical composition containing an effective amount of liquid cartilage extract (lower photograph) compared with her initial condition (upper photograph).
Figure 25B:
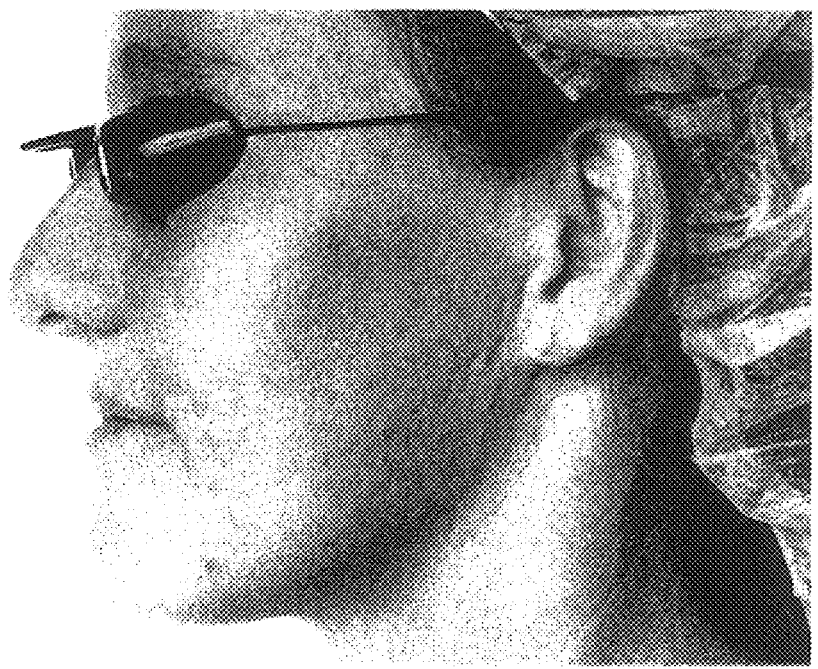

The liquid cartilage extract contains 9–12 mg/mL of dry weight and was concentrated on a membrane of NMWCO of 1 kDa. This formulation shows a remarkable improvement of the aspect of the skin of patients affected by more or less severe forms of acne (inflammatory acne and cystic acne). FIG. 25 shows the significant improvement of the condition of a patient suffering of acnea when treated with the topical liquid extract containing vehicle during twelve weeks.

These results may be due to an anti-angiogenic effect (thus revealing an angiogenic component in acne), or they may be due to the presence of active ingredients in the liquid extract that have an effect other than anti-angiogenic (an anti-inflammatory effect, for example). All the results obtained in the above clinical trial show the great potential of the cartilage liquid extract in the treatment of angiogenesis-dependent and/or inflammatory diseases. The amount of cartilage extract as well as the formulation thereof may be varied at will to fulfil specific needs.

One can note that, on a protein content basis, the topical and all other compositions may contain a wide range of doses of the cartilage extract. Among the three specific categories of cases tested, very different dosages and/or formulations have been used.

Skin Irritancy

Since angiogenesis is often associated to inflammation in numerous diseases, it would be desirable to assign each activity separately in the cartilage extract. In this regard, a skin irritation model wherein no angiogenesis is suspected to occur has been chosen to test the extract for its anti-inflammatory and soothing activity. Nine volunteers with a history of skin sensitivity to balsam of Peru were chosen for the study. The test compounds were as follows:

1. IX Shark cartilage 50% in D-MEM media
2. IX Shark cartilage 20% in D-MEM media
3. IX Shark cartilage 10% in D-MEM media
4. Cola nitida (Indena) 10% Hydro-alcohol 1:1.

Figure 26:
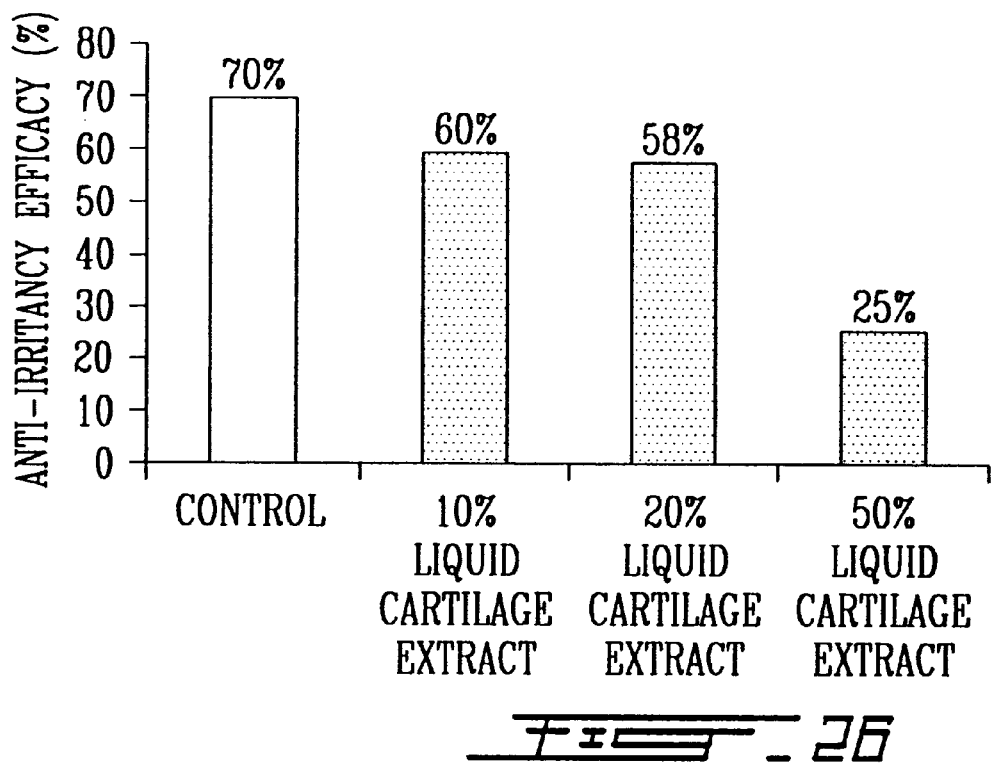
FIG. 26 shows the anti-inflammatory potential of the liquid cartilage extract on human skin.

The four test compounds were applied on the ventral forearms of the panelists. The material was allowed to absorb for twenty minutes and then balsam of Peru, an irritant, was applied on the test sites. Skin irritation was measured in terms of increase in skin redness. The degree of redness was measured with a Minolta Chromameter and compared with the positive and negative controls. The positive control was the color of skin treated with balsam of Peru alone and the negative control was a skin site treated with cola solution and challenged like the test products. Statistical significance was calculated via two tailed probability T-test. FIG. 26 shows that cola at 10% was 70% active. Shark cartilage was 58% and 60% as anti-irritant at 20% and 10% concentrations, respectively. There was no dose-response effect. These results suggest that the cartilage extract contains anti-inflammatory and soothing activity which is remote from an anti-angiogenic effect.

Many types of skin irritants are known and include, for example, chemicals, physical abrasion, U.V. radiation, allergens, or infectious agents (fungi, viruses and bacteria). The anti-inflammatory activity of the present cartilage extract counteracts the action of these various irritants and is therefore useful in treating disorders or diseases related to them.

Cancer

A 53 year old female patient was diagnosed as having a large cell non-Hodgkin's lymphoma of the B type. CAT scan analysis revealed adenopathies around the carotid and the jugular vein (2.5 cm in diameter) and a voluminous adenopathy over the right renal hilus. The patient refused chemotherapy and added the liquid cartilage extract to her diet (October 1993)(daily oral dose of about 75 mg of dry weight/7 mL of extract, equivalent to about 1-1.5 mg/kg of body weight/day). Three months later (January 1994) CAT scan analysis revealed adenopathies in the neck completely resorbed. By November 1994 the abdominal adenopathy has decreased in volume by 75%.

This result suggests that some non solid cancers may also respond to the anti-tumor activity of the liquid cartilage extract.

Barrier Protection of the Skin

A panel of six healthy volunteers participated in the study. The panelists received a cream containing the liquid cartilage extract to be applied on the right forearm and the vehicle only to be applied on the left forearm, twice a day for four weeks.

The panelists were female, ages 21–45, with no evidence of acute or chronic disease including dermatological or ophthalmologic problems. Subjects exhibiting current sunburn, rashes, burn marks, etc., which might interfere with evaluation of test results, were excluded from the study. The test site was devoid of warts, nevi, moles, sunburn, suntan, scars and active dermal lesions observed upon examination. On the day of the test, the panelists were instructed to refrain from using any lotions, creams or other products on the face. During the course of measurements, the panelists were equilibrated for at least 30 minutes prior to testing in a controlled environment of 20–22° C. temperature and 40% relative humidity.

The test site was the right and left volar forearms. A small area (3.5 cm×7 cm) was marked on each arm and basal transepidermal water loss (TEWL) measurements were obtained from three sites within this area (Pinnagoda et al. (1990) Contact Dermatitis 22: 164–178; Grove (1994) in *The effects of aging in oral mucosa and skin,* Ed. Squier & Hill, CRC Press, pp 124–125).

A sticky (Tuck) tape was used to cover the test area and, after a firm stroke in both directions, the tape was peeled off (Elias (1993) J. Invest. Dermatol. 80: 044s–049s). A total of 5 strippings were obtained. TEWL was recorded again. Strippings followed by TEWL measurements were continued in groups of 5. The strippings were stopped when the TEWL approached 18 $G/M^2/Hr$. TEWL was measured again at the end of the last stripping sequence. The number of strippings required to damage the skin barrier was calculated by noting the number of maximum strippings for each arm, at each time point that exhibited a TEWL of 18 $G/M^2/Hr$ or more. The results were analyzed for statistical significance between treatment at various time points versus baseline using the one tailed rank coefficient Z test.

Figure 27:
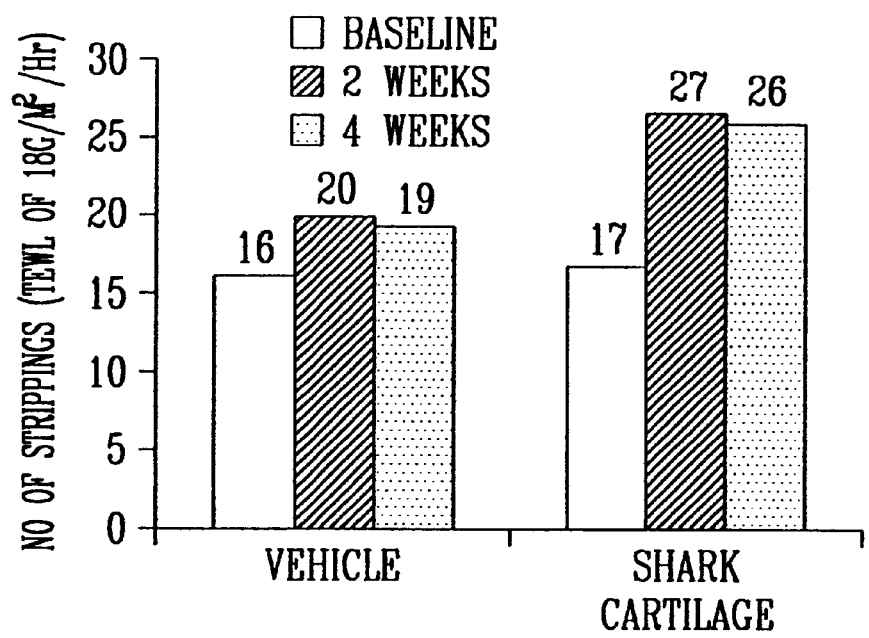
FIG. 27 shows the improvement of the barrier function of the skin of humans treated with liquid cartilage extract.

The vehicle treated arm did not appear to exhibit much improvement. Only 26% and 21% more stripping was required to damage skin after 2 week and 4 week treatments, respectively. There was a significant improvement ($p<0.05$) in barrier condition of each of the panelists after treatment with liquid cartilage extract product for 2 and 4 weeks when 60% and 55% more strippings were required to disrupt skin barrier (FIG. 27).

Therefore, the liquid cartilage extract has proven to be useful in strengthening skin barrier against physical damage. Without being bound to any theory, it is believed that this effect is due to the anti-inflammatory and anti-metalloprotease activities of the cartilage extract.

Eczema

The liquid cartilage extract was tested in beauty salon on the basis of its ability to decrease the inflammatory lesions caused by eczema. The beautician applying the liquid extract-containing cream suffers since many years of chronic eczema in her hands. Interestingly, the uses of the cartilage-containing cream decreased significantly the expression of eczema in her hands. She is now using successfully the cartilage-containing cream to prevent the expression of eczema.

Warts

A 36 years old female with a history of plantar warts was treated by a dermatologist for almost three years to control wart progression and associated pain. Among the treatments there was liquid Nitrogen, Salicylic acid (40%), Anaerobia, Nitric acid, and sulfuric acid. These treatment were generally every week for a duration of three months and the results were almost nil. In March 1996 she applied daily (5 minutes) the shark cartilage liquid extract directly on the warts; two weeks later a pink zone of new epidermis formed around the warts; the following week warts were gone. Therefore, this result suggests that the liquid cartilage extract may help in the treatment of warts, particularly by its anti-metalloprotease activity. Warts have a decreased chance of remaining implanted in the skin.

Other Potential Clinical and Veterinary Applications

Graft Rejection: Inflammation is one of the major factor involved in the early mortality of transplanted cells. Therefore, tissue graft could benefit from the anti-inflammatory components present in our shark cartilage liquid extract. Furthermore, an anti-metalloprotease activity should be responsible for the inhibition of recruitment of inflammatory and immune cells to the transplantation site.

Multiple Sclerosis: The cause of multiple sclerosis are unknown. The tissue response has features of an immunopathologic process, with perivenular mononuclear cell infiltration and absence of any overt histopathologic evidence of an infection. Matrix metalloproteinases are important factors involved in inflammatory response. Since liquid cartilage extract is a powerful inhibitor of matrix metalloproteinases it may be useful in the treatment of multiple sclerosis.

Fibrosis: Current concepts suggest that fibrosis resembles normal wound healing, but fail to terminate, leading to the replacement of normal tissue with scar. Most fibrotic reactions appear secondary to trauma, infection, inflammation or, for unknown reasons, may have a genetic component. Typically TGF-$\beta$ is overproduced and induces the proliferation of fibroblastic cells and the overproduction of collagen. Since an excessive deposition of collagen is the hallmark of fibrosis, we suggest that liquid cartilage extract which can delay the formation of granulation tissue could have long term benefits in suppressing fibrotic reactions.

Inflammatory Bowel Disease: The etiology of inflammatory bowel disease is unknown, but abnormal intestinal immunity is involved in the pathogenesis of Crohn's disease and ulcerative colitis. Mucosal mononuclear cells display altered antibody production, proliferation, cytotoxicity and cytokine synthesis (FGF, PDGF, EGF, TNF). Liquid cartilage extract has shown anti-inflammatory activity and then oral administration may prove to be helpful in the therapeutical treatment of inflammatory bowel disease.

Heart Diseases: Endothelial dysfunction of coronary resistance vessels can account for abnormalities of the coronary microvasculature and possibly myocardial ischemia and chest pain. At a cellular level, endothelial dysfunction is associated with reduced expression of nitric oxide (NO), an endothelium-derived relaxing factor. NO synthesis allows the vascular system to maintain a state of vasodilatation thereby regulating arterial pressure. A deficit in endogenous synthesis of NO contributes to such conditions as arterial hypertension, pulmonary hypertension and heart disease. We have preliminary results from cultured endothelial cells that the liquid cartilage extract increases NO production. The liquid extract might therefore, through NO, prove to be helpful in some heart disease conditions as well as in pediatric patients with congenital heart disease complicated by pulmonary artery hypertension.

Moreover, liquid cartilage extract may help to decrease inflammation-associated complications in atherosclerosis via its anti-inflammatory and anti-MMP components.

Scleroderma: Scleroderma (Hard skin) is an uncommon disease marked by increases in fibrotic connective tissue of skin and often of visceral organs as well. It often appears as a hyperkeratinization of localized skin patches. Hyperkeratinization is a cellular process in which keratinocytes of the skin fully differentiate and accumulate rigid keratin fibers. This skin condition might lead to limited joint mobility if skin in a periarticular area is affected. When added to an experimental system in which keratinocyte differentiation is encouraged, the liquid cartilage extract partially prevents the process of differentiation, or keratinization. Therefore, the liquid extract might be beneficial for such skin conditions by preventing the overaccumulation of fully differentiated keratinocytes.

Veterinary Applications: Solid and/or liquid cartilage extracts may be administered to animals for the same therapeutical and cosmetic applications that have been described for humans.

Cosmetic Applications and Compositions

The above tests and trials have shown that the cartilage extract of this invention may find numerous medical applications. Among the diverse activities recovered in this extract, anti-angiogenic, anti-collagenolytic, anti-inflammatory and the inhibitory effect on PKC-induced differentiation are particularly desirable in cosmetic applications. Since the cartilage extract of the present invention has shown an antagonist effect of PKC-mediated cellular events, and since such antagonist effect is suggested in the art as one improving the skin barrier function, a method for improving the barrier function in mammalian skin which comprises the step of applying to the skin a composition which comprises the cartilage extract and a pharmaceutically acceptable carrier, and such a composition are within the scope of this invention. Other or similar compositions can also be conceived to be used in a method for soothing skin or for reducing inflammation in mammalian skin. Inflammation can be caused by various agents such as chemical irritant, physical abrasion and exposure to ultra-violet radiation. Compositions and methods for inhibiting collagenase in skin are also contemplated. Collagenase and inflammation are linked to premature aging (degradation of collagen), and therefore the antagonist activities recovered in the cartilage extract could also be put to contribution in compositions and methods for retarding premature aging, and for regulating wrinkles or atrophy in mammalian skin. As causes of wrinkles or atrophy are listed, by way of examples, age, exposure to ultraviolet radiation or to environmental pollutant. Topical compositions may comprise an effective amount of shark cartilage, to be determined for each specific application. In general, these compositions may contain from about 0.1 to about 75 weight percent of a liquid cartilage extract and from about 25 to 99.9 weight percent of a pharmaceutically acceptable vehicle. These compositions may contain an anti-oxidant, such as an agent which prevents the formation of lipid peroxides in skin. Examples of such an anti-oxidant are tocopherol, tocopherol derivatives, ascorbic acid, ascorbic acid derivatives and BHT. The compositions can be complemented with anti-inflammatory agents like a phospholipase A2 inhibitor or the botanically-derived anti-irritants cola and green tea extract. Topical compositions may take diverse forms such as solutions, suspensions, lotions, tinctures, gels, creams, sprays, emulsions, sticks, ointments or liposomes (at least a portion of the liquid cartilage extract being present in liposomes). Other cosmetic applications include dark circle around the eyes and skin barrier function.

The process of the present invention has been demonstrated as one that provides for the production of cartilage extracts of clinical value. The shark cartilage extracts produced by this novel process comprises a multiplicity of activities that are recovered in good yields. The cartilage extracts, particularly the liquid extract and fractions thereof have a great potential since they are non-toxic to normal cells while they are effective in a large variety of diseases or conditions.

For all predicted applications (from ophthalmic drops to dermatological and cancer drug formulations), it is presumed that a minimal final protein concentration of the total liquid extract could be very low (from about 0.01 mg/ml). This lower range of doses depends on the accessibility and on the permeation of the active ingredients to the site of action as well as on the efficient capture of these ingredients and the sensitivity or response of the tissue to angiogenic inhibitors. The highest limit of the final protein concentration in formulations for some applications is not currently known. The highest final concentrations tried were a topical administration of about 9 mg/mL of proteins in the formulation for the psoriasis cases and an oral administration of about 12 mg/mL in the dose unit of 7 mL administered daily in the cancer cases and 21 mL in the arthritis trial.

The shark cartilage liquid extract may lose some of its activities when lyophilized. However, the addition of stabilizers or protective agents as known in the art prior to lyophilization may preserve sensitive activities and make possible the administration of higher doses of the cartilage extract in the dry state.

Materials Used in Preparation/Use of Invention:

Coolers

Surgical instruments

Meat chopper

Plastic bags

Industrial blender (Waring 3-speed blender bought from Fisher Scientific)

A system of purification of water (inverse osmosis and 0.1 Êm filtration; Continental Water System, model PRE 2202, serial number 91089, Modulab Bioscience RQ/Polishing System bought from Fisher Scientific, Montreal, Quebec). This system provides an apyrogenic water of high quality.

A precision balance Mettler, series AE bought from Fisher Scientific

Centrifuge Sorvall RC-285 bought from DuPont Canada

Centrifuge CEPA

Nylon pocket of a porosity of 1 $\mu$M

An autoclave (automatic vapor sterilizer Sanyo, model MAC 350P)

Nalgene 500 mL containers sterilized at 132° C. for 10 minutes and dried for 35 minutes Conical filters of 24 $\mu$m porosity Whatman Reeve Angel Ultrafiltration column (Molecular weight cut-off: 500 kDa, 1 kDa, and 0.1 kDa when applicable; Surface: 25 square feet; Flow: 130 L/minute; Inlet pressure: 30 psi; Outlet pressure: 5 psi; bought from Koch Membrane Systems Inc., Wilmington, Mass., USA)

Sanitary centrifuge pump (Monarch industries, model ACE-S 100, type A) for providing a 130 L/minute flow sterile hot (laminar flow hot NuAire bought from Ingram & Bell)

Millipack-60 0.22 $\mu$m sterile filters

Sterile clear or amber glass bottles

Concentrator DC-10 Amicon

Rotofor BioRad 170-2950

Amicon filters SIOY10, SIOY30 and SIOY100 of cut-off values of 10, 30 and 100 kDa, respectively FPLC Pharmacia 216007 (computer Pharmacia 216014)

Hilstand S-300 26 mm/60 cm (Pharmacia)

Superose S-12 10 mm/30 cm (Pharmacia)

Lyophilizer Labconco 10273 A

This invention has been described hereinabove, and it should be appreciated that it would be well within the ability and the knowledge of the person skilled in the art, without departing from the teachings of this disclosure, to bring modifications by replacing some elements of this invention as practiced by their equivalents, which would achieve the same goal thereof. These obvious variations are deemed covered by this application.

What is claimed is:

1. A method for treating a skin disease or disorder having an etiology related to angiogenesis, the method comprising the step of applying to the skin of a patient in need of such treatment a topical composition comprising a therapeutically effective amount of a shark cartilage extract comprising one or more biologically active components, a majority of which have a molecular weight less than about 500 kDa.

2. The method of claim 1, wherein the method is a method of reducing telangiectasia.

3. The method of claim 2, wherein the telangiectasia is at least one of varicose veins and of spider veins.

4. The method of claim 2, wherein the method is a method of reducing periorbital dark circles.

5. The method of claim 2, wherein the method is a method of reducing the redness caused by rosacea.

6. The method of claim 1 wherein the shark cartilage extract has been prepared by a process comprising the step of:

first fractionating a crude cartilage extract comprising water soluble biologically active components obtained from shark cartilage material such that a major portion of the biologically active components having a molecular weight greater than about 500 kDa is separated from a major portion of biologically active components having a molecular weight of less than about 500 kDa to form the shark cartilage extract.

7. The method of claim 6 further comprising the earlier step of:

treating a particle size-reduced cartilage solid with an aqueous solution for a period of time and at a temperature sufficient to extract said water soluble biologically active components from the particle size-reduced cartilage solid.

8. The method of claim 7 further comprising the earlier step of:

reducing the particle size-reduced cartilage solid.

9. The method of claim 6 further comprising the later step of:

removing a major portion of water present in said first fractionated cartilage extract.

10. The method of claim 6, further comprising the step of:

second fractionating said first fractionated cartilage extract to separate and remove a major portion of water soluble biologically active components having a molecular weight less than about 0.1 kDa to form a second fractionated cartilage extract comprising water soluble biologically active components having a molecular weight between about 0.1 kDa to about 500 kDa.

11. The method of claim 6 further comprising the step of:

second fractionating said first fractionated cartilage extract to separate and remove a major portion of water soluble biologically active components having a molecular weight less than about 1 kDa and to form a second fractionated cartilage extract comprising water soluble biologically active components having a molecular weight between about 1 kDa to about 500 kDa.

12. A method of treating warts in mammalian skin, said method comprising the step of applying to the skin of a patient in need of such treatment a topical composition comprising a therapeutically effective amount of a shark cartilage extract comprising one or more biologically active components, a majority of which have a molecular weight less than about 500 kDa.

13. The method of claim 12, wherein the shark cartilage extract has been prepared by a process comprising the step of:

first fractionating a crude cartilage extract comprising water soluble biologically active components obtained from shark cartilage material such that a major portion of the biologically active components having a molecular weight greater than about 500 kDa is separated from a major portion of biologically active components having a molecular weight of less than about 500 kDa to form the shark cartilage extract.

14. A method of treating a papulosquamous skin disease or disorder, said method comprising the step of applying to the skin of a patient in need of such treatment a topical composition comprising a therapeutically effective amount of a shark cartilage extract comprising one or more biologically active components, a majority of which have a molecular weight less than about 500 kDa.

15. The method according to claim 14, wherein the disease or disorder is selected from the group consisting of Reiter's Syndrome, pityriasis rosea, lichen planus, pityriasis rubra pilaris, secondary syphilis, mycosis fungoides, and ichthyosiform eruptions.

16. The method of claim 14, wherein the shark cartilage extract has been prepared by a process comprising the step of:

first fractionating a crude cartilage extract comprising water soluble biologically active components obtained from shark cartilage material such that a major portion of the biologically active components having a molecular weight greater than about 500 kDa is separated from a major portion of biologically active components having a molecular weight of less than about 500 kDa to form the shark cartilage extract.

17. A method of promoting wound repair in a mammal, the method comprising the step of applying to the skin of a patient in need of such treatment a topical composition comprising a therapeutically effective amount of a shark cartilage extract comprising one or more biologically active components, a majority of which have a molecular weight less than about 500 kDa.

18. The method of claim 17, wherein the shark cartilage extract has been prepared by a process comprising the step of:

first fractionating a crude cartilage extract comprising water soluble biologically active components obtained from shark cartilage material such that a major portion of the biologically active components having a molecular weight greater than about 500 kDa is separated from a major portion of biologically active components having a molecular weight of less than about 500 kDa to form the shark cartilage extract.

19. A method of treating an inflammatory or angiogenic ophthalmic disease or disorder in a mammal, the method comprising the step of applying to the eye of the mammal in need of such treatment an ophthalmic composition comprising a therapeutically effective amount of a shark cartilage extract comprising one or more biologically active components, a majority of which have a molecular weight less than about 500 kDa.

20. The method according to claim 19, wherein the ophthalmic disease or disorder is selected from the group consisting of corneal neovascularization, corneal infection, neovascular glaucoma, macular degeneration, and diabetic retinopathy.

21. The method of claim 19, wherein the shark cartilage extract has been prepared by a process comprising the step of:
first fractionating a crude cartilage extract comprising water soluble biologically active components obtained from shark cartilage material such that a major portion of the biologically active components having a molecular weight greater than about 500 kDa is separated from a major portion of biologically active components having a molecular weight of less than about 500 kDa to form the shark cartilage extract.

22. A method of treating a disease or disorder selected from the group consisting of hypertrophic scar, alopecia, multiple sclerosis, fibrosis, inflammatory bowel disease, scleroderma, vasoconstrictive diseases, herpes virus keratitis, and organ graft rejection, the method comprising the step of administering to a patient in need of such treatment a composition comprising a therapeutically effective amount of a shark cartilage extract comprising one more biologically active components, a majority of which have a molecular weight less than about 500 kDa.

23. The method of claim 22, wherein the shark cartilage extract has been prepared by a process comprising the step of:
first fractionating a crude cartilage extract comprising water soluble biologically active components obtained from shark cartilage material such that a major portion of the biologically active components having a molecular weight greater than about 500 kDa is separated from a major portion of biologically active components having a molecular weight of less than about 500 kDa to form the shark cartilage extract.

24. A method of treating a disease or disorder having an etiology related to any one of tumour proliferation, angiogenesis, metalloprotease activity and inflammation, the method comprising the step of administering a therapeutically effective amount of a shark cartilage extract comprising water soluble biologically active components, a majority of which have a molecular weight lower than about 500 kDa, the extract being obtained from a process comprising the step of:
fractionating a crude cartilage extract comprising water soluble biologically active components obtained from cartilage material, such that a major portion of the biologically active components having a molecular weight greater than about 500 kDa is separated from a major portion of biologically active components having a molecular weight of less than about 500 kDa to form the shark cartilage extract.

25. The method of claim 24, wherein the disease or disorder is one affecting skin or mucosae.

26. The method of claim 24, wherein the method is one or more of:
a method for reducing inflammation in mammalian skin;
a method for inhibiting metalloprotease activity in mammalian skin;
a method for inhibiting endothelial cell proliferation in mammalian skin;
a method for inhibiting cancer cell proliferation in mammalian skin;
a method for enhancing skin barrier function in mammalian skin;
a method for regulating wrinkles and atrophy in mammalian skin;
a method for retarding premature aging in mammalian skin;
a method for soothing irritation in mammalian skin;
a method for inhibiting activated-keratinocyte differentiation; and
a method for decreasing the expression of eczema or acne in mammalian skin.

27. The method of claim 26, wherein said inflammation is caused by a chemical irritant, a physical abrasion, U.V. radiation, an allergen or an infectious agent.

28. A composition comprising an effective amount of a shark cartilage extract comprising water soluble biologically active components, a majority of which have a molecular weight lower than 500 kDa, the extract being prepared by a process comprising the step of:
first fractionating a crude cartilage extract comprising water soluble biologically active components obtained from cartilage material such that a major portion of the biologically active components having a molecular weight greater than about 500 kDa is separated from a major portion of biologically active components having a molecular weight of less than about 500 kDa to form said shark cartilage extract, and a pharmaceutically acceptable carrier.

29. The composition of claim 28, wherein the composition is one of a topical, ophthalmic and cosmetic composition.

30. The composition of claim 28, wherein the composition is one of an ointment, cream, emulsion, suspension, gel, liquid, tincture, spray, stick, liposome, ophthalmic drop and lotion.

31. The composition of claim 28 further comprising at least one of:
an antioxidant, an anti-inflammatory agent, an anti-irritant, a keratinolytic agent, a surface active agent, a preservative, a stabilizer, a synthetic polymer, a buffer, a cream base, an ointment base, and a salt.

32. The composition of claim 28, wherein the process of preparing the cartilage extract further comprises the step of concentrating said shark cartilage extract.

33. The composition of claim 32, wherein the step of concentrating comprises one or more of:
second fractionating the shark cartilage extract to remove a major portion of water and water soluble components having a molecular weight less than about 0.1 kDa;
second fractionating the shark cartilage extract to remove a major portion of water and water soluble components having a molecular weight less than about 1 kDa; and lyophilizing or evaporating a major portion of the liquid from said shark cartilage extract.

34. A shark cartilage extract prepared according to a process comprising the steps of:
a) first fractionating a crude shark cartilage extract comprising water soluble biologically active components obtained from shark cartilage material such that a major portion of the biologically active components having a molecular weight greater than about 500 kDa is separated and removed from a major portion of biologically active components having a molecular weight of less than about 500 kDa to form a first fractionated extract;

b) second fractionating said first fractionated extract such that a major portion of the biologically active components having a molecular weight lower than about 10 kDa is separated and removed from a major portion of the biologically active components having a molecular weight comprised between about 10 to 500 kDa, to form a second fractionated extract; and c) third fractionating said second fractionated extract on an anion exchange chromatography medium to recover a third fractionated extract which elutes in a NaCl concentration gradient and has an antiangiogenic activity to form said cartilage extract.

35. An antiangiogenic composition comprising the shark cartilage extract of claim 34 and a pharmaceutically acceptable carrier.

36. The shark cartilage extract of claim 34, wherein the third fractionated extract elutes at 0.8 to 1 M NaCl and the chromatography medium is Mono-Q.

* * * * *